United States Patent
Wyder et al.

(10) Patent No.: US 11,798,164 B2
(45) Date of Patent: *Oct. 24, 2023

(54) ARTIFICIAL INTELLIGENCE FOR EVALUATION OF OPTICAL COHERENCE TOMOGRAPHY IMAGES

(71) Applicant: ACUCELA INC., Seattle, WA (US)

(72) Inventors: Stephan Wyder, Bern (CH); Matthias Pfister, Liebefeld-Bern (CH); Cyril Stoller, Gumligen (CH); Philip M. Buscemi, Mount Pleasant, SC (US)

(73) Assignee: ACUCELA INC., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/177,560

(22) Filed: Mar. 2, 2023

(65) Prior Publication Data

US 2023/0206440 A1 Jun. 29, 2023

Related U.S. Application Data

(63) Continuation of application No. 17/805,299, filed on Jun. 3, 2022, now Pat. No. 11,620,749, which is a
(Continued)

(51) Int. Cl.
*G06T 7/00* (2017.01)
*G06T 7/11* (2017.01)
(Continued)

(52) U.S. Cl.
CPC ............ *G06T 7/0012* (2013.01); *G06N 3/08* (2013.01); *G06T 3/00* (2013.01); *G06T 7/11* (2017.01);
(Continued)

(58) Field of Classification Search
CPC . G06T 7/0012; G06T 3/00; G06T 7/11; G06T 2207/10101; G06T 2207/20081;
(Continued)

(56) References Cited

U.S. PATENT DOCUMENTS

| 5,255,274 A | 10/1993 | Wysocki |
| 5,396,325 A | 3/1995 | Carome |

(Continued)

FOREIGN PATENT DOCUMENTS

| CA | 3111012 | 1/2021 |
| CN | 105188540 | 12/2015 |

(Continued)

OTHER PUBLICATIONS

English Translation of CN111257282A (Year: 2020).*
(Continued)

*Primary Examiner* — Jon Chang
(74) *Attorney, Agent, or Firm* — FISHERBROYLES LLP; John Shimmick

(57) ABSTRACT

A neural network is trained to segment interferogram images. A first plurality of interferograms are obtained, where each interferograms corresponds to data acquired by an OCT system using a first scan pattern, annotating each of the plurality of interferograms to indicate a tissue structure of a retina, training a neural network using the plurality of interferograms and the annotations, inputting a second plurality of interferograms corresponding to data acquired by an OCT system using a second scan pattern and obtaining an output of the trained neural network indicating the tissue structure of the retina that was scanned using the second scan pattern. The system and methods may instead receive a plurality of A-scans and output a segmented image corresponding to a plurality of locations along an OCT scan pattern.

21 Claims, 22 Drawing Sheets

Related U.S. Application Data continuation of application No. 17/444,806, filed on Aug. 10, 2021, now Pat. No. 11,393,094.

(60) Provisional application No. 62/706,800, filed on Sep. 11, 2020.

(51) Int. Cl.
    *G06T 3/00* (2006.01)
    *G06V 10/82* (2022.01)
    *G06N 3/08* (2023.01)
    *G16H 30/40* (2018.01)

(52) U.S. Cl.
    CPC ... *G16H 30/40* (2018.01); *G06T 2207/10101* (2013.01); *G06T 2207/20081* (2013.01); *G06T 2207/20084* (2013.01); *G06T 2207/30041* (2013.01); *G06V 10/82* (2022.01); *G06V 2201/03* (2022.01)

(58) Field of Classification Search
    CPC . G06T 2207/20084; G06T 2207/30041; G06T 5/001; G06V 10/82; G06V 2201/03; G06V 10/26; G06V 10/7747; G06N 3/08; G06N 3/045; G16H 30/40; G16H 20/40; G16H 50/20
    See application file for complete search history.

(56) References Cited

U.S. PATENT DOCUMENTS

| | | |
|---|---|---|
| 6,053,613 A | 4/2000 | Wei |
| 6,325,512 B1 | 12/2001 | Wei |
| 6,362,919 B1 | 3/2002 | Flanders |
| 6,409,395 B1 | 6/2002 | Wang |
| 6,419,360 B1 | 7/2002 | Hauger |
| 6,445,944 B1 | 9/2002 | Ostrovsky |
| 6,552,796 B2 | 4/2003 | Magnin |
| 6,726,325 B2 | 4/2004 | Xie |
| 6,736,508 B2 | 5/2004 | Xie |
| 6,769,769 B2 | 8/2004 | Podoleanu |
| 6,778,307 B2 | 8/2004 | Clark |
| 7,113,818 B2 | 9/2006 | Podoleanu |
| 7,126,693 B2 | 10/2006 | Everett |
| 7,140,730 B2 | 11/2006 | Wei |
| 7,301,644 B2 | 11/2007 | Knighton |
| 7,324,569 B2 | 1/2008 | Flanders |
| 7,347,548 B2 | 3/2008 | Huang |
| 7,375,818 B2 | 5/2008 | Kawahara |
| 7,391,520 B2 | 6/2008 | Zhou |
| 7,452,077 B2 | 11/2008 | Meyer |
| 7,482,589 B2 | 1/2009 | Flanders |
| 7,542,145 B2 | 6/2009 | Toida |
| 7,594,730 B2 | 9/2009 | Podoleanu |
| 7,602,500 B2 | 10/2009 | Izatt |
| 7,633,623 B2 | 12/2009 | Hatori |
| 7,633,627 B2 | 12/2009 | Choma |
| 7,701,585 B2 | 4/2010 | Hatori |
| 7,761,139 B2 | 7/2010 | Tearney |
| 7,783,337 B2 | 8/2010 | Feldman |
| 7,864,335 B2 | 1/2011 | Terakawa |
| 7,872,759 B2 | 1/2011 | Tearney |
| 7,929,148 B2 | 4/2011 | Kemp |
| 7,954,947 B2 | 6/2011 | Sugita |
| 7,971,999 B2 | 7/2011 | Zinser |
| 7,980,694 B2 | 7/2011 | Keating |
| 7,980,696 B1 | 7/2011 | Taki |
| 7,997,728 B2 | 8/2011 | Huang |
| 7,997,729 B2 | 8/2011 | McLean |
| 8,025,403 B2 | 9/2011 | Maloca |
| 8,049,900 B2 | 11/2011 | Kemp |
| 8,055,107 B2 | 11/2011 | Masuda |
| 8,079,711 B2 | 12/2011 | Stetson |
| 8,123,354 B2 | 2/2012 | Olivier |
| 8,139,226 B2 | 3/2012 | Johnson |
| 8,192,024 B2 | 6/2012 | Yumikake |
| 8,205,991 B2 | 6/2012 | Wei |
| 8,220,924 B2 | 7/2012 | Hanebuchi |
| 8,251,510 B2 | 8/2012 | Kobayashi |
| 8,251,511 B2 | 8/2012 | Stetson |
| 8,282,211 B2 | 10/2012 | Campbell |
| 8,289,522 B2 | 10/2012 | Tearney |
| 8,348,427 B2 | 1/2013 | Buckland |
| 8,348,429 B2 | 1/2013 | Walsh |
| 8,351,665 B2 | 1/2013 | Tearney |
| 8,363,783 B2 | 1/2013 | Gertner |
| 8,403,481 B2 | 3/2013 | Izatt |
| 8,405,834 B2 | 3/2013 | Srinivasan |
| 8,421,855 B2 | 4/2013 | Buckland |
| 8,425,037 B2 | 4/2013 | Uhlhorn |
| 8,442,284 B2 | 5/2013 | Rogers |
| 8,446,593 B1 | 5/2013 | Ellerbee |
| 8,457,440 B1 | 6/2013 | Johnson |
| 8,467,051 B2 | 6/2013 | Flanders |
| 8,474,978 B2 | 7/2013 | Huang |
| 8,500,279 B2 | 8/2013 | Everett |
| 8,526,006 B2 | 9/2013 | Nebosis |
| 8,529,062 B2 | 9/2013 | Buckland |
| 8,594,757 B2 | 11/2013 | Boppart |
| 8,608,314 B2 | 12/2013 | Yoon |
| 8,630,697 B2 | 1/2014 | Meyer |
| 8,665,450 B2 | 3/2014 | Johnson |
| 8,711,366 B2 | 4/2014 | Everett |
| 8,721,078 B2 | 5/2014 | Torii |
| 8,724,870 B2 | 5/2014 | Sekine |
| 8,757,803 B2 | 6/2014 | Everett |
| 8,781,287 B2 | 7/2014 | Flanders |
| 8,794,763 B2 | 8/2014 | Stetson |
| 8,801,184 B2 | 8/2014 | Hacker |
| 8,820,931 B2 | 9/2014 | Walsh |
| 8,836,953 B2 | 9/2014 | Johnson |
| 8,870,376 B2 | 10/2014 | Hogan |
| 8,894,207 B2 | 11/2014 | Hee |
| 8,913,248 B2 | 12/2014 | Sharma |
| 8,922,782 B2 | 12/2014 | Flanders |
| 8,926,097 B2 | 1/2015 | Sakagawa |
| 8,939,582 B1 | 1/2015 | Spaide |
| 8,947,648 B2 | 2/2015 | Swanson |
| 8,953,167 B2 | 2/2015 | Johnson |
| 8,971,360 B2 | 3/2015 | Lewandowski |
| 8,992,018 B2 | 3/2015 | Makihira |
| 8,994,753 B2 | 3/2015 | Nakano |
| 8,998,412 B2 | 4/2015 | Makihira |
| 9,016,862 B2 | 4/2015 | Carnevale |
| 9,025,160 B2 | 5/2015 | Moore |
| 9,025,847 B2 | 5/2015 | Kitamura |
| 9,033,504 B2 | 5/2015 | Everett |
| 9,033,510 B2 | 5/2015 | Narasimha-Iyer |
| 9,044,164 B2 | 6/2015 | Hacker |
| 9,055,891 B2 | 6/2015 | Suehira |
| 9,055,892 B2 | 6/2015 | Narasimha-Iyer |
| 9,060,689 B2 | 6/2015 | Tearney |
| 9,084,562 B2 | 7/2015 | Kakuma |
| 9,095,281 B2 | 8/2015 | Sharma |
| 9,119,562 B2 | 9/2015 | Naba |
| 9,138,141 B2 | 9/2015 | Makihira |
| 9,144,378 B2 | 9/2015 | Suehira |
| 9,149,182 B2 | 10/2015 | Walsh |
| 9,161,690 B2 | 10/2015 | Tomatsu |
| 9,163,929 B2 | 10/2015 | Lim |
| 9,163,930 B2 | 10/2015 | Buckland |
| 9,167,964 B2 | 10/2015 | Everett |
| 9,171,367 B2 | 10/2015 | Iwase |
| 9,176,319 B2 | 11/2015 | Bouma |
| 9,178,330 B2 | 11/2015 | Oh |
| 9,192,294 B2 | 11/2015 | Sharma |
| 9,200,888 B2 | 12/2015 | Jaillon |
| 9,217,707 B2 | 12/2015 | Bajraszewski |
| 9,226,653 B2 | 1/2016 | Torii |
| 9,226,660 B2 | 1/2016 | De Boer |
| 9,241,626 B2 | 1/2016 | Narasimha-Iyer |
| 9,243,885 B2 | 1/2016 | Johnson |
| 9,259,151 B2 | 2/2016 | Murase |

(56) References Cited

U.S. PATENT DOCUMENTS

| | | |
|---|---|---|
| 9,267,783 B1 | 2/2016 | Sharma |
| 9,273,950 B2 | 3/2016 | Yazdanfar |
| 9,291,446 B2 | 3/2016 | Schneider |
| 9,310,182 B2 | 4/2016 | Goldberg |
| 9,339,186 B2 | 5/2016 | Somani |
| 9,354,038 B2 | 5/2016 | Yasuno |
| 9,373,933 B2 | 6/2016 | Njegovec |
| 9,375,158 B2 | 6/2016 | Vakoc |
| 9,377,293 B2 | 6/2016 | Hauger |
| 9,380,935 B2 | 7/2016 | Iwase |
| 9,408,532 B2 | 8/2016 | Makihira |
| 9,427,147 B2 | 8/2016 | Lujan |
| 9,427,150 B2 | 8/2016 | Muto |
| 9,433,353 B2 | 9/2016 | Hanebuchi |
| 9,468,374 B2 | 10/2016 | Makihira |
| 9,492,077 B2 | 11/2016 | Ebersbach |
| 9,492,079 B2 | 11/2016 | Walsh |
| 9,526,412 B2 | 12/2016 | Yang |
| 9,526,415 B2 | 12/2016 | Fukuma |
| 9,526,425 B2 | 12/2016 | Feldman |
| 9,532,713 B2 | 1/2017 | Levecq |
| 9,545,199 B2 | 1/2017 | Wang |
| 9,584,098 B2 | 2/2017 | Yamanari |
| 9,612,105 B2 | 4/2017 | Kemp |
| 9,615,736 B2 | 4/2017 | Yamashita |
| 9,633,424 B2 | 4/2017 | Nebosis |
| 9,649,024 B2 | 5/2017 | Hacker |
| 9,649,025 B2 | 5/2017 | Jeglorz |
| 9,671,620 B2 | 6/2017 | Gupta |
| 9,696,132 B2 | 7/2017 | Jayaraman |
| 9,702,686 B2 | 7/2017 | Hattersley |
| 9,778,018 B2 | 10/2017 | Schmoll |
| 9,778,020 B2 | 10/2017 | Tumlinson |
| 9,784,559 B2 | 10/2017 | Huber |
| 9,812,846 B2 | 11/2017 | Yun |
| 9,869,542 B2 | 1/2018 | Goldberg |
| 9,897,538 B2 | 2/2018 | Tearney |
| 9,915,520 B2 | 3/2018 | Cable |
| 9,939,659 B2 | 4/2018 | Gupta |
| 9,948,061 B2 | 4/2018 | Njegovec |
| 9,977,184 B1 | 5/2018 | Wong |
| 9,978,159 B2 | 5/2018 | Kraus |
| 9,993,153 B2 | 6/2018 | Chong |
| 10,045,692 B2 | 8/2018 | Tumlinson |
| 10,049,470 B2 | 8/2018 | Pintal |
| 10,098,537 B2 | 10/2018 | Iwase |
| 10,114,232 B2 | 10/2018 | Gupta |
| 10,327,631 B2 | 6/2019 | Huang |
| 10,413,175 B2 | 9/2019 | Yun |
| 10,478,058 B2 | 11/2019 | Cheng |
| 10,568,501 B2 | 2/2020 | Boss |
| 10,595,723 B2 | 3/2020 | Meznaric |
| 10,610,096 B2 | 4/2020 | Scheibler |
| 10,912,456 B2 | 2/2021 | Brennan |
| 10,952,607 B2 | 3/2021 | Scheibler |
| 10,959,613 B1 | 3/2021 | Kubota |
| 11,357,401 B2 | 6/2022 | Oggenfuss et al. |
| 11,369,266 B2 | 6/2022 | Kubota |
| 11,393,094 B2 | 7/2022 | Wyder |
| 11,497,396 B2 | 11/2022 | Kubota |
| 11,576,572 B2 | 2/2023 | Oggenfuss |
| 11,620,749 B2 | 4/2023 | Wyder |
| 11,627,874 B2 | 4/2023 | Scheibler |
| 2005/0018133 A1 | 1/2005 | Huang |
| 2005/0140981 A1 | 6/2005 | Waelti |
| 2006/0131488 A1 | 6/2006 | Thingbo |
| 2006/0152106 A1 | 7/2006 | Yan |
| 2006/0244339 A1 | 11/2006 | Mazz |
| 2007/0076217 A1 | 4/2007 | Baker |
| 2007/0183643 A1 | 8/2007 | Jayaraman |
| 2007/0230856 A1 | 10/2007 | Yamazaki |
| 2007/0263171 A1 | 11/2007 | Ferguson |
| 2008/0100612 A1 | 5/2008 | Dastmalchi |
| 2008/0117427 A1 | 5/2008 | Teramura |
| 2008/0181263 A1 | 7/2008 | Bouma |
| 2008/0296480 A1 | 12/2008 | Haber |
| 2009/0123044 A1 | 5/2009 | Huang |
| 2009/0141237 A1 | 6/2009 | Izatt |
| 2009/0244485 A1 | 10/2009 | Walsh |
| 2010/0110376 A1 | 5/2010 | Everett |
| 2010/0110377 A1 | 5/2010 | Maloca |
| 2011/0043757 A1 | 2/2011 | Everett |
| 2011/0080561 A1 | 4/2011 | Hayashi |
| 2011/0164633 A1 | 7/2011 | Moench |
| 2011/0299034 A1 | 12/2011 | Walsh |
| 2012/0033227 A1 | 2/2012 | Bower |
| 2012/0092616 A1 | 4/2012 | Peyman |
| 2012/0300216 A1 | 11/2012 | Johnson |
| 2012/0327365 A1 | 12/2012 | Makihira |
| 2013/0010259 A1 | 1/2013 | Carnevale |
| 2013/0010302 A1 | 1/2013 | Sharma |
| 2013/0016360 A1 | 1/2013 | Ensher |
| 2013/0103014 A1 | 4/2013 | Gooding |
| 2013/0158392 A1 | 6/2013 | Papac |
| 2013/0235343 A1 | 9/2013 | Hee |
| 2013/0250241 A1 | 9/2013 | Everett |
| 2014/0028997 A1 | 1/2014 | Cable |
| 2014/0112562 A1 | 4/2014 | Yamakawa |
| 2014/0121508 A1 | 5/2014 | Latimer |
| 2014/0125987 A1 | 5/2014 | Flanders |
| 2014/0218745 A1 | 8/2014 | Hattersley |
| 2014/0241605 A1 | 8/2014 | Izatt |
| 2014/0268050 A1 | 9/2014 | Jayaraman |
| 2014/0268169 A1 | 9/2014 | Jayaraman |
| 2014/0269796 A1 | 9/2014 | Geske |
| 2014/0285812 A1 | 9/2014 | Levitz |
| 2014/0307078 A1 | 10/2014 | Charles |
| 2014/0307753 A1 | 10/2014 | Minneman |
| 2014/0340689 A1 | 11/2014 | Namati |
| 2014/0347632 A1 | 11/2014 | Mordaunt |
| 2015/0010031 A1 | 1/2015 | Makino |
| 2015/0018674 A1 | 1/2015 | Scott |
| 2015/0055089 A1 | 2/2015 | Aono |
| 2015/0062532 A1 | 3/2015 | Sharma |
| 2015/0085253 A1 | 3/2015 | Walsh |
| 2015/0109579 A1 | 4/2015 | Orlowski |
| 2015/0110376 A1 | 4/2015 | Gessner |
| 2015/0198431 A1 | 7/2015 | Uchida |
| 2015/0216408 A1 | 8/2015 | Brown |
| 2015/0216412 A1 | 8/2015 | Hillmann |
| 2015/0230705 A1 | 8/2015 | Kato |
| 2015/0327761 A1 | 11/2015 | Narasimha-Iyer |
| 2015/0327762 A1 | 11/2015 | Isogai |
| 2016/0000368 A1 | 1/2016 | Wang |
| 2016/0007857 A1 | 1/2016 | Wang |
| 2016/0025478 A1 | 1/2016 | Johnson |
| 2016/0040976 A1 | 2/2016 | Berkeley |
| 2016/0040977 A1 | 2/2016 | An |
| 2016/0040978 A1 | 2/2016 | Boppart |
| 2016/0081545 A1 | 3/2016 | Hauger |
| 2016/0082129 A1 | 3/2016 | Peters |
| 2016/0106310 A1 | 4/2016 | Moriguchi |
| 2016/0106312 A1 | 4/2016 | Moriguchi |
| 2016/0106314 A1 | 4/2016 | Everett |
| 2016/0128565 A1 | 5/2016 | Meznaric |
| 2016/0166143 A1 | 6/2016 | Goto |
| 2016/0206190 A1 | 7/2016 | Reisman |
| 2016/0242638 A1 | 8/2016 | Durbin |
| 2016/0252340 A1 | 9/2016 | Hollenbeck |
| 2016/0262609 A1 | 9/2016 | Cai |
| 2016/0270656 A1 | 9/2016 | Samec |
| 2016/0321828 A1 | 11/2016 | Tachikawa |
| 2016/0338589 A1 | 11/2016 | Carrasco-Zevallos |
| 2016/0367129 A1 | 12/2016 | Coelho |
| 2016/0367132 A1 | 12/2016 | Yun |
| 2017/0007182 A1 | 1/2017 | Samec |
| 2017/0020387 A1 | 1/2017 | Fingler |
| 2017/0049318 A1 | 2/2017 | Walsh |
| 2017/0055829 A1 | 3/2017 | Tan |
| 2017/0065169 A1 | 3/2017 | Fukasawa |
| 2017/0074640 A1 | 3/2017 | Cable |
| 2017/0102223 A1 | 4/2017 | Izatt |
| 2017/0105618 A1 | 4/2017 | Schmoll |
| 2017/0140560 A1 | 5/2017 | Kraus |

(56) References Cited

U.S. PATENT DOCUMENTS

| | | |
|---|---|---|
| 2017/0156583 A1 | 6/2017 | Seesselberg |
| 2017/0205223 A1 | 7/2017 | Cable |
| 2017/0227350 A1 | 8/2017 | Sarunic |
| 2017/0231489 A1 | 8/2017 | Fujimori |
| 2017/0241763 A1 | 8/2017 | Wang |
| 2017/0258321 A1 | 9/2017 | Dastmalchi |
| 2017/0268987 A1 | 9/2017 | Swanson |
| 2017/0276471 A1 | 9/2017 | Jiang |
| 2017/0280993 A1 | 10/2017 | Fukuhara |
| 2017/0311795 A1 | 11/2017 | Sumiya |
| 2017/0356740 A1 | 12/2017 | Ansari |
| 2018/0012359 A1 | 1/2018 | Prentasic |
| 2018/0031363 A1 | 2/2018 | Johnson |
| 2018/0051978 A1 | 2/2018 | Flanders |
| 2018/0055358 A1 | 3/2018 | Nakajima |
| 2018/0064331 A1 | 3/2018 | Naba |
| 2018/0084994 A1 | 3/2018 | Su |
| 2018/0125354 A1 | 5/2018 | Pulaski |
| 2018/0135962 A1 | 5/2018 | Murata |
| 2018/0156598 A1 | 6/2018 | Cable |
| 2018/0157924 A1 | 6/2018 | Hogan |
| 2018/0168445 A1 | 6/2018 | Horn |
| 2018/0206716 A1 | 7/2018 | Chong |
| 2018/0271363 A1 | 9/2018 | Scheibler et al. |
| 2018/0289256 A1 | 10/2018 | Murata |
| 2019/0365220 A1 | 12/2019 | Frisken |
| 2019/0380574 A1 | 12/2019 | Chen |
| 2020/0093363 A1 | 3/2020 | Saika |
| 2020/0196858 A1 | 6/2020 | Scheibler |
| 2020/0234080 A1 | 7/2020 | Ciller Ruiz |
| 2020/0342595 A1 | 10/2020 | Jia |
| 2020/0372632 A1 | 11/2020 | Chauhan |
| 2021/0127969 A1 | 5/2021 | Oggenfuss |
| 2021/0196113 A1 | 7/2021 | Copland |
| 2021/0235984 A1 | 8/2021 | Scheibler |
| 2021/0319556 A1* | 10/2021 | Chauhan ............. G06T 7/12 |
| 2021/0386285 A1 | 12/2021 | Walsh |
| 2022/0265140 A1 | 8/2022 | Oggenfuss |
| 2022/0301161 A1 | 9/2022 | Wyder |

FOREIGN PATENT DOCUMENTS

| | | |
|---|---|---|
| CN | 105263415 | 1/2016 |
| CN | 105792728 | 7/2016 |
| CN | 111257282 A * | 6/2020 ............. G01N 21/01 |
| DE | 102016121246 | 5/2018 |
| EP | 2725508 | 4/2014 |
| EP | 2759254 | 7/2014 |
| EP | 2892413 | 7/2015 |
| JP | 201172716 | 4/2011 |
| JP | 2011515194 | 5/2011 |
| JP | 201483266 | 5/2014 |
| JP | 2016513889 | 5/2016 |
| JP | 2016514828 | 5/2016 |
| WO | 9320743 | 10/1993 |
| WO | 2009120544 | 10/2009 |
| WO | 2010117386 | 10/2010 |
| WO | 2014144866 | 9/2014 |
| WO | 2014144998 | 9/2014 |
| WO | 2015082001 | 6/2015 |
| WO | 2015116981 | 8/2015 |
| WO | 2015120055 | 8/2015 |
| WO | 2016040534 | 3/2016 |
| WO | 2016073840 | 5/2016 |
| WO | 2016115387 | 7/2016 |
| WO | 2016125474 | 8/2016 |
| WO | 2016127140 | 8/2016 |
| WO | 2016148569 | 9/2016 |
| WO | 2016178298 | 11/2016 |
| WO | 2016179431 | 11/2016 |
| WO | 2016196463 | 12/2016 |
| WO | 2016203245 | 12/2016 |
| WO | 2017002379 | 1/2017 |
| WO | 2017025583 | 2/2017 |
| WO | 2017046225 | 3/2017 |
| WO | 2017048832 | 3/2017 |
| WO | 2017165793 | 9/2017 |
| WO | 2017176301 | 10/2017 |
| WO | 2017206929 | 12/2017 |
| WO | 2017216242 | 12/2017 |
| WO | 2018086173 | 5/2018 |
| WO | 2018089682 | 5/2018 |
| WO | 2018105549 | 6/2018 |
| WO | 2018116128 | 6/2018 |
| WO | 2018119077 | 6/2018 |
| WO | 2019210079 | 10/2019 |
| WO | 2019246412 | 12/2019 |
| WO | 2020036182 | 2/2020 |
| WO | 2020160839 A1 | 8/2020 |
| WO | 2021134087 | 7/2021 |
| WO | 2022204622 | 9/2022 |

OTHER PUBLICATIONS

Bengio, Yoshua, et al., "Curriculum Learning," 8 pages, retrieved from http://machinelearning.org/archive/icml2009/papers/119.pdf on Jun. 14, 2021.

Bertera, J.H., et al., "Stabilized Retinal Mapping of Known Retinal Loci," Proceedings of the Annual Northeast Bioengineering Conference, IEEE, vol. Conf. 14, No. 1988, XP000010509 (Mar. 10, 1988).

Girish et al. Segmentation of Intra-Retinal Cysts From Optical Coherence Tomography Images Using a Fully Convolutional Neural Network Model. IEEE Journal of Biomedical and Health Informatics, vol. 23, No. 1, Jan. 2019, pp. 296-304 (Year: 2019).

Haglund, Erik, et al., "Multi-wavelength VCSEL arrays using high-contrast gratings," Proc. of SPIE vol. 10113, 7 pages (2017).

Huang, et al., "Optical coherence tomograph," Science, 254(5035):1178-1181 (Nov. 22, 1991).

Huang, Huimin, et al., "UNET 3+: A Full-Scale Connected UNET for Medical Image Segmentation," 5 pages, retrieved from https://arxiv.org/ftp/arxiv/papers/2004/2004.08790.pdf on Jun. 14, 2021.

International Search Report and Written Opinion for PCT/US2021/071342, 16 pages (dated Feb. 28, 2022).

Jayaraman, V., et al., "Recent Advances in MEMS-VCSELs for High Performance Structural and Functional SS-OCT Imaging," Proc. of SPIE vol. 8934, retrieved from http://proceedings.spiedigitallibrary.org/ on Dec. 1, 2015 (2014).

Khan, Zuhaib, et al., "High-brightness and high-speed vertical-cavity surface-emitting laser arrays," Optica, 7(4):267-275 (Apr. 2020).

Kolb, Jan Philip, et al., "High-resolution retinal swept source optical coherence tomography with an ultra-wideband Fourier-domain mode-locked laser at MHz A-scan rates," Biomedical Optics Express, 9(1):120-130 (2018).

Mishra, Z., et al., "Automated Retinal Layer Segmentation Using Graph-based Algorithm Incorporating Deep-learning-derived Information," Sci Rep. 10(1):9541 (2020).

Moon, S., et al., "VCSEL-based swept source for low-cost optical coherence tomography", Biomedical Optics Express, 8(2):1110-1121 (Feb. 1, 2017).

ORR. Notal Vision—Home-Based Optical Coherence Tomograph (OCT). Slide deck (11 pgs.) (Nov. 9, 2017).

Pierro, L., et al., "Macular Thickness Interoperator and Intraoperator Reproducibility in Healthy Eyes Using 7 Optical Coherence Tomography Instruments," American Journal of Ophthalmology, 150(2): 199-204, XP027174249 (Aug. 1, 2010).

Sanghoon, Kim, et al., "Design and implementation of a low-cost, portable OCT system," 9(3):1232-1243 (Mar. 1, 2018).

WO 2020/036182 A1 machine translation from Japanese to English (132 pages).

Zara, J.M., et al., "Electrostatic micromachine scanning mirror for optical coherence tomography, " Optics Letters, 28(8):628-630 (Apr. 15, 2003).

* cited by examiner

ARTIFICIAL INTELLIGENCE FOR EVALUATION OF OPTICAL COHERENCE TOMOGRAPHY IMAGES

RELATED APPLICATIONS

This application is a continuation of U.S. patent application Ser. No. 17/805,299, filed Jun. 3, 2022, now U.S. Pat. No. 11,620,749, issued Apr. 4, 2023, which is a continuation of U.S. patent application Ser. No. 17/444,806, filed Aug. 10, 2021, now U.S. Pat. No. 11,393,094, issued Jul. 19, 2022, which claims the benefit under 35 U.S.C. § 119(e) of U.S. Provisional Patent Application No. 62/706,800, filed Sep. 11, 2020, the entire disclosures of which are incorporated, in their entirety, by this reference.

The subject matter of the present application is related to U.S. Provisional Patent Application No. 62/953,827, filed Dec. 26, 2019, the entire disclosure of which is incorporated herein by reference.

The disclosed approach to applying a trained Convolutional Neural Network (CNN) to assist in analyzing interferograms can be used with many scan patterns, such as one or more of a stop and go trajectory, a star trajectory, a continuous trajectory, or a Lissajous trajectory, as described in PCT/US2019/038270, filed Jun. 20, 2019, published as WO 2019/246412 on Dec. 26, 2019, the entire disclosure of which is incorporated herein by reference.

BACKGROUND

Eye health is critical for good vision. There are a variety of diseases and illnesses of the eye that can diagnosed by measuring changes in the structure of the eye. Such measurements can also provide indications of diseases that affect other organs of a patient. The structure of the eye includes a cornea and lens that refract light and form an image on the retina. The retina generates electrical signals in response to the image formed thereon, and these electrical signals are transmitted to the brain via the optic nerve. The fovea and macula of the retina have an increased density of cones in relation to other areas of the retina and provide sharper images.

Measurements of retinal thickness (RT) over time can be used to diagnose and monitor the health of the retina, the eye, and the patient. Many patients who have been diagnosed with retinal vascular diseases and other diseases or conditions have an elevated retinal thickness and are treated with medications. For example, macular edema is a disease that occurs when fluid collects on or under the macula of the retina, and results in an elevated retinal thickness. Macular edema can be an indication of other diseases, such as diabetes or age-related macular degeneration, uveitis, blockage of retinal vasculature, and glaucoma, for example. Thus, measurements of retinal thickness and determination of changes in thickness over time can be used as an indication of a change in eye health and other aspects of patient health.

Measurements of RT over time can also be used to evaluate the effectiveness of medications or treatments so that modifications can be made if needed. One way to do this is by making regular measurements of the thickness of a patient's retina. One technique used to measure the thickness of the retina is optical coherence tomography (OCT). OCT may also be used to generate data that can be used to form images of a patient's retina and its tissue structures. Such images may be used to evaluate the condition of the retina, and by inference, a patient's health.

At least some OCT devices include a source of a measurement beam, a scanner to move the beam on a patient's retina in a desired scan pattern, a set of optical elements to generate an interference pattern between a reference version of the measurement beam and light reflected from the retina, and a detector for detecting the interfering light waves. In some examples, an OCT system may also include a processor that executes a set of instructions to operate the scanner so as to move the measurement beam on the retina. The interference patterns created from a set of scans may be combined to form an image representing the layers or regions of the retina, termed an interferogram. Some interferometers function by splitting light from a single source into two beams that travel in different optical paths, and are then combined again to produce the interference patterns.

An interferogram may be subjected to further image processing to derive information about the retina, such as a measurement of the retinal thickness ("RT"), retinal hydration and fluid pooling. The retina includes layers of cells and tissue, such as the inner limiting membrane ("ILM") and retinal pigment epithelium ("RPE") layers. The image processing may be used to more clearly distinguish or segment the two layers. The measurement of RT over time may be used to diagnose illness or disease, such as by detecting evidence of fluid buildup or fluid pooling in the eye.

Although the detection of fluid pooling in and around the retina would be helpful, work in relation to the present disclosure suggests that the prior approaches can be less than ideal in at least some respects. For example, subtle changes in the gray scale values corresponding to a pool of fluid in an OCT image can be difficult for a health care professional to detect. Also, prior approaches that rely on high resolution systems to detect retinal fluid pools can be overly complex and of limited availability, such that pooling is detected later than would be ideal in at least some instances.

One method of processing interferogram images is to use a neural network architecture referred to as a convolutional neural network (CNN). A CNN is a form of deep learning network and consists of an input and an output layer, as well as multiple hidden layers. The hidden layers of a CNN consist of a series of layers that perform a convolution operation using a multiplication operation or implementation of a dot product. The activation function is commonly a rectified linear unit (RELU) layer and is subsequently followed by additional layers such as pooling layers, fully connected layers, and normalization layers. These are referred to as hidden layers because their inputs and outputs are masked by the activation function and final convolution. A trained CNN can be used to analyze an image and perform recognition of specific features. For example, a properly trained CNN may be used to identify layers or structures of an image of a retina in a process referred to as segmentation. This information can then be used to determine a measurement of retinal thickness or to otherwise evaluate a patient's eye or overall health.

A complication in the image processing is that different OCT systems may use different scan patterns when collecting data. This can make it difficult to compare interferograms obtained using different systems. It can also make it difficult to perform image recognition for an interferogram if there is insufficient data available to properly train a CNN to process that type of scan data. Embodiments of the disclosure are directed to overcoming these disadvantages of conventional methods of processing interferogram data, individually and collectively.

SUMMARY

The terms "invention," "the invention," "this invention," "the present invention," "the present disclosure," or "the disclosure" as used herein are intended to refer broadly to all of the subject matter described in this document, the drawings or figures, and to the claims. Statements containing these terms should be understood not to limit the subject matter described herein or to limit the meaning or scope of the claims. Embodiments of the invention covered by this patent are defined by the claims and not by this summary. This summary is a high-level overview of various aspects of the invention and introduces some of the concepts that are further described in the Detailed Description section below. This summary is not intended to identify key, essential or required features of the claimed subject matter, nor is it intended to be used in isolation to determine the scope of the claimed subject matter. The subject matter should be understood by reference to appropriate portions of the entire specification of this patent, to any or all figures or drawings, and to each claim.

In some embodiments, the system and methods may be used to perform image recognition and processing on interferogram images obtained from OCT scan data. The image recognition and processing may operate to segment the tissue layers of a retina to make them more distinguishable. The scan data may be the result of moving a measurement beam over a retina in a specific scan pattern. In some embodiments, a model or neural network, such as a convolutional neural network (CNN) may be trained using a set of scan data obtained from performing a set of scans using a radial scan pattern. The training data may also comprise scan data obtained from a different scan pattern that has been interpolated, extrapolated, resampled, or otherwise processed to more closely resemble data that would be obtained from a radial scan pattern. The other scan pattern may be a scan pattern that comprises a plurality of lobes, for example. After training, the CNN may be used to recognize or enhance the recognition of layers or structures of the retina, where in some embodiments, the input to the trained CNN is data obtained using the scan pattern with the plurality of lobes that has been interpolated, extrapolated, resampled, or otherwise processed to more closely resemble data that would be obtained from a radial scan pattern.

In some embodiments, the system and methods are directed to obtaining a first plurality of interferograms, wherein each of the interferograms corresponds to data acquired by an OCT system performing a scan of a retina using a first scan pattern, annotating each of the plurality of interferograms formed from the data acquired using the first scan pattern to indicate a tissue structure of the retina, training a neural network using the plurality of interferograms and the annotations, inputting a second plurality of interferograms corresponding to data acquired by an OCT system performing a scan of a retina using a second scan pattern and obtaining an output of the trained neural network, the output indicating the tissue structure of the retina that was scanned using the second scan pattern.

In some embodiments, the system and methods are directed to receiving a plurality of A-scans corresponding to a plurality of locations along an OCT scan pattern and outputting a segmented image corresponding to the plurality of locations along the OCT scan pattern, the segmented image comprising one or more of a boundary of an ILM layer, a boundary of an RPE layer, or a boundary of a pool of fluid within the retina.

In some embodiments, an OCT system may be operated with a specific scanning pattern for the measurement beam to enable the collection of data and provide more precise measurement of certain areas of the eye. The scanning pattern may result from moving a mirror that is part of the OCT system in response to a driving signal. The mirror intercepts a measurement beam generated by a light source and directs the beam to follow a trajectory that varies with the motion of the mirror, forming a predefined scan pattern. In some embodiments, data collected from using a scan pattern may be interpolated, extrapolated, resampled, or otherwise processed to obtain data that would be obtained from using a different scan pattern. This may assist a physician to better understand conditions in different regions of the eye or to compare scans taken with different scan patterns as part of monitoring the health of a patient's eyes.

In some embodiments, a swept measurement source may be varied in wavelength while a measurement beam is moved on a scan pattern, with the obtained data being subjected to a transform such as a Fourier transform prior to further processing.

In some embodiments, a processor may execute a set of computer-executable instructions to cause the processor or a device to access measurement data detected by a detector that is part of an OCT interferometer. In some embodiments, the processor may execute instructions to cause the processing of the accessed data to generate measurement data that would result from a different scan pattern. This may be used as additional training data for a neural network or as an input to a trained neural network.

In some embodiments, the processor may execute instructions to access a set of stored data for a plurality of A-scans, where each A-scan corresponds to a retinal pigment epithelium (RPE) and an inner limiting membrane (ILM) of the retina. The stored data may then be processed to enhance the distinction between the RPE and ILM, and as a result, assist in identifying changes to the retina thickness due to a buildup of fluid or formation of a fluid pocket. In some embodiments, the processing may comprise use of a trained CNN or other neural network or model to segment an image formed from a plurality of segmented A-scans.

Although specific reference is made to measuring retinal thickness, the image processing system and methods disclosed herein will find application in many fields, such as microscopy, metrology, aerospace, astronomy, telecommunications, medicine, pharmaceuticals, dermatology, dentistry, and cardiology.

Other objects and advantages of embodiments of the disclosure will be apparent to one of ordinary skill in the art upon review of the detailed description and the included figures.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
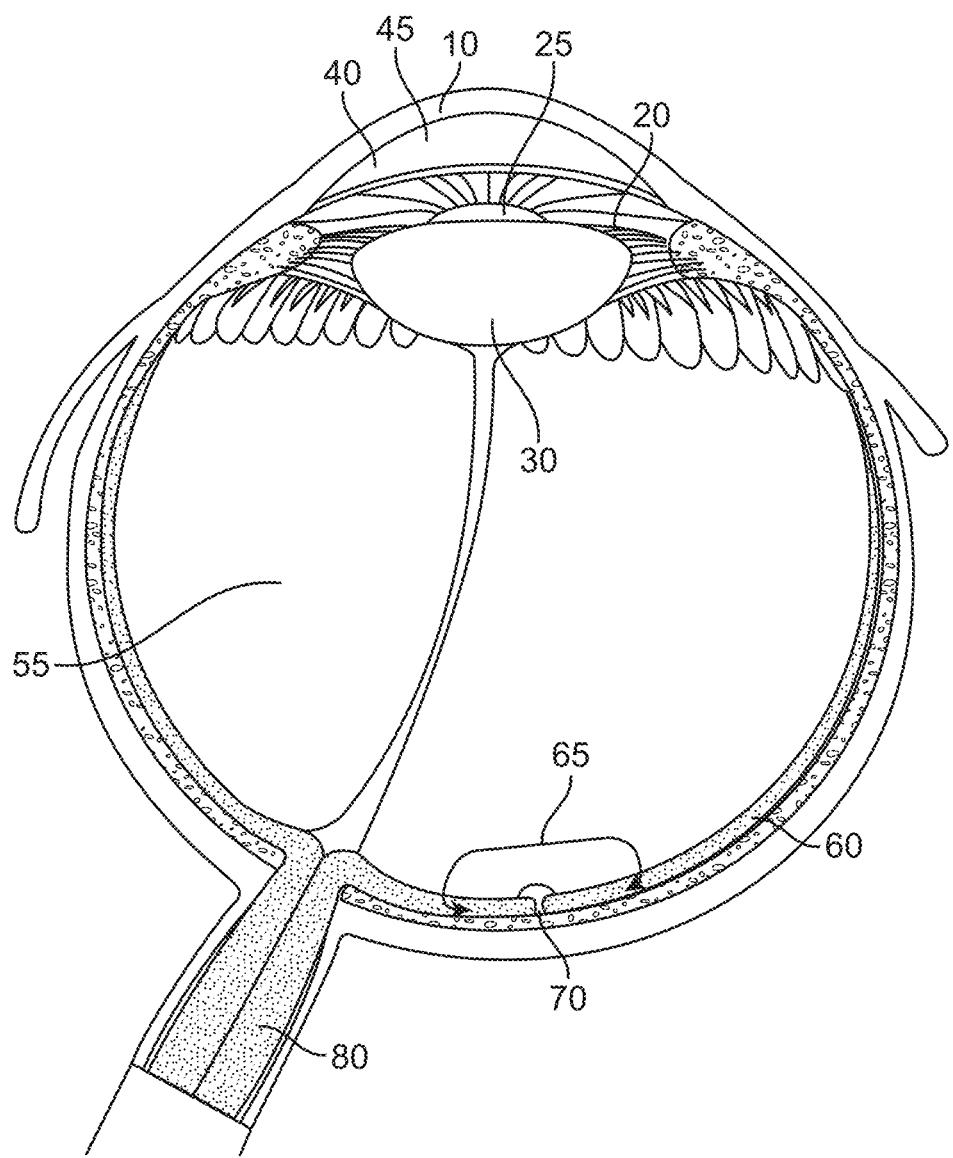
FIG. 1 shows a simplified diagram of the human eye.

The subject matter of embodiments of the present disclosure is described herein with specificity to meet statutory requirements, but this description is not intended to limit the scope of the claims. The claimed subject matter may be embodied in other ways, may include different elements or steps, and may be used in conjunction with other existing or later developed technologies. This description should not be interpreted as implying any required order or arrangement among or between various steps or elements except when the order of individual steps or arrangement of elements is explicitly noted as being required.

Embodiments of the present disclosure will be described more fully herein with reference to the accompanying drawings, which form a part hereof, and which show, by way of illustration, exemplary embodiments may be practiced. The embodiments disclosed herein may, however, be embodied in different forms and should not be construed as limited to the embodiments set forth herein; rather, these embodiments are provided so that this disclosure will satisfy the statutory requirements to those skilled in the art.

Among other things, the embodiments of the present disclosure may be embodied in whole or in part as a system, as one or more methods, or as one or more devices. Embodiments may take the form of a hardware implemented embodiment, a software implemented embodiment, or an embodiment combining software and hardware aspects. For example, in some embodiments, one or more of the operations, functions, processes, or methods described herein may be implemented by one or more suitable processing elements (such as a processor, microprocessor, CPU, GPU, TPU, controller, etc.) that is part of a client device, server, network element, remote platform (such as a SaaS platform), or other form of computing or data processing system, device, or platform.

The processing element or elements may be programmed with a set of executable instructions (e.g., software or computer-executable instructions), where the instructions may be stored in or on a suitable non-transitory data storage element. In some embodiments, one or more of the operations, functions, processes, or methods described herein may be implemented by a specialized form of hardware, such as a programmable gate array, application specific integrated circuit (ASIC), or the like. Note that an embodiment of the inventive methods may be implemented in the form of an application, a sub-routine that is part of a larger application, a "plug-in", an extension to the functionality of a data processing system or platform, or any other suitable form. The following detailed description is, therefore, not to be taken in a limiting sense.

While various embodiments have been shown and described herein, it will be obvious to those skilled in the art that such embodiments are provided by way of example only. Numerous variations, changes, and substitutions may occur to those skilled in the art without departing from the present disclosure. It should be understood that various alternatives to the embodiments described herein may be employed. For example, although reference is made to measuring a thickness of a sample such as the retina, the methods and apparatus disclosed herein can be used to measure many types of samples, such as other tissues of the body and non-tissue material. While reference is made to generating maps of retinal thickness, the methods and apparatus disclosed herein can be used to generate images of retinal samples, such as cross sectional or tomographic images.

The presently disclosed systems, methods and apparatuses are well suited for combination with prior images and imaging systems, such as OCT imaging systems and OCT images, in order to provide improved classification of image structure, such as tissue type, fluid pooling, etc. In some embodiments, transfer learning is used, in which an artificial intelligence model, e.g. a neural network, trained in a first setting is used to improve performance in a second setting. In some embodiments, the first setting comprises a first OCT system configuration comprising a first resolution and a second OCT system configuration, in which the first OCT system configuration comprises a greater resolution (e.g. resolves smaller image details) than the second OCT system configuration. The transfer learning can be configured in many ways in accordance with the present disclosure. In some embodiments, the coefficients of the neural network are generated by training the neural network on the first data set from the first setting and the learned parameters are then transferred to the second setting, e.g. parameters generated from data from the first OCT system configuration are applied to data from the second OCT system configuration to analyze data from the second OCT system configuration. Alternatively or in combination, the transfer learning may comprise curriculum learning, in which images of increasing difficulty are used to train the neural network. In some embodiments, images from the first setting corresponding to the first OCT system configuration are progressively degenerated and used to train the neural network until the image quality, e.g. resolution, corresponds to images from the second setting corresponding to the second OCT system.

An examples of a suitable higher resolution system includes the Spectralis® OCT System commercially available from Heidelberg engineering. An example of a suitable personal biometry system (PBOS) having a lower resolution OCT imaging system is described in U.S. Pat. No. 10,610,096, granted on Apr. 4, 2020, entitled "MINIATURIZED MOBILE, LOW COST OPTICAL COHERENCE TOMOGRAPHY SYSTEM FOR HOME BASED OPHTHALMIC APPLICATIONS", the full disclosure of which is incorporated herein by reference. The higher resolution OCT system may comprise an axial resolution within a range from about 1 micrometer (um) to about 10 um, and the lower resolution OCT system may comprise an axial resolution within a range from about 15 um to about 50 um, for example. Although reference is made to these resolution ranges, in some embodiments, the lower resolution system comprises an axial resolution within the range of about 1 um to about 10 um, and the higher resolution comprises a resolution within this range or an even smaller axial resolution, e.g. less than 1 um.

In some embodiments, the systems, apparatuses, and methods described by this disclosure are directed to identifying structures, regions, or features of images obtained from an OCT system. In some embodiments, this identification may be performed by a trained model, which may take the form of a neural network. The neural network may be configured or operate to process an input image and output a segmented image or data that indicates the probability of each pixel in the input belonging to a specific class (i.e., the relative probabilities between two classes), with the result being that an image is created that maps each pixel to a specific class. In some embodiments, the class may be one of a structure, layer, boundary, feature, or pool of fluid in a retina, for example.

The techniques and methods described herein may be used to perform one of several tasks or objectives. These include inputting an image obtained from an OCT system into a trained model and in response outputting a segmented image identifying one or more regions, layers, boundaries, feature, pools of fluid, etc. Another task is one of identifying a change or progression in a region, layer, boundary, feature, pool of fluid, etc. Yet another task is to compare images produced by two different OCT systems to validate the accuracy of one of the systems or to use images obtained from a second OCT system to determine changes in any regions, etc. identified in the images from the first OCT system, where the two OCT systems may have different resolutions or may employ different scan patterns when collecting image data.

For each of the described tasks a trained model may be developed to perform the task. In some embodiments, training a model to perform a task involves applying a machine learning algorithm to a set of data and annotations. The annotations segment an image pixel-wise into two or more classes and are typically provided by a human being who is familiar with the subject matter of the images. The machine learning algorithm "learns" the correct label or segmentation to apply to a pixel from the data and annotations and generates a model in the form of a neural network.

However, training a model to obtain a desired level of performance (i.e., a desired level of precision and recall, sometimes expressed as a specific measure) may require more training data than is available. For example, there may be sufficient data available from a first type of OCT system, or an OCT system with a specific resolution or scan pattern to train a model, but not enough from a second type of OCT system that is used to generate images that a user would like segmented. As another example, annotations of data from the first device may be more easily or readily available than annotations of data from the second device. In these situations, it would be beneficial to be able to train a model using image data obtained from the first type of OCT system and then use the trained model to classify image data generated by the second type of OCT system. As mentioned, examples of this situation occur if the two OCT systems have different resolutions or employ different scan patterns when collecting image data.

Embodiments comprise data acquisition and processing flows that may be used to produce a trained model for use in image segmentation in a situation where there is a lack of sufficient training data. In such cases, the (un)availability of sufficient training data may preclude training a model using the same type of data as generated by a desired OCT system. In such situations, the techniques and methods disclosed enable the generation of new training data (and in some cases annotations or labels) that may be used in addition to, or as a replacement for, data obtained from a first OCT system when training a model to perform segmentation of images obtained from a second OCT system. In some embodiments, the training data may be from a system with a different (typically higher) resolution, and in some embodiments, the training data may be from a system implementing a different scan pattern than the system producing the images to be segmented.

In some embodiments, the potential problems or obstacles caused by insufficient training data may be overcome by use of one or more data processing techniques described herein. These techniques include: (1) Augmentation—these techniques may be used to generate additional training data by applying one or more operations (e.g., geometrical transformations, such as those illustrated in FIG. 8) to a set of data associated with an image (and also in some cases to the associated annotations of retinal layers, fluid regions, etc.) to provide increased data variability for the machine learning algorithm, increase the robustness of the model, and prevent over-fitting of the model to the data. In some cases, the geometrical transformations may also be applied to annotations; (2) Degeneration—these techniques are applied to original image data obtained from a OCT system with higher resolution to obtain data that would be expected to be obtained from an OCT system with lower resolution; (3) Resampling—this technique is applied to image data obtained using a first scan pattern to generate image data expected to be obtained using a second and different scan pattern (such as is typically produced by a different OCT system); and (4) Registering or registration—this technique is a way to align annotations or indications of features (boundaries, regions, fluid, etc.) in a second set of OCT images obtained by degenerating a first set of images so that the annotations are correctly associated with the features identified in the first set of OCT images.

Embodiments of the system, apparatuses, and methods described by this disclosure are directed to the training and use of a model to perform the segmentation of images obtained from an OCT device. In some embodiments, the model is a neural network, such as a convolutional neural network that may be used for image processing. The output of the trained neural network is a segmentation of an input image, where the segmentation operation identifies one or more elements, layers, regions, structures, boundaries, pools of fluid, or other features of a retina that was imaged by the OCT.

As mentioned, one of the difficulties in developing such a model is that it requires reliable training data. This problem is made more complicated because different OCT systems that might be used to generate training data images may have different characteristics, where these characteristics may include scan pattern, axial resolution, lateral resolution, or method of alignment. These differences make it that much more difficult to obtain sufficient training data for a model, and also make it difficult to compare images obtained using OCT systems with different characteristics or to reliably segment an image obtained using one type of OCT system using a model trained on data obtained from a second and different type of OCT system.

FIG. 1 shows a simplified diagram of the human eye. Light enters the eye through the cornea 10. The iris 20 controls the amount of light allowed to pass by varying the size of the pupil 25 that allows light to proceed to the lens 30. The anterior chamber 40 contains aqueous humor 45 which determines the intraocular pressure (TOP). The lens 30 focuses light for imaging. The focal properties of the lens are controlled by muscles which reshape the lens. Focused light passes through the vitreous chamber, which is filled with vitreous humor 55. The vitreous humor maintains the overall shape and structure of the eye. Light then falls upon the retina 60, which has photosensitive regions. In particular, the macula 65 is the area of the retina responsible for receiving light in the center of the visual plane. Within the macula, the fovea 70 is the area of the retina most sensitive to light. Light falling on the retina generates electrical signals which are passed to the optic nerve 80 and then to the brain for processing.

Several disorders give rise to reduced optical performance of the eye. In some cases, the intraocular pressure (IOP) is either too high or too low. This is caused, for instance, by too high or too low of a production rate of aqueous humor in the anterior chamber or drainage of aqueous humor from the anterior chamber, for example. In other cases, the retina is too thin or too thick. This arises, for instance, due to the buildup of fluid in the retina. Diseases related to an abnormal retinal thickness (RT) include glaucoma, macular degeneration, diabetic retinopathy, macular edema and diabetic macular edema, for example. In some cases, a healthy range of RT is from 175 μm thick to 225 μm thick. In general, abnormalities in either the IOP or the RT or both are indicative of the possible presence of one of several ophthalmological diseases. Additionally, the IOP or the RT vary in response to ophthalmological treatments or other procedures. Therefore, it is desirable to have a means to measure the IOP and/or RT for diagnosis of ophthalmological diseases and to assess the effectiveness of treatments for a given patient. In some cases, it is desirable to measure the thickness of one or more retinal layers, for example the thickness of a plurality of layers. In addition, it is desirable to process data obtained from an OCT system to assist in identifying fluid pockets or regions in the eye, as these may indicate a change in eye health.

As described, the disclosed OCT system may include a scanner that can be controlled to cause a measurement beam to move in a scan pattern on a patient's retina. The scan pattern may be one of various types, including a stop and go scan pattern, a star scan pattern, a continuous scan pattern, a Lissajous scan pattern, or a flower pattern, sometimes referred to as a rose curve. As will be described in further detail, the flower pattern or rose curve may be used to generate measurement data that can be processed to generate data that represents data that would be obtained from a different scan pattern. Further, the flower pattern or rose curve may be used to generate measurement data that can be processed to generate interferometric data that can be used as an input to a trained CNN to provide a segmentation of the layers of the retina.

Figure 2A:
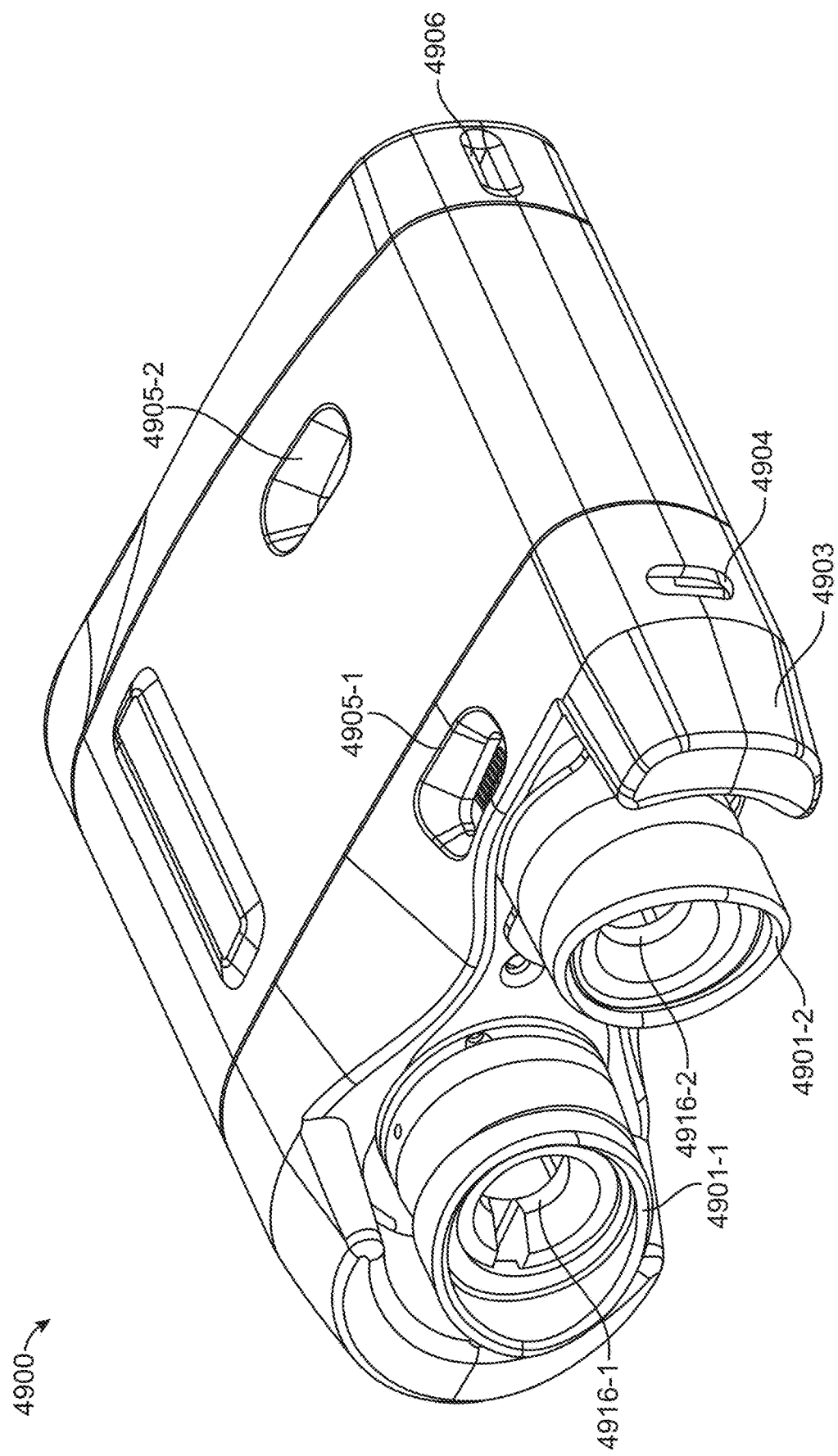
FIG. 2A shows a perspective view of a binocular OCT device for measuring eyes of a user, in accordance with some embodiments.

FIG. 2A shows a perspective view of a binocular OCT device 4900 for measuring eyes of a user, in accordance with some embodiments. The binocular OCT device 4900 comprises a first adjustable lens 4916-1 that is optically coupled to an OCT measurement system and a first fixation target configured within a handheld unit body 4903 (e.g., a housing), both of which are hidden from view in this figure. Similarly, a second adjustable lens 4916-2 may be optically coupled to the OCT measurement system and a second fixation target (hidden). The first adjustable lens 4916-1 may be part of a first free space optics that is configured to provide a fixation target and measure a retinal thickness of the user's eye, whereas the second adjustable lens 4916-2 may be part of a second free space optics that is configured to only provide a fixation target so as to reduce a number of components in the binoculars OCT device 4900. For instance, while both free space optics provide the user with a fixation target, only one of the free space optics is used to measure the retinal thickness as the binocular OCT device 4900 may be turned upside down, i.e. inverted, after the user measures a first eye such that the user may measure the other eye.

The binocular OCT device 4900, in this embodiment, comprises an interpupillary distance (IPD) adjustment mechanism 4905 that is accessible on the exterior of the handheld unit body 4903. In this embodiment, the IPD adjustment mechanism 4905 comprises two components, a first component 4905-1 that adjusts the distance between the lenses 4916-1 and 4916-2 to match the IPD of a user's pupils when the user places the binocular OCT device 4900 front of the user's eyes when the eye cups 4901-1 and 4901-2 rest on the user's face.

This IPD can be set by a healthcare professional and locked into position for the user to measure retinal thickness at home. Alternatively, the IPD can be user adjustable. A switch (or other method of adjustment, such as a screw or dial) 4904 may be used to adjust the lenses 4916-1 and 4916-2 to match a user's refraction, i.e. eyeglass prescription. Alternatively, a mobile device, such as a tablet can be used program the refraction of each eye of the patient. For example, the user may fixate on the first fixation target with one eye and a second fixation target with another eye, and the movable lenses adjusted to the user's refraction. The switch 4904 may selectively adjust the assemblies of the lenses 4916-1 and 4916-2 within the handheld unit body 4903 to change the positioning of the lenses 4916-1 and 4916-2. These positions can be input into the device by a health care professional and stored in a processor along with an orientation from an orientation sensor as described herein. The device can be inverted, and the process repeated. Alternatively, or additionally, the prescription for each eye can be stored in the processor and the lenses adjusted to the appropriate refraction for each eye in response to the orientation of the orientation sensor.

Both of the components 4905-1 and 4905-5 may be implemented as one or more wheels that the health care professional manually rotates. Alternatively, the IPD adjustment mechanism 4905 may be motorized. In this regard, the components 4905-1 and 4905-5 may be configured as directional switches that actuate motors within the handheld unit body 4903 to rotate gears within the handheld unit body 4903 based on the direction in which the user directs the switch.

The switch 4904 can be used to adjust the focusing of the binocular OCT device 4900. For example, because the focal change effected by adjustment of the lenses 4916-1 and 4916-2 can be measured in a customary unit of refractive power (e.g., the Diopter) by adjustment of the lenses 4916-1 and 4916-2. The Diopter switch 4906 may also comprise a directional switch that actuates a motor within the handheld unit body 4903 to rotate gears within the handheld unit body 4903 based on the direction in which the healthcare professional directs the switch to adjust the refractive power of the binocular OCT device 4900. As the binocular OCT device 4900 may comprise an electronic device, the binocular OCT device 4900 may comprise a power switch 4906 to control powering of the binocular OCT device 4900.

Each of the eyecups 4901-1 and 4901-2 can be threadedly mounted and coupled to the housing to allow adjustment of the position of the eye during measurements. Work in relation to the present disclosure suggests that the eyecups can be adjusted by a healthcare professional and locked in place to allow sufficiently reproducible positioning of the eye for retinal thickness measurements as described herein. Alternatively, or in combination, an eye position sensor, such as a Purkinje image sensor can be used to determine a distance from the eye to the OCT measurement system.

The binocular OCT device 4900 may comprise appropriate dimensions and weight for in home measurements and for the user to take the binocular OCT system on trips. For example, the binocular OCT system may comprise a suitable length, a suitable width and a suitable height. The length can extend along an axis corresponding to the users viewing direction. The length can be within a range from about 90 mm to about 150 mm, for example about 130 mm. The width can extend laterally to the length and can be within a range from about 90 mm to about 150 mm for example about 130 mm. The height can be within a range from about 20 mm to about 50 mm, for example. In some embodiments, the length is within a range from about 110 mm to 210 mm, the width within a range from about 100 mm to 200 mm and a height within a range from about 50 mm to about 110 mm. In some embodiments, a maximum distance across the device is within a range from about 200 mm to about 350 mm, for example approximately 300 mm.

The weight of the binocular OCT system can be within a range from about 1 pound to two pounds, e.g. 0.5 kg to about 1 kg.

The binocular OCT device 4900 can be configured to be dropped and still function properly. For example, the binocular OCT device can be configured to be dropped from a height of about 30 cm and still function so as to perform retinal thickness measurements accurately, e.g. with a change in measured retinal thickness of no more than the repeatability of the measurements. The binocular OCT system can be configured to be dropped from a height of about 1 meter without presenting a safety hazard, for example from glass breaking.

Figure 2B:
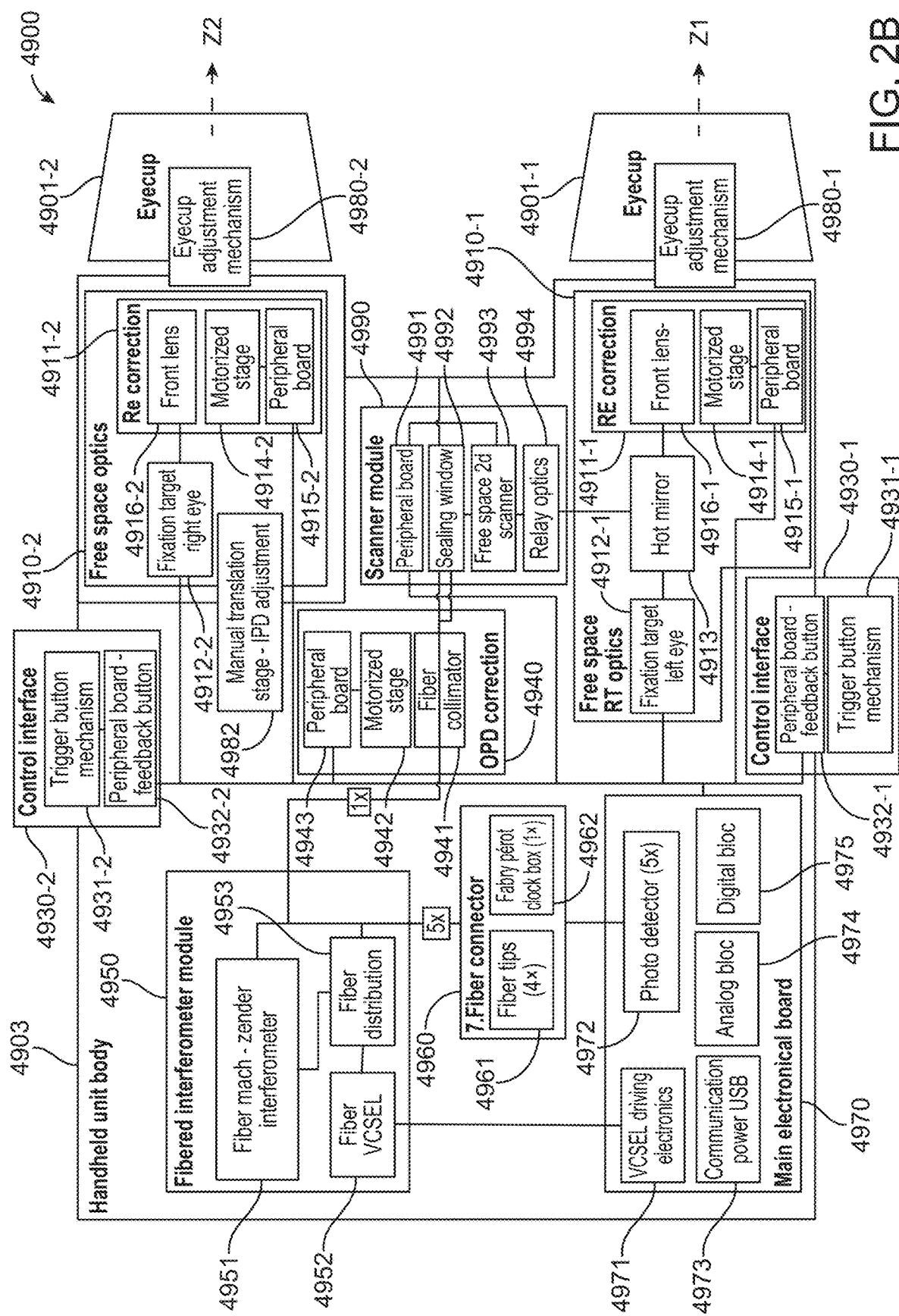
FIG. 2B shows a block diagram of the binocular OCT device illustrating various components within the handheld unit body, in accordance with some embodiments.

FIG. 2B shows a block diagram of the binocular OCT device 4900 illustrating various components within the handheld unit body 4903, in accordance with some embodiments. For instance, the binocular OCT device 4900 comprises free space optics 4910-1 and 4910-2. Each of the free space optics 4910-1 and 4910-2 comprises a fixation target 4912 for its respective eye that allows the user to fixate/gaze on the target while the user's retinal thickness is being measured, and to allow fixation with the other eye, so as to provide binocular fixation. The fixation target may comprise an aperture back illuminated with a light source such as an LED, (e.g., a circular aperture to form a disc shaped illumination target, although a cross or other suitable fixation stimulus may be used. The free space optics 4910-1 and 4910-2 may also comprise refractive error (RE) correction modules 4911-1 and 4911-2, respectively, that comprises the lenses 4916-1 and 4916-2, respectively. These lenses can be moved to preprogrammed positions corresponding to the refractive error of the appropriate eye. A peripheral board 4915-1 and 4915-2 in the free space optics modules 4910-1 and 4910-2 provides electronic control over a motorized stage 4914-1 and 4914-2, respectively to correct for the refractive error of the respective eye viewing the fixation target of the binocular OCT device 4900.

As discussed herein, the binocular OCT device 4900 may comprise eye cups 4901-1 and 4901-2 that may be used to comfortably rest the binocular OCT device 4900 on the user's face. They may also be configured to block out external light as the user gazes into the binocular OCT device 4900. The eye cups 4901 may also comprise eye cup adjustment mechanisms 4980-1 and 4980-2 that allow the health care professional and optionally the user to move the eye cups 4901-1 and 4901-2 back and forth with respect to the handheld unit body 4903 to comfortably position the eye cups on the user's face and appropriately position each eye for measurement.

In some embodiments, the binocular OCT device 4900 comprises a fibered interferometer module 4950 that comprises a single VCSEL or a plurality of VCSELs 4952. The one or more VCSELs 4952 are optically coupled to a fiber distribution module 4953, which is optically coupled to fiber Mach-Zehnder interferometer 4951. With embodiments comprising a plurality of VCSELs 4952, the VCSELS may each comprise a range of wavelengths different from other VCSEL 4952 in the plurality in order to extend a spectral range of light. For example, each VCSEL 4952 may pulse laser light that is swept over a range of wavelengths for some duration of time. The swept range of each VCSEL 4952 may partially overlap an adjacent swept range of another VCSEL 4952 in the plurality as described herein. Thus, the overall swept range of wavelengths of the plurality of VCSELs 4952 may be extended to a larger wavelength sweep range. Additionally, the firing of the laser light from the plurality of VCSELs 4952 may be sequential. For example, a first VCSEL of the plurality of VCSELs 4952 may sweep a laser pulse over a first wavelength for some duration. Then, a second VCSEL of the plurality of VCSELs 4952 may sweep a laser pulse over a second wavelength for some similar duration, then a third, and so on.

The laser light from the VCSELs 4952 is optically transferred to the fiber distribution module 4953, where a portion of the laser light is optically transferred to a fiber connector 4960 for analysis in a main electronic board 4970. The fiber connector 4960 may connect a plurality of optical fibers from the fiber distribution module 4953 to the fiber connector module 4960. Another portion of the laser light is optically transferred to an optical path distance correction (OPD) module 4940 and ultimately to the free space retinal thickness optics 4910-1 for delivery to a user's eye and measurement of the user's eye with a portion of the measurement arm of the Mach-Zehnder interferometer. For example, the OPD correction module 4940 may comprise a peripheral board 4943 that is controlled by the main electronic board 4970 to actuate a motorized stage 4942 to change the optical path distance between the user's eye, a coupler of the Mach-Zehnder interferometer and the one or more VCSELs 4952. The OPD correction module 4940 may also comprise a fiber collimator 4941 that collimates the laser light from the VCSELs 4952 before delivery to the user's eye, and the fiber collimator can be translated with the OPD correction module 4940.

A controller interface 4930 may be used to receive user inputs to control the binocular OCT measurement system. The controller interface may comprise a first controller interface 4930-1 and a second controller interface 4930-2. The controller interface 4930 may comprise a trigger button mechanism that allows a user to initiate a sequence of steps to align the eye and measure the retina as described herein. Alternatively, or in combination, the device may be configured with an auto-capture function, such that the data is automatically acquired when the device is aligned to the eye within appropriate tolerances.

Additionally, the binocular OCT device 4900 may comprise a scanner module 4990 that scans the laser light from the one or more VCSELs 4952 in a pattern (e.g., a stop and go scan pattern, a star scan pattern, a continuous scan pattern, a Lissajous scan pattern, or a flower scan pattern (rose curve)). For example, a peripheral board 4991 of the scanner module 4990 may be communicatively coupled to the main electronic board 4970 to receive control signals that direct the scanner module 4992 to scan the pulsed laser light from the VCSELs 4952 in a pattern to perform an optical coherence tomography (OCT) on the user's eye. The scanning module 4990 may comprise a sealing window 4992 that receives the laser light from the fiber collimator 4941 and optically transfers the laser light to a free space two-dimensional scanner 4993, which provides the scan pattern of the laser light. The two-dimensional scanner may comprise a scanner as described herein, such as a two-axis galvanometer, or a two axis electro-static scanner, for example. When present, the sealing window 4992 may be used to keep the internal components of the binocular OCT device 4900 free of dirt and/or moisture. The laser light is then optically transferred to relay optics 4994 such that the scanned laser light can be input to the user's eye via the free space RT optics 4910-1. In this regard, the scanned laser light may be transferred to a hot mirror 4913 such that infrared light may be reflected back towards the hot mirror, the scanning mirror and focused into an optical fiber tip coupled to the collimation lens. The hot mirror 4913 generally transmits visible light and reflects infrared light, and may comprise a dichroic short pass mirror, for example.

The scanner and associated optics can be configured to scan any suitably sized region of the retina, such as regions comprising the fovea. In some embodiments, the scanner is configured to scan the retina with a scanning pattern, such as a predetermined scanning pattern in response to instructions stored on a processor such as the controller. For example, the scanner can be configured to scan the retina over an area comprising a maximum distance across within a range from about 1.5 to 3 mm, for example. The scanning region of the retina may comprise an area larger than maps of retinal thickness in order to account for slight errors in alignment, e.g. up to 0.5 mm in the lateral positioning of the eye in relation to the OCT system, for example in order to compensate for alignment errors, e.g. by aligning the map based on the measured position of the eye. The size of the OCT measurement beam on the retina can be within a range from about 25 microns to about 75 microns. In some embodiments, the mirror is moved with a continuous trajectory corresponding to a scan rate on the retina within a range from about 10 mm per second to about 200 mm per second, and the scan rate can be within a range from about 50 mm per second to about 200 mm per second. The displacement of the beam during an A-scan can be within a range from about 2 to 10 microns, for example. The beams for each of a plurality of A-scans can overlap. In some embodiments, the mirror moves continuously with one or more rotations corresponding to the trajectory of the scan pattern and the swept source VCSEL turns on and off with a suitable frequency in relation to the size of the beam and the velocity of the beam on the retina. In some embodiments each of the plurality of A-scans overlaps on the retina during at least a portion of the scan pattern.

In embodiments where the one or more VCSELs comprises a plurality of VCSELs, the plurality of VCSELs can be sequentially scanned for each A-scan, such that the measurement beams from each of the plurality of VCSELs overlaps on the retina with a prior scan. For example, each of the sequentially generated beams from each of the plurality of VCSELs from a first A-scan can overlap with each of the sequentially generated beams from each of the plurality of VCSELs from a second A-scan along the trajectory.

As described herein, the binocular OCT device 4900 may comprise an IPD adjustment via the components 4905-1 and/or 4905-2. These components may be communicatively coupled to a manual translation stage IP adjustment module 4982 that perform the actuation of the free space optics modules 4910-1 and 4910-2, so as to change a separation distance between the free space optics modules and adjust the IPD.

The main electronic board 4970 may comprise a variety of components. For example, a photodetector 4972 may be used to receive laser light directed from the VCSELs 4952 through the fiber connector 4960 as well interfering light reflected from the user's eye. The fiber connector 4960 may comprise a module 4961 that couples a plurality of optical fibers, for example four optical fibers, to a plurality of detectors, for example five detectors. The fiber connector 4960 may also comprise an interferometer clock box 4962 (e.g. an etalon) that may be used in phase wrapping light reflected back from the user's eyes, as shown and described herein. Once received by the photodetectors 4972, the photodetectors 4972 may convert the light into electronic signals to be processed on the main electronic board 4970 and/or another processing device. The plurality of photo detectors may comprise two detectors of a balanced detector pair coupled to the fiber Mach-Zehnder interferometer, a clock box detector, and a pair of power measurement detectors, for example.

The main electronic board 4970 may comprise a communication power module 4973 (e.g., a Universal Serial Bus, or "USB") that can communicatively couple the binocular OCT device 4900 to another processing system, provide power to the binocular OCT device 4900, and/or charge a battery of the binoculars OCT device 4900. Of course, the binocular OCT device 4900 may comprise other modules that may be used to communicate information from the binocular OCT device 4900 to another device, including for example, Wi-Fi, Bluetooth, ethernet, FireWire, etc.

The main electronic board 4970 may also comprise VCSEL driving electronics 4971 which direct how and when the VCSELs 4952 are to be fired towards the user's eyes. Other components on the main electronic board 4970 comprise an analog block 4974 and a digital block 4975 which may be used to process and/or generate analog and digital signals, respectively, being transmitted to the binocular OCT device 4900 (e.g., from an external processing system), being received from various components within the binocular OCT device 4900, and/or being received from various components within the binocular OCT device 4900. For example, the peripheral feedback button 4932 may generate an analog signal that is processed by the analog block 4974 and/or digital clock 4975, which may in turn generate a control signal that is used to stimulate the motorized stage module 4942 via the peripheral board 4943. Alternatively, or additionally, the analog block 4974 may process analog signals from the photodetectors 4972 such that they may be converted to digital signals by the digital block 4975 for subsequent digital signal processing (e.g., FFTs, phase wrapping analysis, etc.).

Figure 2C:
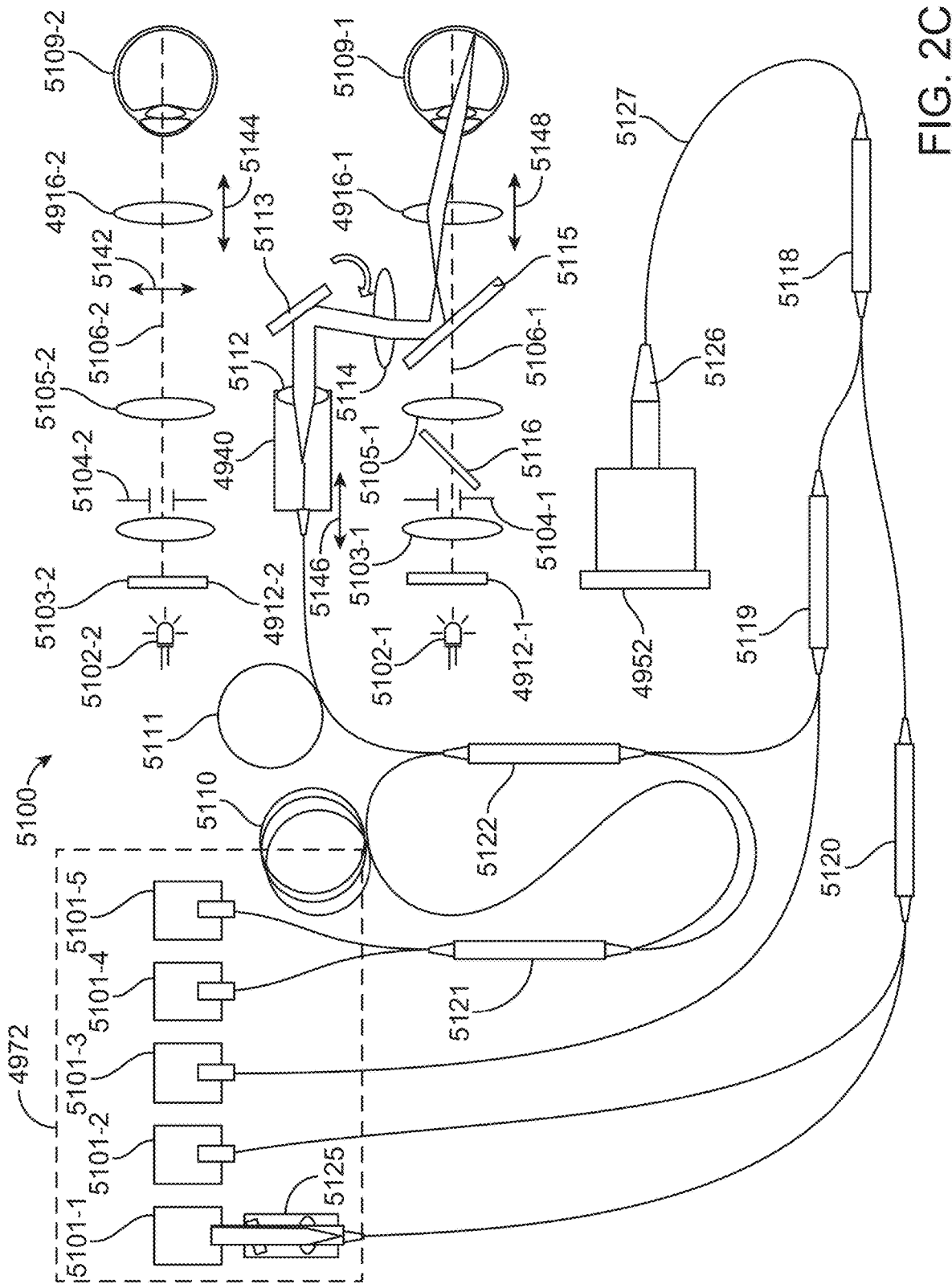
FIG. 2C shows a schematic of an optical configuration that may be implemented with the OCT binocular, in accordance with some embodiments.

FIG. 2C shows a schematic of an optical configuration 5100 that may be implemented with the OCT binocular 4900, in accordance with some embodiments. The optical configuration 5100 comprises one or more VCSELs 4952 that are fiber coupled via an optical coupler 5126. As discussed above, the one or more VCSELs 4952 may be swept over a range of wavelengths when fired. For embodiments with a plurality of VCSELs 4952, the wavelengths may partially overlap a wavelength sweep range of another VCSEL 4952 in the plurality so as to increase in overall sweep range of the VCSELs 4952. In some instances, this overall sweep range is centered around approximately 850 nm. The laser light from the one or more VCSELs 4952 is propagated through the fiber coupler 5126 to a fiber optic line 5127, where another optical coupler 5118 splits a portion of the optical energy from the one or more VCSELs 4952 along two different paths.

In the first path, approximately 95% of the optical energy is optically transferred to another optical coupler 5119 with approximately 5% of the optical energy being optically transferred to an optical coupler 5120. In the second path, the optical energy is split yet again via an optical coupler 5120. In this regard, approximately 75% of the optical energy from the optical coupler 5120 is transferred to a phase correction detector 5101-1 through an interferometer such as a Fabry Perot interferometer comprising an etalon. The etalon and detector may comprise components of an optical clock 5125. The optical clock 5125 may comprise a single etalon, for example. The etalon may comprise substantially parallel flat surfaces and be tilted with respect to a propagation direction of the laser beam. The surfaces may comprise coated or uncoated surfaces. The material may comprise any suitable light transmissive material with a suitable thickness. For example, the etalon may comprise a thickness within a range from about 0.25 mm to about 5 mm, for example within a range from about 0.5 mm to about 4 mm. The reflectance of the etalon surfaces can be within a range from about 3% to about 10%. The etalon can be tilted with respect to the laser beam propagation direction, for example tilted at an angle within a range from about 5 degrees to about 12 degrees. The finesse of the etalon can be within a range from about 0.5 to about 2.0, for example, for example within a range from about 0.5 to 1.0. The etalon may comprise any suitable material such as an optical glass. The thickness, index of refraction, reflectance and tilt angle of the etalon can be configured to provide a substantially sinusoidal optical signal at the clock box detector. The finesse within the range from about 0.5 to 2.0 can provide substantially sinusoidal detector signals that are well suited for phase compensation as described herein, although embodiments with higher finesse values can be effectively utilized.

In some embodiments, the clockbox may comprise a plurality of etalons. The approach can be helpful in embodiments wherein the one or more VCSELs comprises a plurality of VCSELs, and the plurality of etalons provides additional phase and clock signal information. For example, the clockbox may comprise a first etalon and a second etalon arranged so that light is transmitted sequentially through the first etalon and then the second etalon, e.g. a series configuration, which can provide frequency mixing of the clock box signals and decrease the number of detectors and associated circuitry used to measure phase of the swept source. Alternatively, the plurality of etalons can be arranged in a parallel configuration with a plurality of etalons coupled to a plurality of detectors.

The phase correction detector 5101-1 may use the light signals from the optical clock 5125 to correct the phase of light reflected from a user's eyes 5109-1 by matching the phases of the one or VCSELs 4952 via phase wrapping of the light from the one or more VCSELs 4952 as described herein. The remaining 25% of the optical energy from the optical coupler 5120 may be optically transferred to a detector 5101-2 for optical safety. For instance, the detector 5101-2 may be used to determine how much optical energy is being transferred to the user's eye 5109-1 or 5109-2, depending on the orientation of the device. If the binocular OCT device 4900 determines that the detector 5101-2 is receiving too much optical energy that may damage the user's eyes, then the binocular OCT device 4900 may operate as a "kill switch" that shuts down the VCSELs 4952. Alternatively, or additionally, the binocular OCT device 4900 may monitor the detector 5101-2 to increase or decrease the optical energy from the VCSELs 4952 as deemed necessary for laser safety and/or signal processing. The OCT device may comprise a second safety detector 5101-3 to provide a redundant measurement for improved eye safety.

The optical energy transferred to the optical coupler 5119 (e.g., approximately 95% of the optical energy from the one or more VCSELs 4952) is also split along two paths with approximately 99% of the remaining optical energy being optically transferred along a fiber to an optical coupling element 5122 and with approximately 1% of the remaining optical energy also being optically transferred to a detector 5101-3 for laser safety of the binocular OCT device 4900. The portion of the optical energy transferred to the to the optical coupler 5122 may be split by the optical coupler 5122 between two optical path loops 5110 and 5111 of the Mach-Zehnder interferometer, approximately 50% each, for example. The optical path loop 5110 may comprise a reference arm of the interferometer and provide a reference optical signal for the retinal thickness measurement of the user's eye 5109-1 (e.g., the measurement signal reflected from the user's retina through the optical path loop 5111).

The portion of the optical energy transferred through the optical loop 5111 is transferred to the user's left eye 5109-1 along the measurement arm of the Mach-Zehnder interferometer. For instance, the optical energy being transferred to the user's eye 5109-1 may pass through the OPD correction module 4940 to perform any optical path distance corrections appropriate to the interferometer of the binocular OCT device 4900. This light may then be scanned across the user's eye 5109-1 via a scanning mirror 5113 of the scanner module 4990 to measure the retinal thickness of the user's eye 5109-1 while the user's eye 5109-1 is fixated on a fixation target 4912-1 (e.g., along a fixation path 5106-1).

The fixation target 4912-1 can be back illuminated with LED 5102-1, and light may be propagated along the optical path 5106-1 through optical elements 5103-1 and 5105-1 and the dichroic mirror 5115, comprising a hot mirror. In some instances, the target of fixation may also include an illumination stop 5104 so as to provide relief to the user's eye 5109-1 while fixating on the target.

The light impinging the user's retina of the eye 5109-1 may be reflected back along the path established by the OPD correction module 4940, the scanning mirror 5113, the focusing element 5114, the dichroic mirror 5115, and the optical element 4916-1, through the optical loop 5111, and back to the optical coupler 5122. In this instance, the optical coupler 5122 may optically transfer the reflected optical energy to an optical coupler 5121 which may couple the reflected optical energy with the optical energy that was split into the optical loop 5110. The optical coupler 5121 may then optically transfer that optical energy to the balanced detector's 5101-4 and 5101-5 such that a retinal thickness measurement can be performed. In doing so, the optical coupler 5121 may split that optical energy to approximately 50% to each of the detectors 5101-1 and 5101-4, such that the interference signals arrive out of phase on the balanced detectors.

The light may be focused through a plurality of optical elements 5112 and 5114, being directed to the user's eye 5109-1 via a dichroic mirror 5115 and focused on the user's retina via the optical element 4916-1. The light from the scanning mirror 5113 and the light reflected from the user's eye 5109 are both shown as reflecting off the dichroic mirror 5115, which may comprise hot mirror 4913 configured to generally reflect infrared light and transmit visible light.

As can be seen in this example, the user's right eye 5109-2 does not receive any optical energy from the one or more VCSELs 4972 with the orientation shown. Rather, the user's right eye 5109-2 is used for binocular fixation with the target 4912-2, which can be back illuminated with another LED 5102-2. The target 4912-2 can be of similar size and shape to target 4912-1 and be presented to the eye with similar optics, so as to provide binuclear fixation. In this regard, the user's right eye 5109-2 may also fixate on the target 4912-2 along an optical path 5106-2 through the optical elements 4916-2, 5105-2, 5103-2, and the illumination stop 5104-2, which comprises similar optical power, separation distances and dimensions to the optics along optical path 5106-1.

The binocular OCT system 4900 can be configured to move optical components to a customized configuration for the user being measured. Lens 4916-1 can be adjusted along optical path 5106-1 in accordance with the refraction, e.g. eyeglass prescription of the eye being measured. Lens 4916-1 can be moved under computer, user or other control to adjust lens 4916-1 to bring the fixation target 4912-1 into focus and to focus the measurement beam of the OCT interferometer on the user's retina. For example, the lens can be translated as shown with arrow 5146. Lens 4916-2 can be moved under computer, user or other control to adjust lens 4916-2 to bring the fixation target 4912-2 into focus on the user's retina. For example, the lens can be translated as shown with arrow 5144. The OPD correction module 4940 can be translated axially toward and away from mirror 5113 as shown with arrows 5146. The OPD correction module 4940 can be moved under computer control to appropriately position the optical path difference between the measurement arm and the reference arm for the user's eye being measured. The interpupillary distance can be adjusted by translating the optical path 5106-2 toward and away from optical path 5106-1.

The free space optics module 4910-2 may comprise one or more components along optical path 5106-2, such as the LED 5101-2, the fixation target 4912-2, lens 5103-2, aperture 5104-2, lens 5105-2, or lens 4916-2. The free space optics module 4910-2 can be translated laterally toward and away from the optical components located along optical path 5106-1 to adjust the inter pupillary distance as shown with arrow 5142. The free space retinal thickness optics module 4910-1 may comprise one or more components located along optical path 5106-1, such as the LED 5102-1, the fixation target 5103-1, the aperture 5104-1, the mirror 5116, the lens 5105-1, the mirror 5115, or lens 4916-1. The OPD correction module 5146 may comprise the optical fiber of the measurement arm of the interferometer, and lens 5112 to substantially collimate light from the optical fiber and to focus light from the retina into the optical fiber.

In some embodiments, an A-scan represents a depth reflectivity profile of a sample and may result from performing a Fourier Transform on a detected interferogram that is obtained while varying the wavelength of the light source such as a VCSEL, as described herein. In some embodiments, a B-scan comprises a 2D image corresponding to a slice of tissue along a plane. In some embodiments, a B-scan image is generated by scanning the measurement beam along a sample in a linear scan pattern, where the B-scan comprises a plurality of A-scans along the scan pattern. In some embodiments, each of the plurality of A-scans used to form the B-scan represents interferometric data collected at a measurement location or point along the scan pattern. Alternatively, or in combination, a B-scan can be generated from a non-linear scan pattern so as to represent a slice of tissue along a linear section of tissue, for example with one or more interpolation or mapping of the non-linear scan pattern as described herein.

Figure 3:
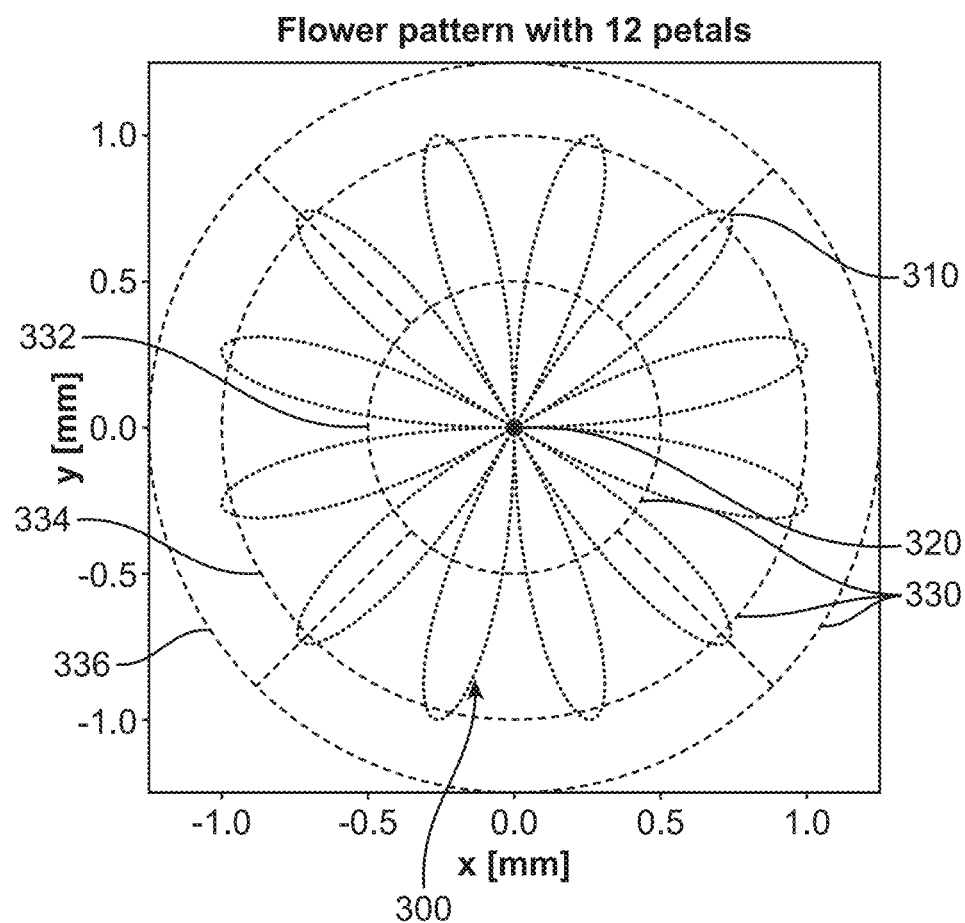
FIG. 3 shows an example of a scan pattern (termed a "flower" pattern herein) that may be used to collect OCT data, in accordance with some embodiments.

As described, an OCT system operates to move a measurement beam of light on a retina in a specific scan pattern. This scan pattern may take several different forms, including but not limited to a stop and go scan pattern, a star scan pattern, a continuous scan pattern, a linear scan pattern, a Lissajous scan pattern, or a flower scan pattern. FIG. 3 shows an example of a scan pattern (termed a "flower" scan pattern herein) that may be used to collect OCT data, in accordance with some embodiments. The scan pattern 300 shown in the figure is also referred to as a rose curve, where a rose curve is a polar coordinate representation of a sinusoid. The flower scan pattern 300 comprises a plurality of lobes 310 or petals, with one end of each lobe being connected to and extending radially outward from a central point or location 320. The flower pattern shown in the figure has 12 lobes or petals, although a different number may be present in a scan pattern.

The figure shows a superposition of the scan pattern on a patient's eye and indicates several regions of tissue of the eye, such as the retinal tissue. The three concentric rings or annular regions 330 (shown by dashed lines) in the figure represent different zones or regions of a retina of a patient's eye. In some embodiments, the innermost ring 332 represents at least a portion of the fovea region of a patient's eye, the middle ring 334 represents the macular region of a patient's eye, and the outermost ring 336 represents a region outside the fovea. The sector or region in between the innermost ring 332 and the middle ring 334 is divided into 4 zones in the figure. Similarly, the sector or region in between the middle ring 334 and the outermost ring 336 is divided into 4 zones in the figure. In some embodiments, the plurality of zones comprises a total of 9 identified zones or regions of a patient's retina. In some embodiments, the innermost ring has a diameter of about 1 mm and contains the fovea, which may have a diameter of about 0.35 mm. In some embodiments, the middle ring has a diameter of about 2 mm and contains the macula, which may have a diameter of about 1.5 mm. In some embodiments, the outermost ring has a diameter of about 2.5 mm and represents the retinal region outside the macula.

In the example scan pattern shown in FIG. 3, each dot along the scan trajectory represents a location on the retina at which a measurement is made and data is collected. In some embodiments, this may result from turning on a light source to generate a measurement beam at those points along the pattern and turning off the light source at other points along the pattern. Note that the density of measurements (i.e., the spacing between the measurement points or dots) varies along different regions or sections of the trajectory.

As shown in the example, the density of measurements is less for the portion of a lobe that lies within the innermost ring 332. The density of measurement points increases for the portion of the scan pattern that lies outside the innermost ring 332, increasing for the portion between rings 332 and 334, and further increasing for the portion at the end or tip of a lobe, which in the example, lies outside the middle ring 334. Thus, in this example, the density of measurement and data collection points varies along the scan.

In some embodiments, the density of measurement points along a scan pattern may be controlled by varying the scan speed of the scanning mirror and the geometry of the scan pattern generated by the scanning mirror, while maintaining the same A-Scan acquisition rate. Note that each lobe 310 comprises a substantially continuous scan pattern with an unscanned region inside the lobe or scan path of the measurement beam. As indicated by the measurement points and the variation in density of those points, the measurement beam and/or the sampling of data is not continuous and is instead modulated (turned on and off) during the scanning process.

The scanning mirror may be caused to move by applying a voltage or current waveform to one or more actuators, such as a microelectromechanical (MEMs) device. In some embodiments, the mirror may be caused to move by application of an electrostatic force. The electrostatic force may be provided by one or more capacitors. In some embodiments, the position or orientation of the mirror may be caused to move by application of an electromagnetic force. In some embodiments, the electromagnetic force may be provided by one or more of a galvanometer, an electrostatic transducer, or a piezo electric transducer.

During operation of the OCT system, a drive signal or waveform (or waveforms) is input to a scanner or scanning mirror controller. The drive signal operates to cause an actuator or actuators to move the mirror. This may be accomplished by causing the mirror to rotate about the X and/or Y-axes. As the mirror is moved, a measurement beam that reflects off the mirror is redirected and caused to move on a patient's retina in accordance with a scan pattern that is determined by the input drive signal or signals. The light reflected from the surface or internal layers of the retina interferes with a reference version of the measurement beam to form an interferogram which is detected by a detector. Thus, a drive signal to one or more actuators may be varied to cause a measurement beam to be scanned on a retina in a desired scan pattern, with the data detected and stored by other elements of an OCT system.

Figure 4:
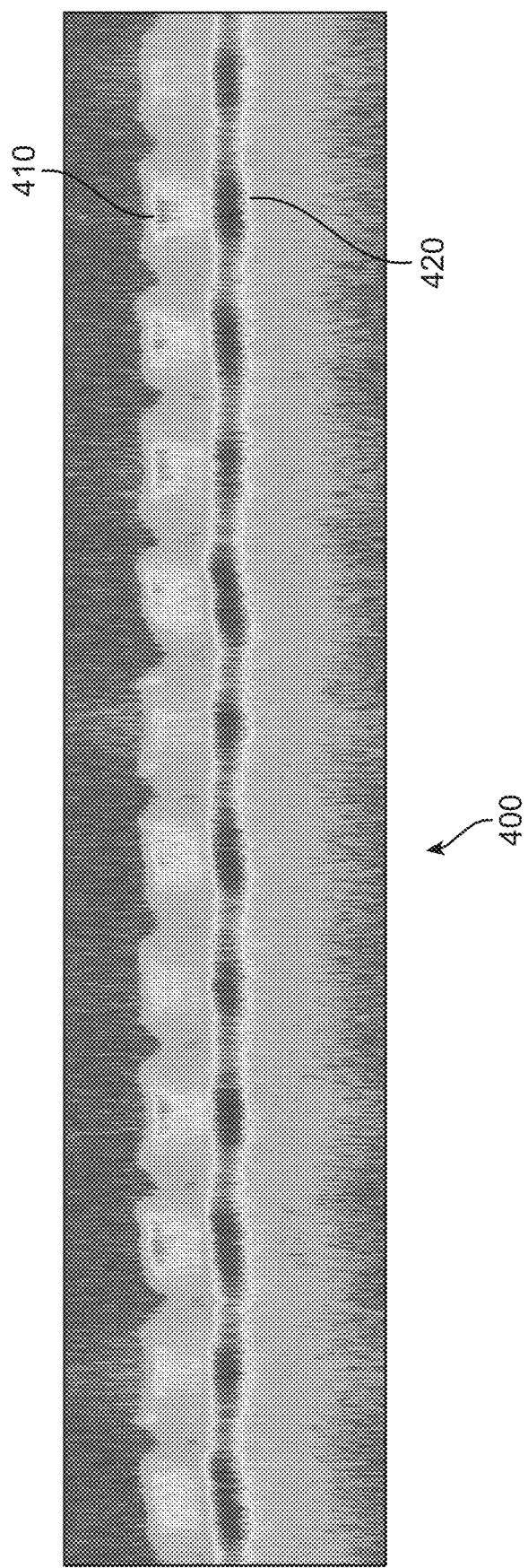
FIG. 4 shows a set of interferograms or scans acquired by an OCT using the scan pattern or trajectory of FIG. 3, in accordance with some embodiments.

FIG. 4 shows a set of interferograms or A-scans 400 acquired by an OCT using the scan pattern or trajectory of FIG. 3, in accordance with some embodiments. In the figure, a set of A-scans have been stacked on top of each other in to generate the image shown. In some embodiments, each A-scan is generated by measuring an intensity of an interferogram as the one or more VCSELs is swept in wavelength over time, and Fourier transforming the measured interferogram. Thus, in FIG. 4, a set of Fourier transformed interferograms is shown, in which each Fourier transformed interferogram corresponds to an A-scan. Each A-scan of the measurement beam along the scan pattern generates one horizontal row of pixels in the figure. An OCT system is able to image different depths of the retina and its associated tissue structures by varying the position of a reference mirror. For example, the figure shows an image of the inner limiting membrane (ILM) 410 and the Retinal Pigment Epithelium (RPE) 420 obtained by concatenating or stacking multiple scans performed during a cycle of the scan pattern of FIG. 3.

In some embodiments, the data collected using one scan pattern may be subjected to further processing to obtain data that would be expected to be generated by a second scan pattern. In some embodiments, this may involve interpolating, extrapolating or otherwise processing measurement data acquired as a result of the scan pattern of FIG. 3 to produce data that would be expected to be acquired as a result of a second and different scan pattern.

Figure 5:
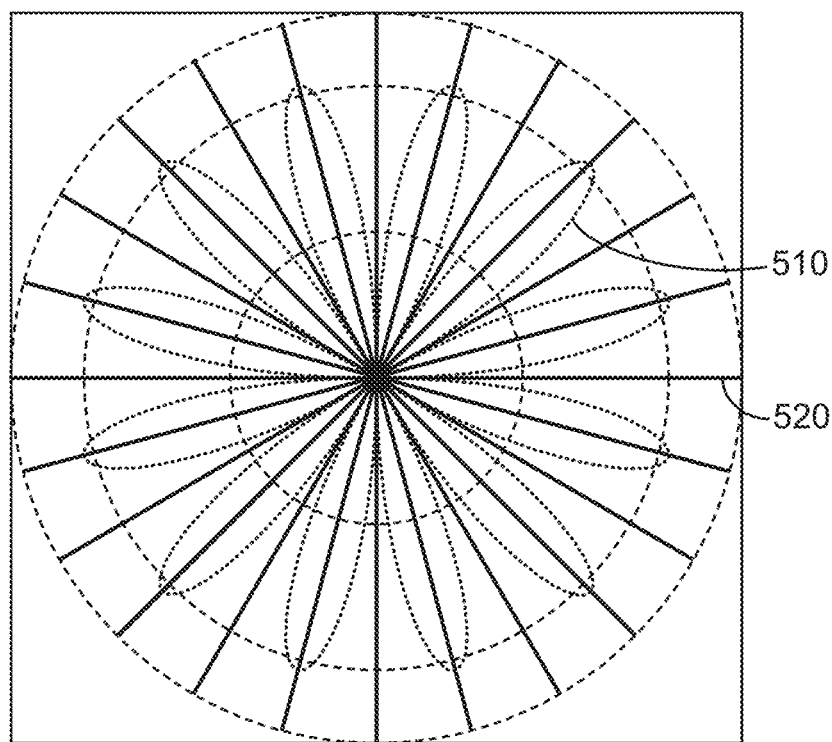
FIG. 5 shows the scan pattern of FIG. 3 superimposed on a radial scan pattern, data for which may be obtained by interpolation of the data obtained from the scan pattern of FIG. 3, in accordance with some embodiments.

As an example, FIG. 5 shows the scan pattern of FIG. 3 superimposed on a radial scan pattern, data for which may be obtained by interpolation of the data obtained from the scan pattern of FIG. 3, in accordance with some embodiments. In this example, data obtained by movement of a measurement beam along a flower scan pattern 510 may be interpolated or otherwise processed to produce the data expected by performing a scan over the "star" or radial pattern 520. The interpolation, extrapolation or other form of processing used to generate data corresponding to a different scan pattern may be based on any suitable technique or methodology, including but not limited to linear interpolation, polynomial interpolation, nearest neighbor interpolation, or spline interpolation, among others.

Although FIG. 5 illustrates a star or radial scan pattern, it should be understood that interpolation, extrapolation or other processing of measurement data obtained by use of a flower or rose curve scan pattern may be used to generate measurement data corresponding to other types of scan patterns, including but not limited to stop and go, circular, star, Lissajous, linear, raster and other patterns. In some embodiments, this allows data acquired using a flower, curved, or lobed scan pattern to be used to "simulate" or represent data that would be obtained using a radial, linear, or other scan pattern.

Figure 6:
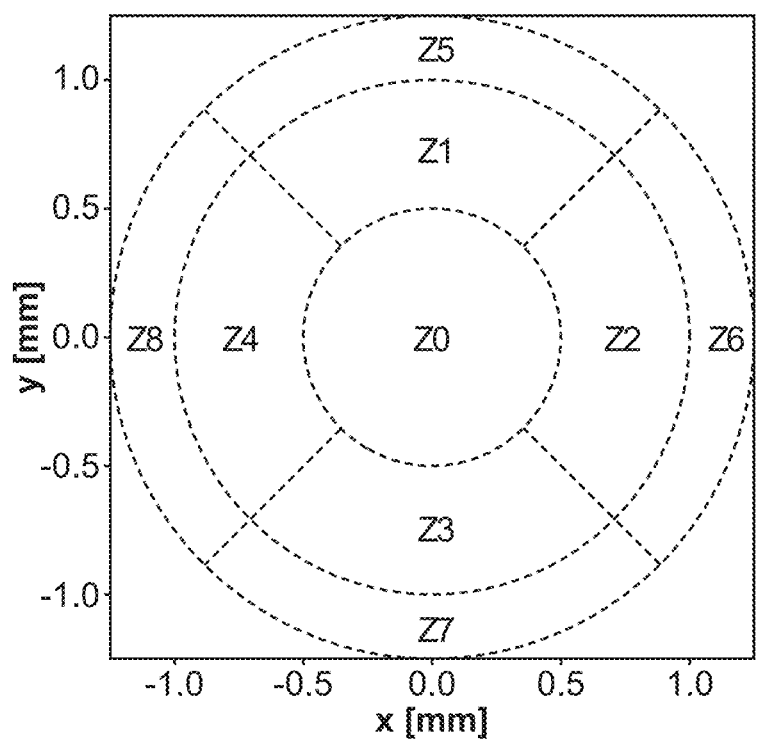
FIG. 6 shows how the surface of a patient's eye may be divided into zones or regions for purposes of comparing scan patterns by comparing the amount of scanning or scan time spent collecting data from each zone, in accordance with some embodiments.

FIG. 6 shows how the surface of a patient's eye may be divided into zones or regions for purposes of comparing scan patterns by comparing the amount of scanning or scan time spent collecting data from each zone, in accordance with some embodiments. As shown in the figure, a surface of an eye may be divided into a set of zones, in this case 9 zones. Each zone is identified by a label Z0, Z1 to Z8 in the figure. In some embodiments, each of the zones can be used to generate a retinal thickness map, in which the overall thickness, e.g. average thickness, for each zone is shown. In some embodiments, data from measurements of the same eye at different times are compared to generate a map showing changes in retinal thickness for each of the zones over time.

As has been described, measurements of retinal thickness and changes in retinal thickness over time can provide indications of disease or illness, even for diseases or illnesses not directly related to the eye. This is one reason for the value of obtaining OCT scan data and processing that data to enable it to be used to create images that can be analyzed to determine retinal thickness.

Although some OCT systems enable the collection and processing of OCT scan data to enhance images showing the ILM and RPE layers of the retina, interpretation of those images can still be difficult and prone to error. The fuzziness or lack of distinct boundaries between the layers can introduce uncertainty into measurements of retinal thickness. One way of reducing these inaccuracies is by training a machine learning model to "segment" the images into better defined ILM and RPE layers. This segmentation enables a more accurate measurement of retinal thickness, and as mentioned, this information is helpful in the diagnosis and treatment of eye diseases. In some embodiments, the segmentation of OCT images is performed using a trained neural network.

As described herein, a trained convolutional neural network (CNN) can be used to segment an interferogram and provide a resulting image that can be used more effectively to determine a measurement of retinal thickness. In some examples, this is the result of the CNN operating on an image to enhance the boundaries of an inner limiting membrane (ILM) layer, where the ILM is the boundary between the retina and the vitreous body of the eye. Using a CNN or other form of trained image processing model assists in identifying the boundaries of the tissue layers in the retina and obtaining more accurate measurements of retinal thickness.

However, as mentioned, training a CNN or other form of neural network requires a relatively large set of properly annotated training data. Unfortunately, a sufficiently large set of annotated data may not be available for interferograms produced by a specific type of OCT device or system, such as one that operates using a different scan pattern than that used to generate scans for which more data is available. For example, at present there is a relatively large amount of data available for scans generated using a radial or raster scan pattern, but relatively little for scans generated using other forms of scan patterns. This can make it difficult to train and use a CNN to segment images generated from scans that result from using a scan pattern that is not a radial pattern.

Figure 7:
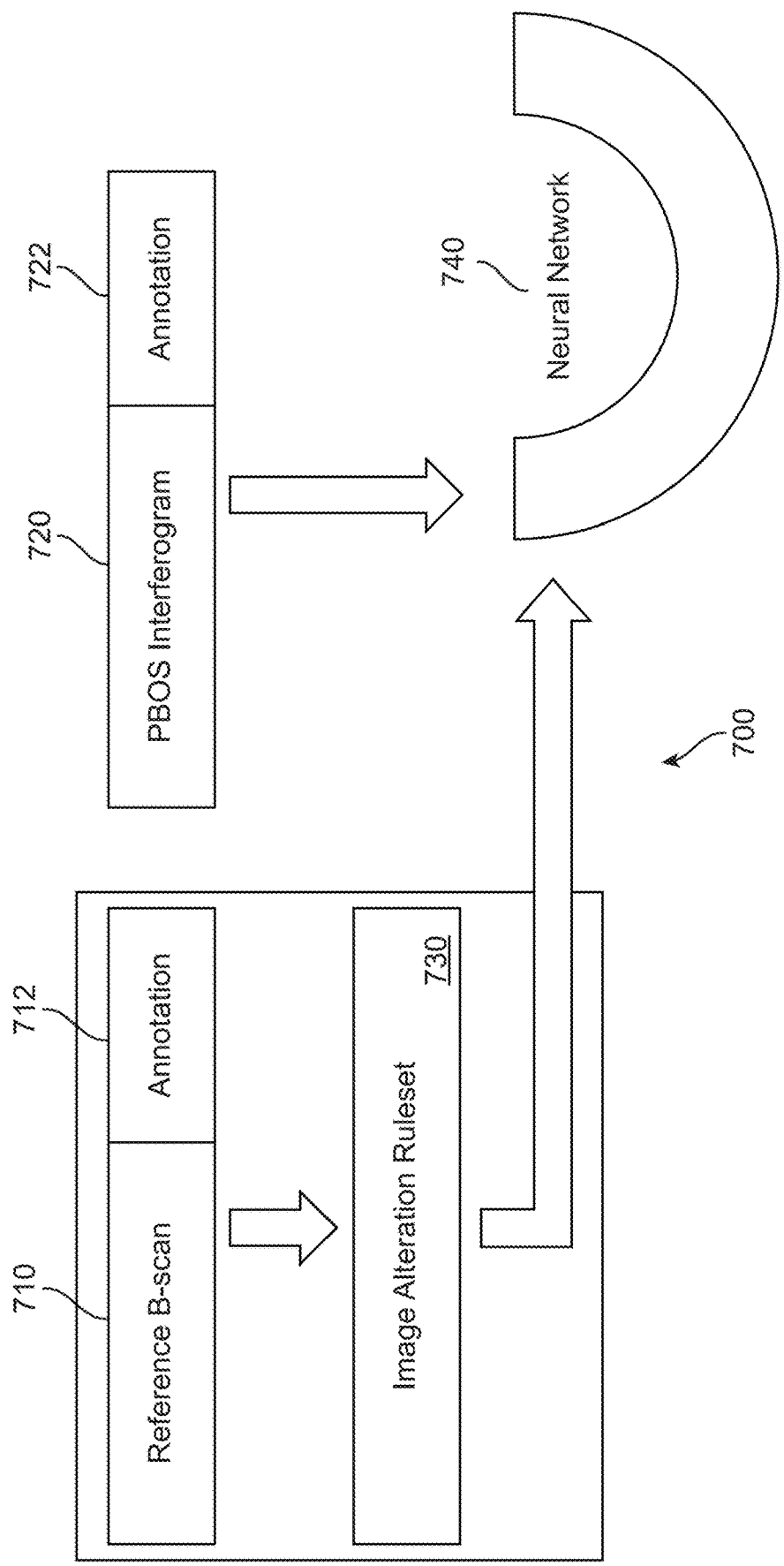
FIG. 7 shows a process for training a CNN or other form of neural network to perform a segmentation of an interferogram image, in accordance with some embodiments.

FIG. 7 shows a process 700 for training a CNN or other form of neural network to perform a segmentation of an interferogram image, in accordance with some embodiments. As shown in the figure, in some embodiments, the training data comprises OCT scan data from two sources: (1) a first source 710 (referred to as "Reference B-Scan" in the figure, and associated annotations or labels 712 (referred to as "Annotation" in the figure); and (2) a second source 720 (referred to as PBOS Interferogram" in the figure, and associated annotations or labels 722 (referred to as "Annotation" in the figure).

More generally, the two sources represent a first source of data obtained from operating an OCT system and based on moving a measurement beam in a first scan pattern and a second source obtained from operating an OCT system (which is typically a different OCT system, but is not required to be) and based on moving a measurement beam in a second and different scan pattern. In some embodiments, the first scan pattern is a linear (for example, radial) scan pattern and the second scan pattern is a curved (for example, flower) scan pattern.

In some embodiments, the amount of information, data, scans, images, or interferograms available from one of the two sources may be sufficient for purposes of training a CNN, while the other is relatively less and considered insufficient for training purposes. In some embodiments, the images or interferograms obtained from one of the OCT systems or scan patterns may be higher resolution than those obtained from the other OCT system or scan pattern.

In some embodiments, the trained neural network may be intended to process images or interferograms obtained using a scan pattern for which there is not sufficient training data.

In some embodiments, this may be the type of scan referred to as a PBOS Interferogram 720 in the figure. In some embodiments, scan 720 may be based on data obtained using a curved scan pattern. As a result, if it is desired to be able to perform image segmentation or another form of image processing on an image formed using data obtained from a curved scan pattern, then a process for training a neural network that can utilize images obtained from a different scan pattern, for example a linear scan pattern is desired. FIG. 7 illustrates an example of such a training process.

In some embodiments, images generated from data obtained using both types of scan patterns (a linear and a curved scan pattern) are used as part of the training process. As will be described in greater detail, one or both of the sources of training data may be subject to additional processing prior to being used for training the CNN. Further, in some embodiments, the image input to the trained CNN (in this example a PBOS interferogram 720) may be subjected to further processing prior to being input to the trained CNN.

Because the two sources of OCT data (710 and 720) represent data obtained from systems that use different scan patterns and/or have differing resolution, the scans, interferograms, or images obtain from one type of scan pattern may benefit from further processing prior to being used to train a CNN or being used as input to a trained CNN. This further processing may rely on the same or different forms of image processing (e.g., translating, sampling, flipping, blurring, interpolating, etc.).

In some embodiments, the further processing is used to generate a larger set of scan data or images for use as training data for a CNN. The additional training data is formed from B-scan images 710 based on data generated using the first type of scan pattern. As mentioned, in one example, the trained CNN performs image processing on images generated from the scan pattern data or images obtained using the second scan pattern (720).

In some embodiments, the scan pattern data or images obtained using the second scan pattern may be subjected to further processing prior to being used for purposes of training or as input to the trained model. In some embodiments, this further processing may comprise interpolating or extrapolating data obtained using the second scan pattern to produce data that would be expected to result from using the first scan pattern. In some embodiments, this comprises interpolating data obtained using a curved scan pattern to produce data that would be expected to result from using a linear scan pattern.

In some embodiments, the further processing may be used to alter images formed from data obtained using the first scan pattern so that the images more closely resemble images formed from data obtained using the second scan pattern. In some embodiments, this type of processing may be used to process an original set of training data prior to its input to a CNN. In some embodiments, this type of processing may be used to generate additional training data after application of other processes to generate variations of an original set of images.

As shown in the figure, in some embodiments, annotated scan images obtained from a first scan pattern 710 may be subjected to alteration by application of an image alteration ruleset 730 prior to being used as training data for a Neural Network 740. In some embodiments, Neural Network 740 may comprise a CNN and have a specific architecture, referred to as a U-Net. As described in greater detail with reference to FIG. 12, a U-Net neural network consists of a contracting path and an expanding path, which results in the u-shaped architecture. The contracting path is a convolutional network that consists of repeated application of convolutions, each followed by a rectified linear unit (ReLU) and a max pooling operation. During the contraction stages, the spatial information is reduced while feature information is increased. The expanding path combines the feature and spatial information through a sequence of up-convolutions and concatenations with high-resolution features from the contracting path.

Image alteration ruleset 730 may comprise a set of image processing operations that are applied to data or images obtained from scans 710 to enable that data or images to be used as inputs to train Neural Network 740. In some embodiments, the trained network is then used to process or segment data or images obtained from scans 720. In some embodiments, image alteration ruleset 730 may comprise one or more image processing operations such as non-linear subsampling, scaling, flipping, translation, brightness and contrast adaptation, or application of a Gaussian blur filter.

As mentioned, and as shown in FIG. 7, in some embodiments, scan data or images based on the second type of scan pattern 720 may also be used in the training process. In such cases, those images are annotated 722 and data or images based on both types of scan patterns are used as training data. Further, in some embodiments, data or images based on the first type of scan pattern may be processed as described to generate additional training data. Still further, in some embodiments, data based on the second type of scan pattern may be interpolated, extrapolated, or otherwise processed to generate training data. In some embodiments, annotations 722 may be derived by interpolating annotations 712; this may be useful when an interferogram 720 is not easily or reliably annotated by a human because of the relatively low optical resolution of the measurement data. In these cases, interpolation of annotations or labels may be required as the scan pattern used to generate scans 710 and 720 are not identical.

When trained, the input data or image to the trained neural network 740 may be data or an image based on the second type of scan pattern, either in its original form or after being interpolated, extrapolated, or otherwise processed. In some embodiments, the interpolation or other data processing may be to generate data or an image that more closely resembles that which would be obtained from the first scan pattern. In some embodiments, this interpolation may operate on data obtained from a curved scan pattern to generate data that would be expected to be obtained from a linear scan pattern.

Figure 8:
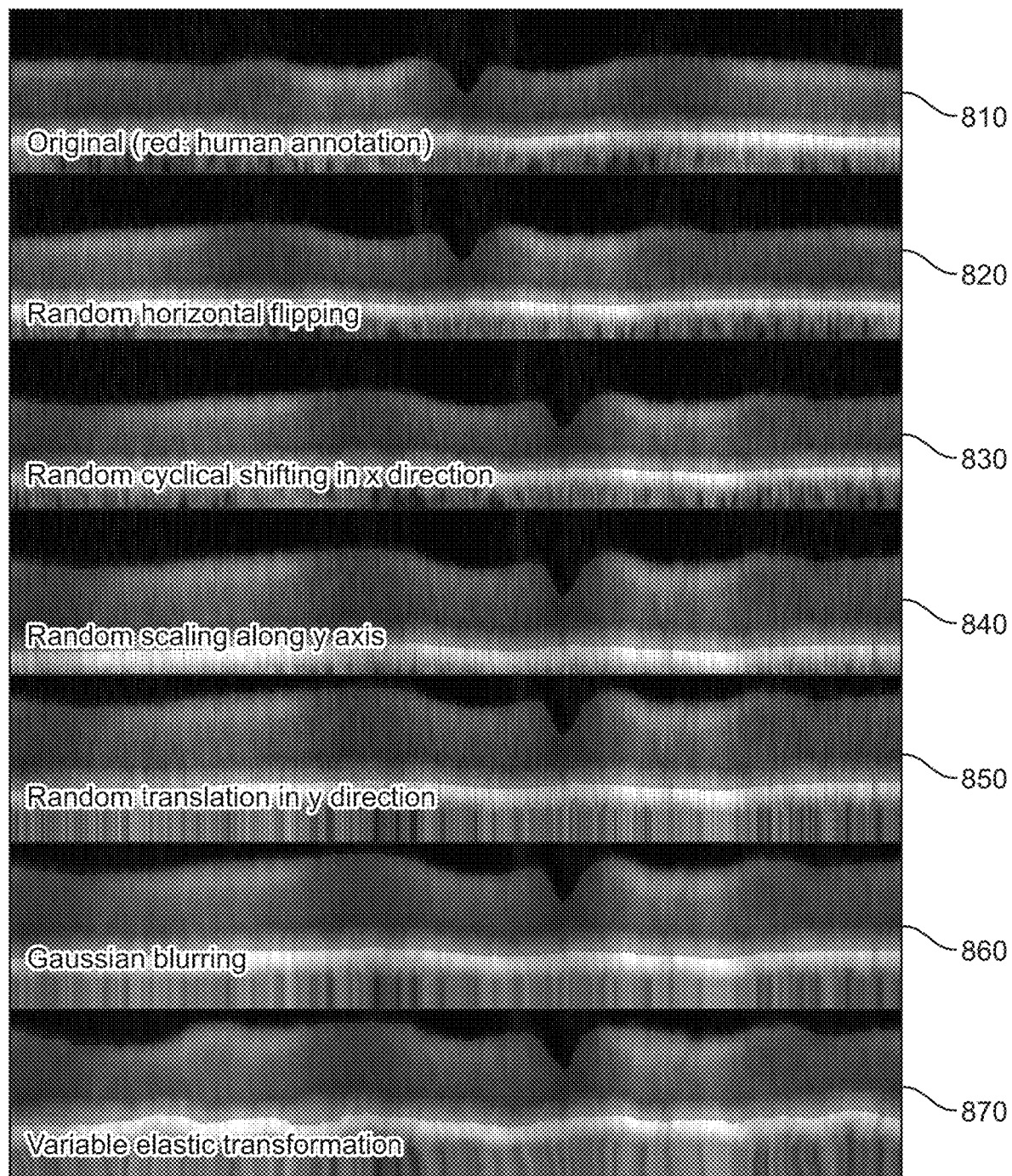
FIG. 8 shows a set of operations that may be used in a process for generating additional training data for use in training a CNN or other form of neural network as described with reference to FIG. 7, in accordance with some embodiments.

FIG. 8 shows a set of operations that may be used in a process for generating additional training data for use in training a CNN or other form of neural network as described with reference to FIG. 7, in accordance with some embodiments. As shown in the figure, an original image 810 (such as one obtained from segmenting a B-scan based on a first scan pattern 710) may be subjected to operations that include random horizontal flipping (as suggested by the image shown in 820), random shifting in the x direction (830), random scaling along the y axis (840), random translation in the y direction (850), Gaussian blurring (860), or a variable elastic transformation (870). The synthetic oversampling of the original images produces slightly altered training images and its use as additional training data may minimize the risk of overfitting of the model to the training set. In some embodiments, these types of geometric transforms may be referred to as techniques for augmenting a data set.

Figure 9:
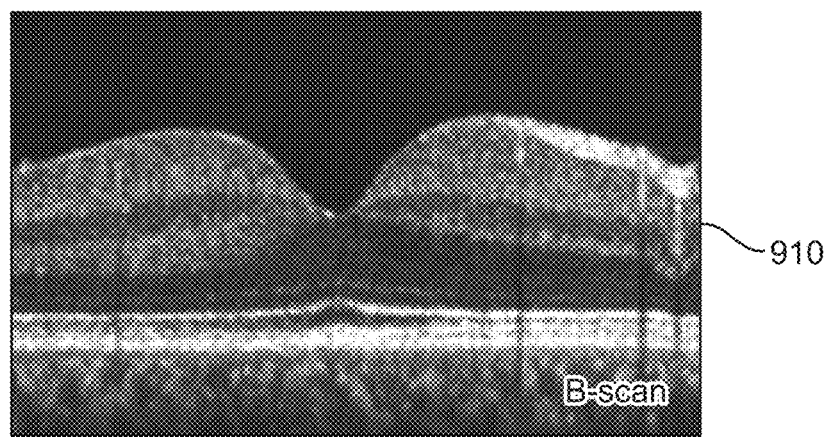
FIG. 9 shows an original B-scan based on a radial scan pattern, a result of applying an image degradation ruleset to that scan pattern to generate an interferogram, and an interferogram obtained by use of a second scan pattern, in accordance with some embodiments.
Figure 9:
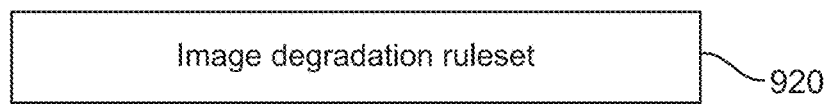
Figure 9:
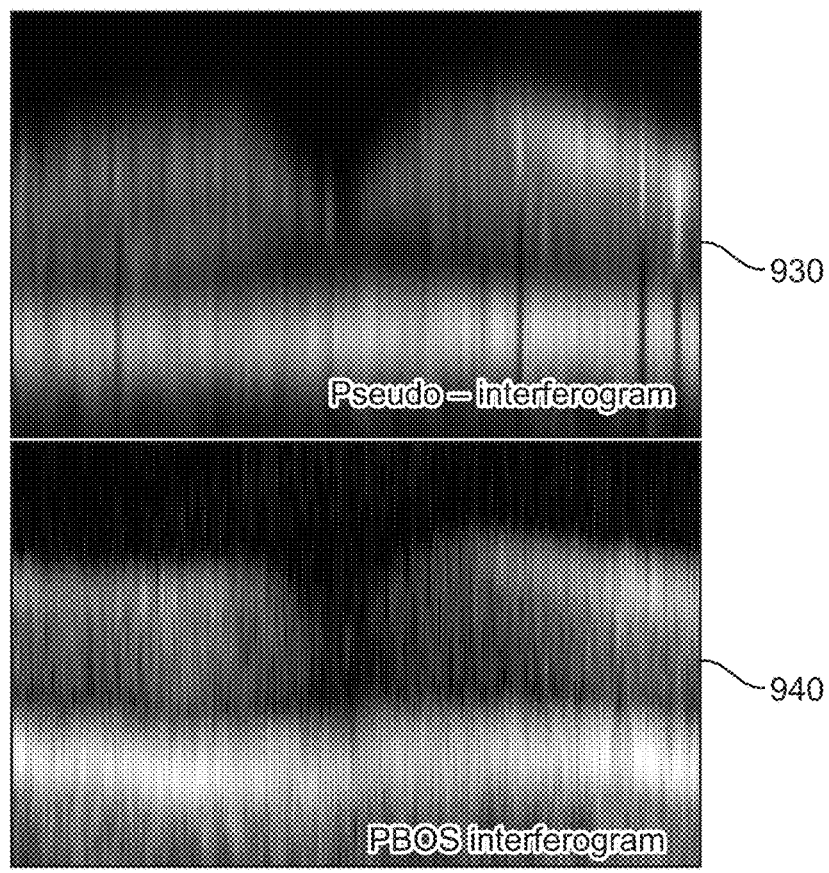

FIG. 9 shows an original B-scan based on a radial scan pattern, a result of applying an image degradation ruleset to that scan pattern to generate an interferogram, and an interferogram obtained by use of a second scan pattern, in accordance with some embodiments. The figure shows an original image 910 based on a radial scan pattern (termed a B-scan in the figure). An image degradation or alteration ruleset 920 is applied to image 910. As shown in the figure, application of the image degradation or alteration ruleset 920 to image 910 produces image 930 (termed a "pseudo interferogram" in the figure). Note that application of image degradation or alteration ruleset 920 to image 910 generates an image 930 that more closely resembles that obtained from an OCT device performing a second type of scan pattern 940 (in this case the flower scan pattern of FIG. 3). In some embodiments, these types of data processing operations may be referred to as techniques for degenerating an image that is part of a data set.

This resemblance is a basis for an embodiment in which a trained neural network operates to generate a B-scan from an input scan obtained using a different scan pattern than conventionally used to generate a B-scan. For example, given a set of training data comprising B-scan images obtained from a linear scan pattern and a second set of images obtained from a curved scan pattern, a CNN may be trained to associate annotated features in the B-scan images with the corresponding features in the second set of images. In some cases, the B-scan images may be subjected to one or more of the processing operations shown and described with reference to FIGS. 8 and 9.

In some cases, the data obtained from the curved scan pattern may be interpolated or otherwise processed to more closely correspond to the data obtained for a specific linear scan pattern or region of a retina scanned using a linear scan pattern prior to being used as training data. In some embodiments, this is referred to as a resampling process or operation. When trained, the neural network may operate to receive as an input an image obtained using the curved scan pattern (or an interpolated set of data generated from the curved scan pattern) and in response output an image corresponding to a B-scan that would be obtained for a specific linear scan pattern performed at a region of a retina.

This embodiment allows use of a curved scan pattern to generate data using a first OCT device to be the source of an image that would conventionally be generated by use of a linear scan pattern performed by a second OCT device. Similarly, it allows use of data generated by an OCT system that executes a first scan pattern to be used as part of training a model to segment data generated by an OCT system that executes a second scan pattern.

Figure 10A:
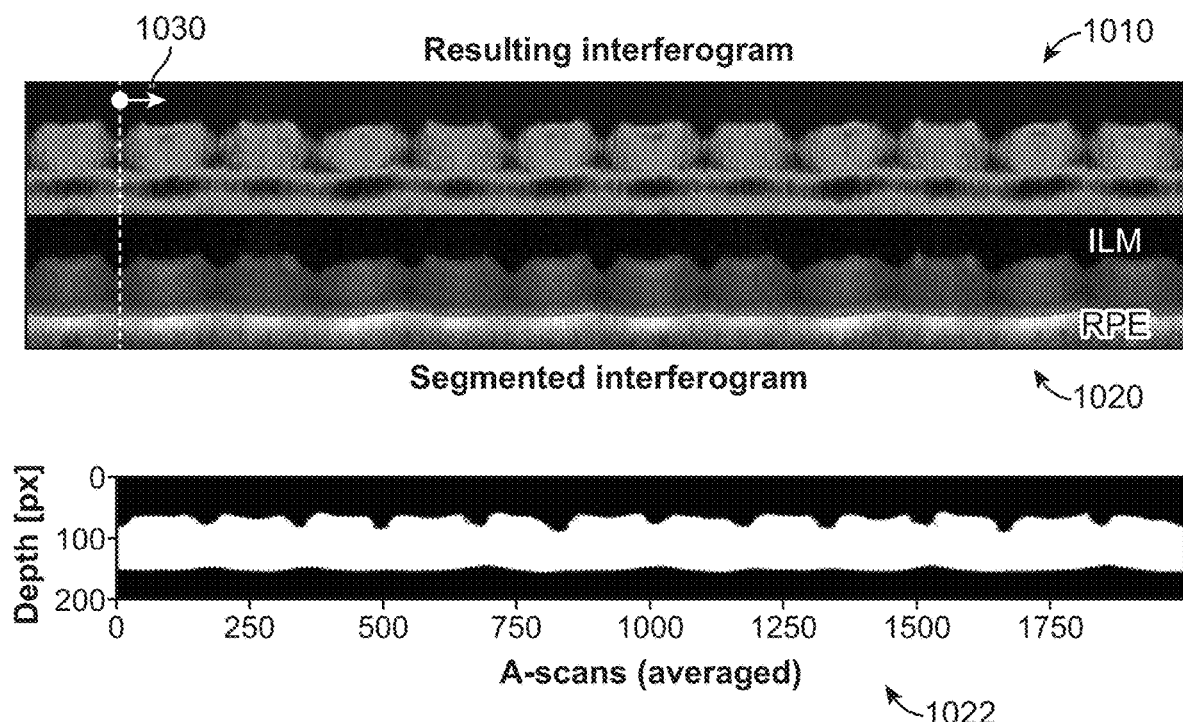
FIG. 10A shows an original interferogram and a segmented interferogram obtained from processing the original interferogram using a trained CNN, in accordance with some embodiments.

FIG. 10A shows an original interferogram 1010 and a segmented interferogram 1020 obtained from processing the original interferogram using a trained CNN, in accordance with some embodiments. Original interferogram 1010 (identified as "resulting interferogram" in the figure) is constructed from multiple scans using the scan pattern of FIG. 3 that capture data obtained from different depths into a retina. One or more A-scans (which may be averaged or subject to other signal processing to combine the scan data from multiple scans) at a location on the scan pattern of FIG. 3 produces data corresponding to a single vertical line in the figure. Data from a plurality of scans are combined to produce the interferogram 1010 shown. When this type of interferogram is input to a trained neural network of the type described with reference to FIGS. 7 and 12, the output is a segmented interferogram image 1020. Segmented interferogram image 1020 more readily identifies certain tissue layers or layer boundaries, such as the ILM and RPE layers. This can improve the ability to determine changes in retinal thickness over time and the identification of fluid or fluid pools in the retina. Interferogram 1022 is another example of the output that may be generated by a trained CNN in response to the input of interferogram 1010. In some embodiments, the output may consist of other or additional segmentation classes, e.g., one or more of intra-retinal fluid ("IRF"), subretinal fluid ("SRF"), pigment epithelium detachment ("PED"), etc.

Note that in some embodiments, processing of interferogram 1010 to improve the segmentation may be performed, such as that termed decurving and described in U.S. Provisional Patent Application 62/706,417, titled "System and Method for Optical Coherence Tomography A-Scan Decurving", filed Aug. 14, 2020, the entire contents of which is incorporated by reference.

Figure 10B:
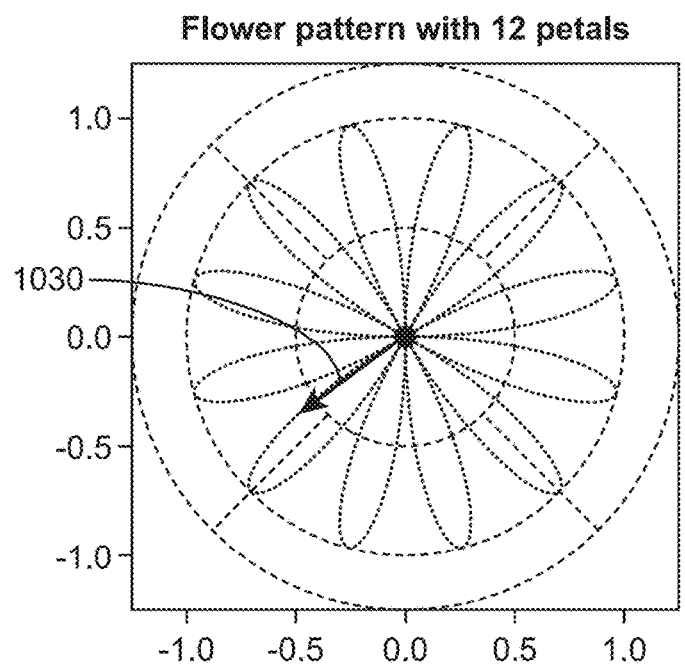
FIG. 10B shows an example of the flower pattern scan pattern of FIG. 3 that was used to obtain the interferogram of FIG. 10A, including an indication of the portion of the scan pattern that generated the indicated section of the interferogram.

FIG. 10B shows an example of the flower pattern scan pattern of FIG. 3 that was used to obtain the interferogram of FIG. 10A, including an indication of the portion of the scan pattern that generated the indicated section of the interferogram (shown by arrow 1030 in each of FIGS. 10A and 10B).

Figure 11A:
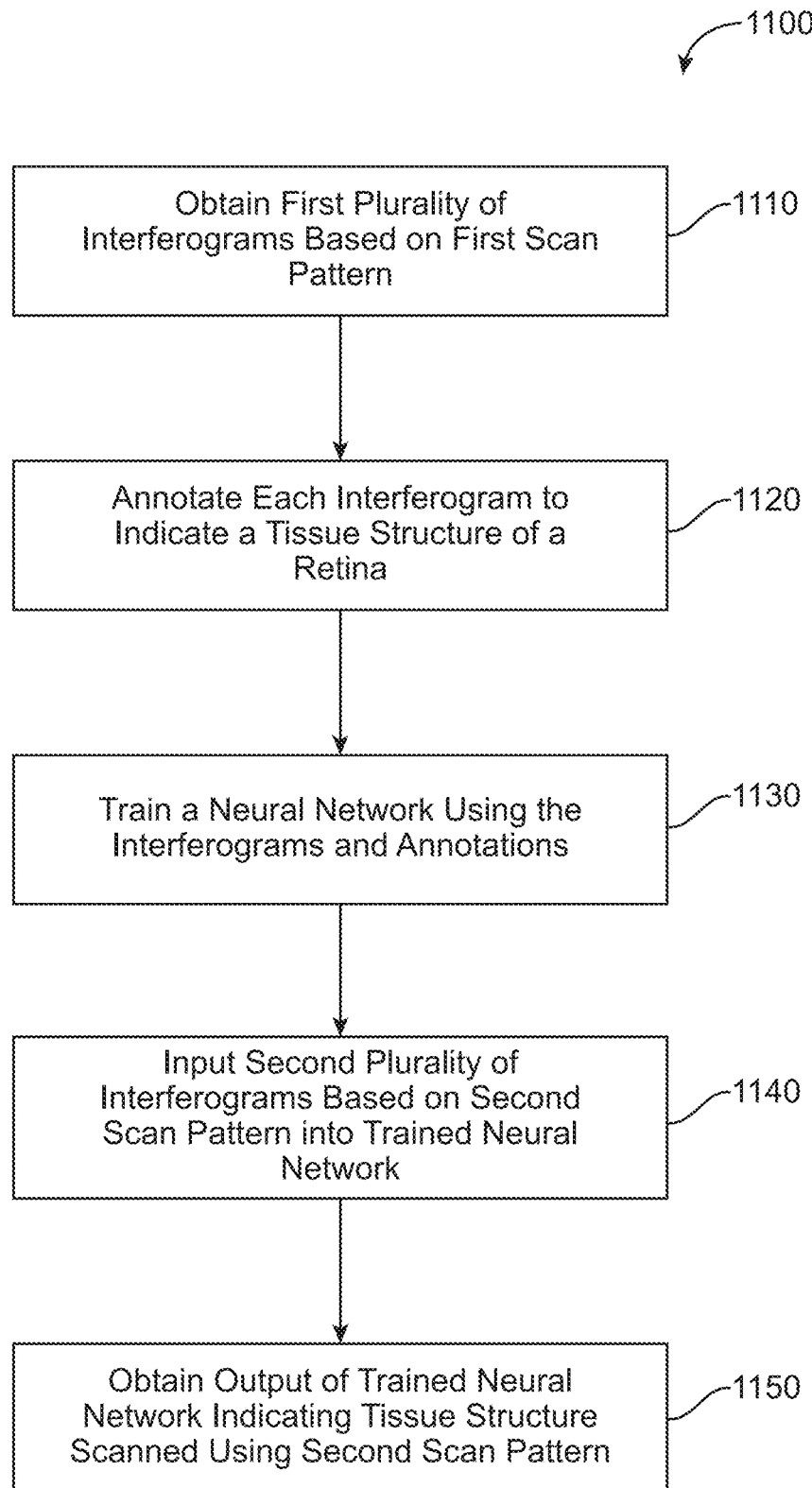
FIG. 11A is a flow chart or flow diagram illustrating a process, method, operation, or function for training a neural network using a set of OCT interferograms obtained using a first scan pattern to determine a retinal tissue structure in a set of OCT interferograms obtained using a second scan pattern, in accordance with some embodiments.

FIG. 11A is a flow chart or flow diagram 1100 illustrating a process, method, operation, or function for training a neural network using a set of OCT interferograms obtained using a first scan pattern to determine a retinal tissue structure in a set of OCT interferograms obtained using a second scan pattern, in accordance with some embodiments. The steps or stages shown in the figure may be performed in whole or in part as a result of the execution of a set of instructions by a programmed processor or processing unit. As shown in the figure, at step 1110, a first plurality of interferograms are obtained. These interferograms are based on data collected by an OCT system using a first scan pattern, for example a radial scan pattern. At step 1120, each of the first plurality of interferograms are annotated or labeled to indicate one or more tissue structures of a retina. These tissue structures may include an ILM or RPE, for example. Typically, the annotation or labeling is performed by a human who has expertise in the subject matter of the interferograms. In some examples, the annotation or labeling may be performed with the assistance of a rule-set and image processing software, or another type of automated or semi-automated process.

In some embodiments, the annotation may be assigned to each pixel in an image and may comprise one of Background, Foreground, Intraretinal Fluid, Subretinal Fluid, or Pigment Epithelium Detachment.

At step 1130, a neural network is trained using the first plurality of interferograms and the associated annotations. In some embodiments, the neural network may be a CNN, and more specifically a U-Net architecture, described in greater detail with reference to FIG. 12. At step 1140, a second plurality of interferograms are input to the trained neural network. The second plurality of interferograms are based on data collected by an OCT system using a second and different scan pattern, for example the flower scan pattern of FIG. 3. At step 1150, the output of the trained neural network is obtained, where the output indicates the tissue structure of the retina scanned using the second scan pattern.

The embodiment of FIG. 11A represents one of several task or objectives that may be performed by a suitably trained model. In the example embodiment of FIG. 11A, a model is trained using training data (and the associated annotations) obtained from a first OCT system that operates to acquire image data using a first scan pattern. After training, the model accepts as an input data generated by a second OCT system that operates to acquire data using a second scan pattern and segments that image data.

Figure 11B:
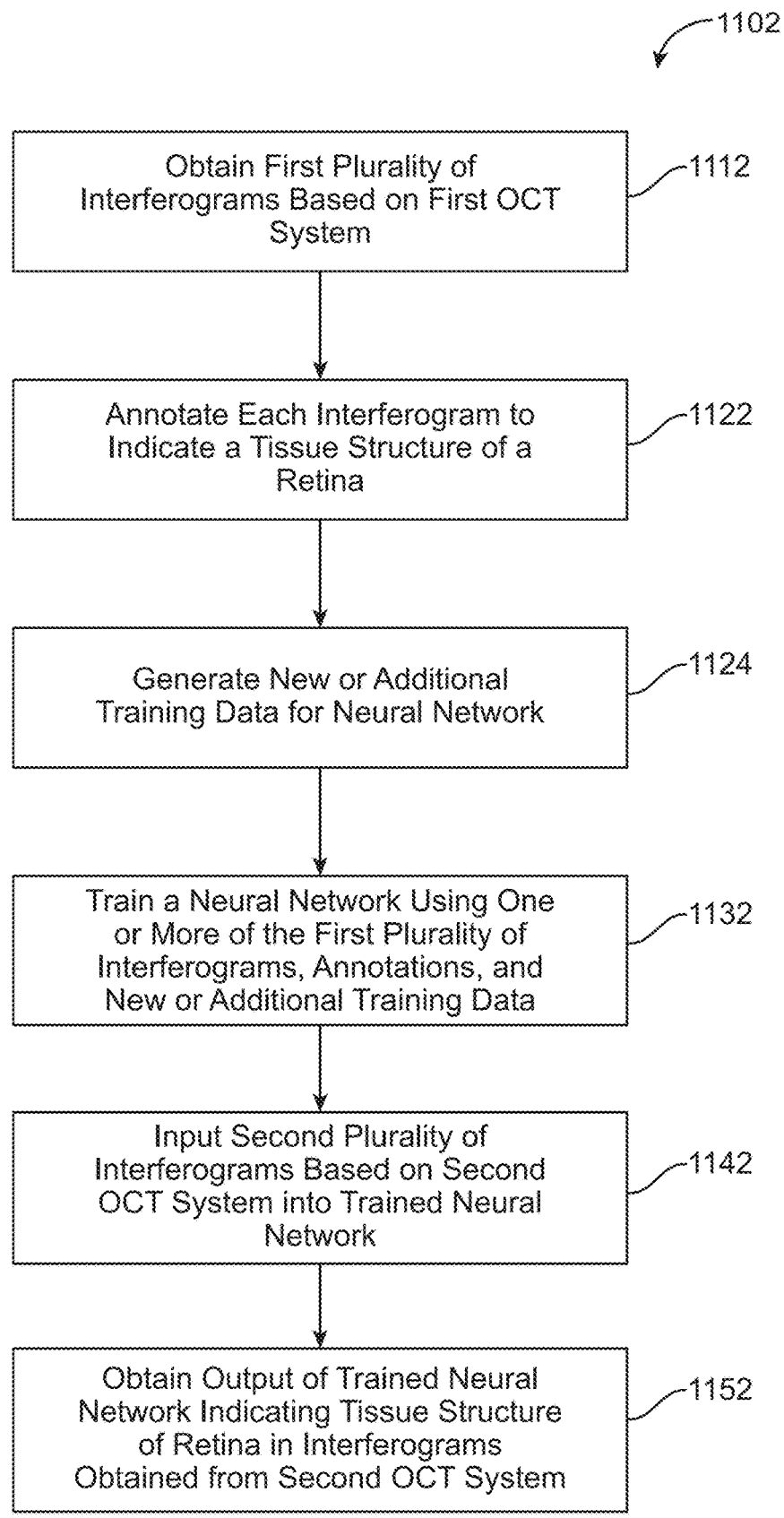
FIG. 11B is a flow chart or flow diagram illustrating a process, method, operation, or function for generating additional training data for training a neural network using a set of OCT interferograms obtained using a first OCT system to determine a retinal tissue structure in a set of OCT interferograms obtained using a second OCT system, in accordance with some embodiments.

However, as mentioned, in some cases, there may not be sufficient training data available or the available training data may need to be supplemented or altered to enable it to be used to train a model to operate on input data obtained from the second OCT system. FIG. 11B is a flow chart or flow diagram 1102 illustrating a process, method, operation, or function for generating additional training data for training a neural network using a set of OCT interferograms obtained using a first OCT system to determine a retinal tissue structure in a set of OCT interferograms obtained using a second OCT system, in accordance with some embodiments.

As shown in FIG. 11B, in some embodiments, at step 1112, a first plurality of interferograms are obtained by using a first OCT system to scan a retina or retinas. The first OCT system may have an associated resolution, scan pattern or other characteristic. Each interferogram is then annotated or labeled, which typically involves mapping each pixel to a class, such as a structure, layer, boundary, or feature of a retina, as suggested by step 1122. Next, at step 1124, new or additional training data is generated. As described herein, the new or additional training data may be used with the first plurality of interferograms and annotations described with reference to steps 1112 and 1122, or instead of those interferograms and annotations as a replacement set of training data and associated annotations.

Next, at step 1132, a model is produced (such as a trained neural network) using one or more of the first plurality of interferograms, the original annotations, the new training data (and associated annotations), or the additional training data (and associated annotations). The new or additional training data and annotations may be generated by one or more of the following data processing techniques: (1) Augmentation—this set of techniques or operations is used to generate additional training data by applying one or more operations (geometrical transformations, such as those illustrated in FIG. 8) to a set of data associated with an image. Augmentation is used to provide increased data variability, increase the robustness of the trained model, and prevent over-fitting of the model to the original set of data. The geometrical transformations may be applied to the corresponding annotations to generate annotations for the image data produced by the augmentation process; (2) Degeneration—this set of techniques or operations (such as blurring) is applied to original image data obtained from an OCT system with a higher resolution to obtain data that would be expected to be obtained from an OCT system with lower resolution. In some embodiments, degenerated images may be used as part of a curriculum learning process for training a model; (3) Resampling—this technique or operation is applied to image data obtained using a first scan pattern to generate image data expected to be obtained using a second and different scan pattern (typically from a different OCT system). Resampling operations may comprise nearest-neighbor interpolation, extrapolation, curve-fitting, etc.; and (4) Registering or registration—this technique or operation is used to align annotations or indications of features (boundaries, regions, fluid, etc.) made to a first set of images to those in a second set of OCT images obtained by degenerating the first set of images.

After being trained, the neural network (or other form of trained model) receives as an input a second plurality of interferograms obtained from using a second OCT system, as suggested by step 1142. At a step 1152, an output of the trained neural network is obtained, indicating tissue structures of the of the retina in interferograms obtained from the second OCT system. The output of the trained model is a segmentation of the input images/interferograms indicating a structure, layer, boundary, feature, pool of liquid, or other aspect of an image. The segmented image may be obtained by mapping each pixel to a class or classes.

Figure 11C:
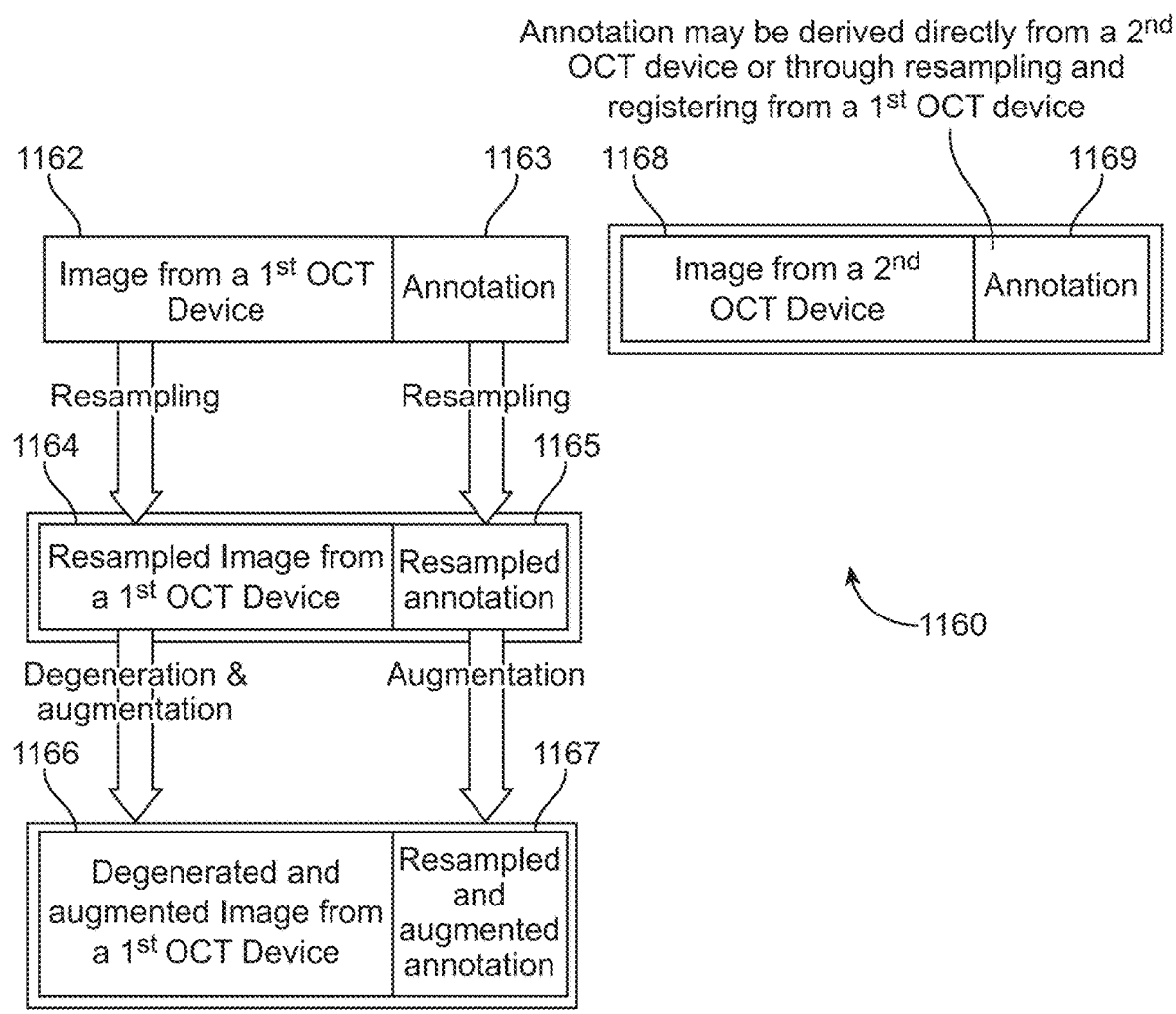
FIG. 11C is a diagram illustrating an embodiment in which image data obtained from a first OCT system and its associated annotations are subjected to one or more of resampling, degeneration, and augmentation operations to generate additional training data for use in training a model that is being trained with image data obtained from a second OCT system and its associated annotations.

FIG. 11C is a diagram illustrating an embodiment 1160 in which image data obtained from a first OCT system and its associated annotations are subjected to one or more of resampling, degeneration, and augmentation operations to generate additional training data for use in training a model that is being trained with image data obtained from a second OCT system and its associated annotations. As shown in the figure, image data obtained from a first OCT system 1162 and its associated annotations 1163 are both subjected to a resampling process. The resampling process may involve interpolation, extrapolation, curve fitting, or other suitable data processing technique. The result of the resampling process is a set of resampled image data obtained from the first OCT system 1164 and a set of associated resampled annotations 1165. Next, the resampled image data 1164 is subjected to one or more of degeneration or augmentation, as suggested by step 1166. Degeneration may involve blurring or other transforms or processes that operate on initial image data to produce image data corresponding to an image of lower resolution. Augmentation may involve geometrical transforms or operations such as those described with reference to FIG. 8. The result is image data obtained from a first OCT system that is made to be similar to that expected to be obtained from a second OCT system, where the second OCT system is of lower resolution and operates using a different scan pattern than the first OCT system. In addition, by use of the augmentation operations additional training data has been generated to assist in preventing over-fitting of the model to the original set of data. As also shown in the figure, the resampled annotation data 1165 is subjected to an augmentation process to generate additional annotation data 1167 that may be used with the resampled, degenerated, or augmented data 1166 as part of a training process.

The processing described with reference to FIG. 11C generates additional training data and annotations that may be used with image data obtained from a second OCT system 1168 and its associated annotations 1169 to train a model. The trained model is used to segment image data obtained using the second OCT system. However, because insufficient training data (or annotations for data) is available for the second OCT system (which would typically have a different resolution and utilize a different scan pattern than the first OCT system), one or more of the resampling, degeneration, and augmentation techniques are applied to image data (and in some cases, to the annotations) obtained from the first OCT device to generate additional training data and annotations to be used with the available training data and annotations.

The annotations 1169 for the image data obtained from the second OCT system may be obtained directly by human or machine annotation of the image data 1168 for the second OCT system, or by one or more of augmentation, resampling, or registering of the annotations 1163 for the image data 1162 obtained from the first OCT system. The registering or registration of annotations or labels may depend on the characteristics of the first or of the second device and may comprise consideration of tilt or shift between scans, scan pattern, scan location, or other characteristics.

As described, original image data and the associated annotations may be used alone or with additional training data and annotations to train a model used to segment image data. In some embodiments, the additional training data may be generated by one or more of augmentation, degeneration, or resampling operations or processes. Similarly, the annotations associated with the additional training data may be based on augmentation, resampling, or registration of the annotations associated with the original image data.

In some embodiments, a process of transfer learning or curriculum learning may be used as part of training a model used for segmentation of image data. Herein transfer learning refers to a process whereby a model (or layers that are part of a model) that has been trained for one task or objective is used for a different one. This may involve inserting one or more hidden layers of a previously trained model into a new model and then completing the training of the new model using a set of training data.

Curriculum learning refers to a process whereby a model is trained by progressively increasing the difficulty of the task with each iteration of a training cycle. As an example, this may be achieved by progressively decreasing the quality of training data (e.g., by degeneration) for each successive iteration or set of iterations, thereby increasing the difficulty in correctly classifying the data. In some embodiments, this may be accomplished by degenerating higher resolution image data to a greater degree as the number of iterations increases and/or adding lower resolution image data obtained from a different OCT system into the training data set with a higher probability as the number of iterations increases.

In this regard, the processing illustrated in FIG. 11C may also or instead be used as part of a curriculum learning process for training a model as it results in generating lower quality image and annotation data which may be used by itself or with the original image and annotation data for training.

Figure 11D:
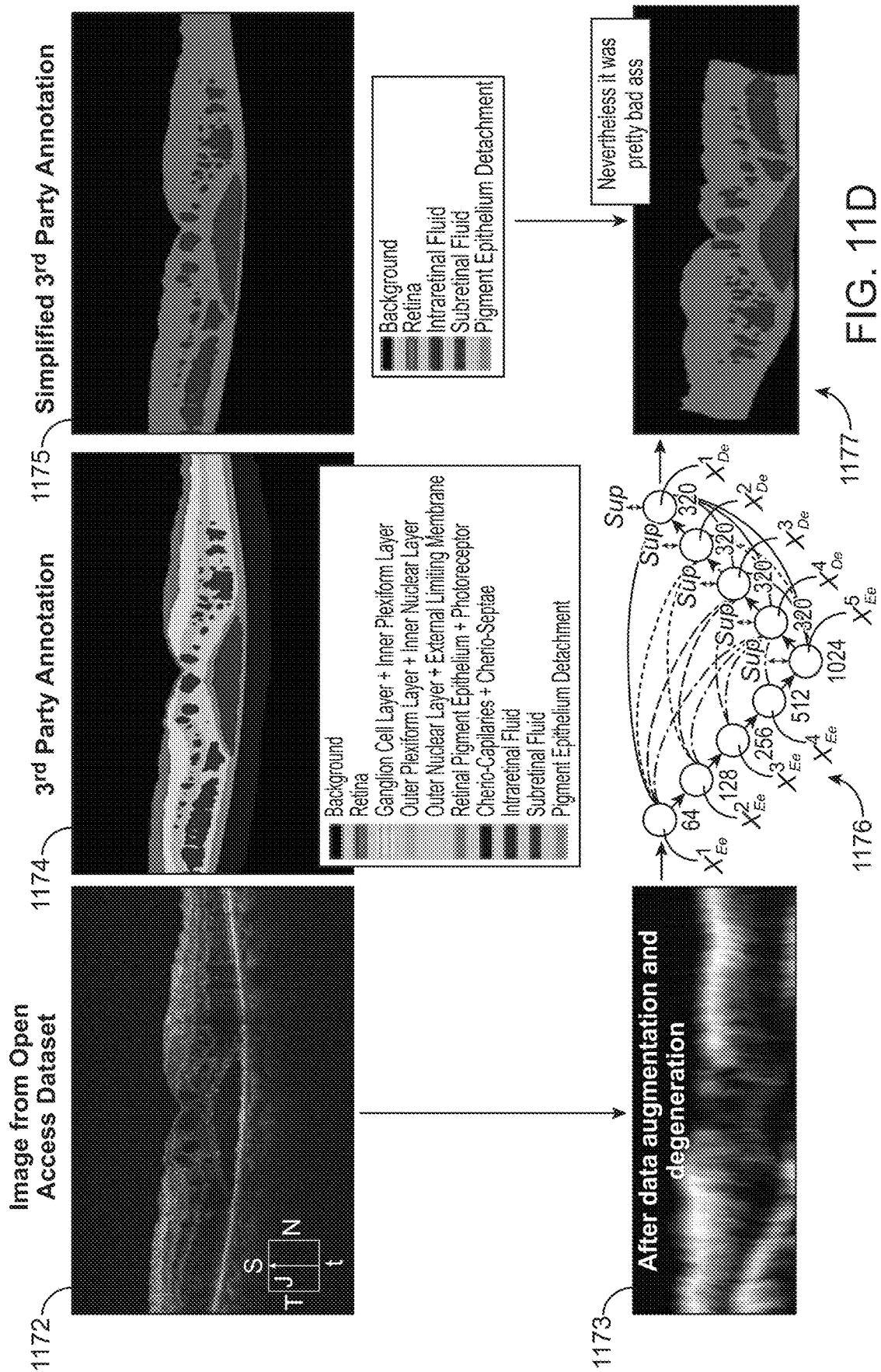
FIG. 11D is a set of diagrams illustrating an embodiment in which training data obtained from an open access data set of interferograms (retinal images) is subjected to augmentation and degeneration processes to generate training data for a model that is intended to be used with input data obtained from an OCT system having a lower resolution than the OCT system used to generate the interferograms.

FIG. 11D is a set of diagrams 1170 illustrating an embodiment in which training data obtained from an open access data set of interferograms (retinal images) 1172 is subjected to augmentation and degeneration processes 1173 to generate training data for a model that is intended to be used with input data obtained from an OCT system having a lower resolution than the OCT system used to generate the interferograms 1172. The initial data 1172 is annotated to produce annotated or labeled images 1174 that indicate the classes corresponding to pixels in the images. As suggested by 1174, the annotations may identify several classes or features of the original images, including features such as tissue layers, tissue boundaries, pools of fluid, or other structures in a retina. The annotated images 1174 may be simplified by removal of certain class identifications to produce a simplified set of annotations 1175 for use in training the model. In some embodiments, the simplified annotations 1175 result from applying one or more of the geometric transforms applied to image data 1172 as part of the data augmentation process. Degenerated and augmented image data 1173 and corresponding annotations 1175 may then be used as training data and labels for a model. When trained, the model 1176 (depicted as a neural network, and more specifically, a U-Net architecture) operates to generate a segmented image 1177 from input image data that corresponds to an OCT system having a lower resolution than that used to generate the original image data 1172.

Figure 12:
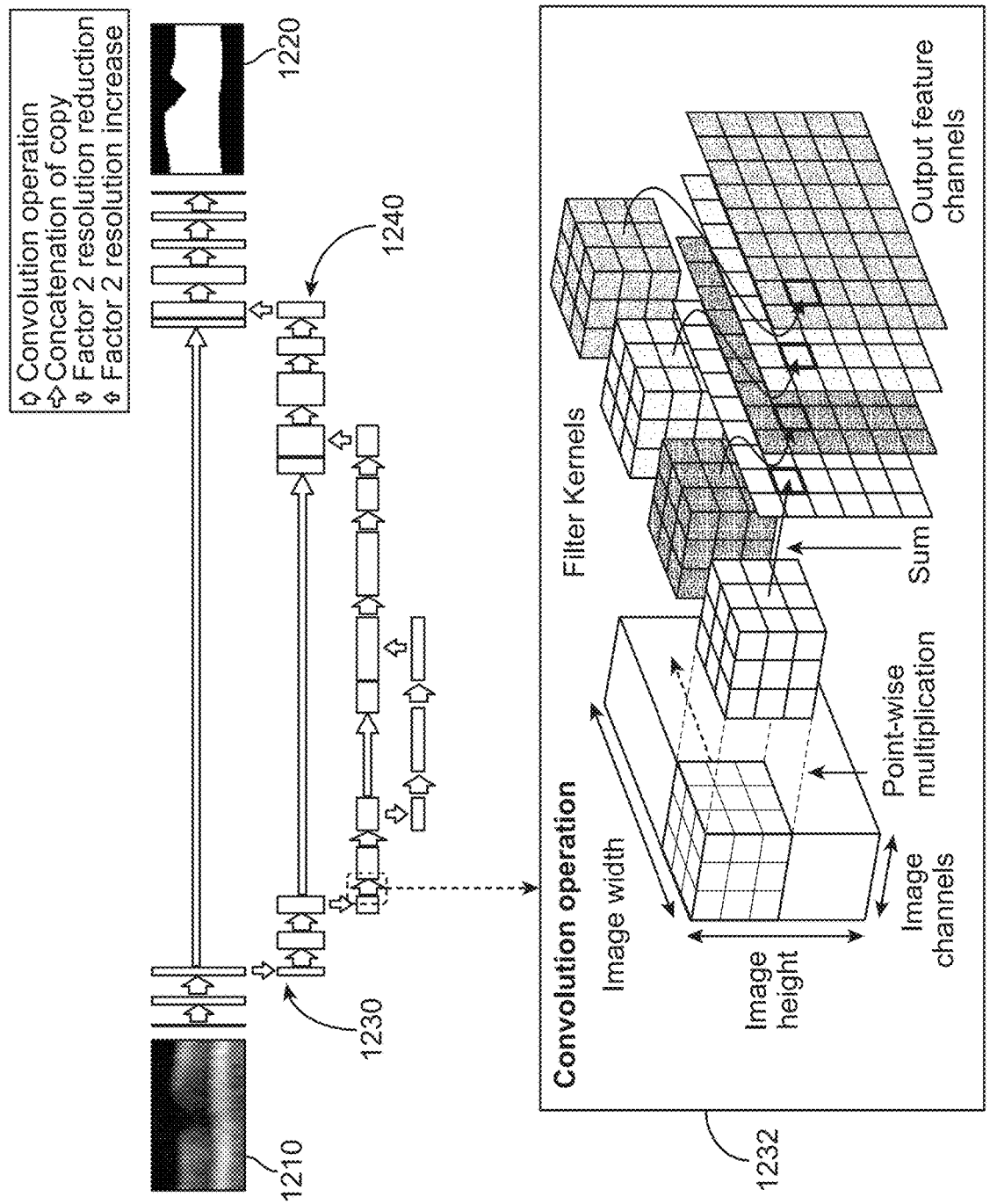
FIG. 12 is a diagram illustrating an example of a convolutional neural network (CNN) architecture that may be used to process an interferogram image and the output of the CNN representing a segmented image, in accordance with some embodiments.

FIG. 12 is a diagram illustrating an example of a convolutional neural network (CNN) architecture that may be used to process an interferogram image 1210 and the output of the CNN representing a segmented image 1220, in accordance with some embodiments. As shown in the figure, the CNN includes a contractor path 1230 that operates to exchange spatial features of an image for semantic features followed by an expansion path 1240 that operates to exchange the semantic features for spatial features.

The contractor path 1230 may be thought of as an encoder that typically includes a pre-trained classification network applying convolution blocks 1232 followed by a maxpool down-sampling. The result is to encode an input image into feature representations at multiple different levels. The expansion path 1240 may be thought of as a decoder that semantically projects the discriminative features (i.e., lower resolution features) learnt by the encoder onto the pixel space (thereby producing a higher resolution) to provide a dense classification. Typically, the decoder consists of up-sampling and concatenation operations followed by convolution operations. Up-sampling may be referred to as transposed convolution, up-convolution, or deconvolution, and up-sampling methods include Nearest Neighbor, Bilinear Interpolation, and Transposed Convolution, for example.

Each convolution operation 1232 is typically implemented as a point-wise multiplication operation (such as a dot-product between an image section and a weighting value) followed by a summing operation, with several weighting or filter layers (referred to as kernels) being applied in some examples. In one example embodiment, a U-Net architecture for a CNN that may be used to process image data (such as that shown in FIG. 12) comprises 18 convolutional layers, 1.79 million biases and weights, and between 32 and 256 semantic feature channels.

After each stage of image processing the result is concatenated or combined with the data created at the previous processing stage to form the final set of processed image data. As an example, after training the CNN of FIG. 12 may operate on an image of the type shown (in this example, an image formed from data collected by operating an OCT system in a curved scan pattern) to generate a segmented output image. The output image may then be used to better identify tissue structures in the retina and to make more reliable measurements of retinal thickness.

As mentioned, an example of a convolutional neural network architecture that may be used to implement one or more of the trained models described is referred to as a U-Net architecture. In particular, the UNet 3+ architecture has been found to be beneficial as it combines deep supervision during training with the skipping of connections between certain separated hidden layers. This enables the fusing of high-level semantic information with high-resolution spatial information. The UNet 3+ architecture is described in an article entitled "Unet 3+: A Full-Scale Connected Unet For Medical Image Segmentation" (arxiv.org/ftp/arxiv/papers/2004/2004.08790.pdf). In some embodiments, the convolutional neural network has between 5 and 19 hidden layers and an activation layer comprised of a ReLU (rectified linear unit).

Figure 13:
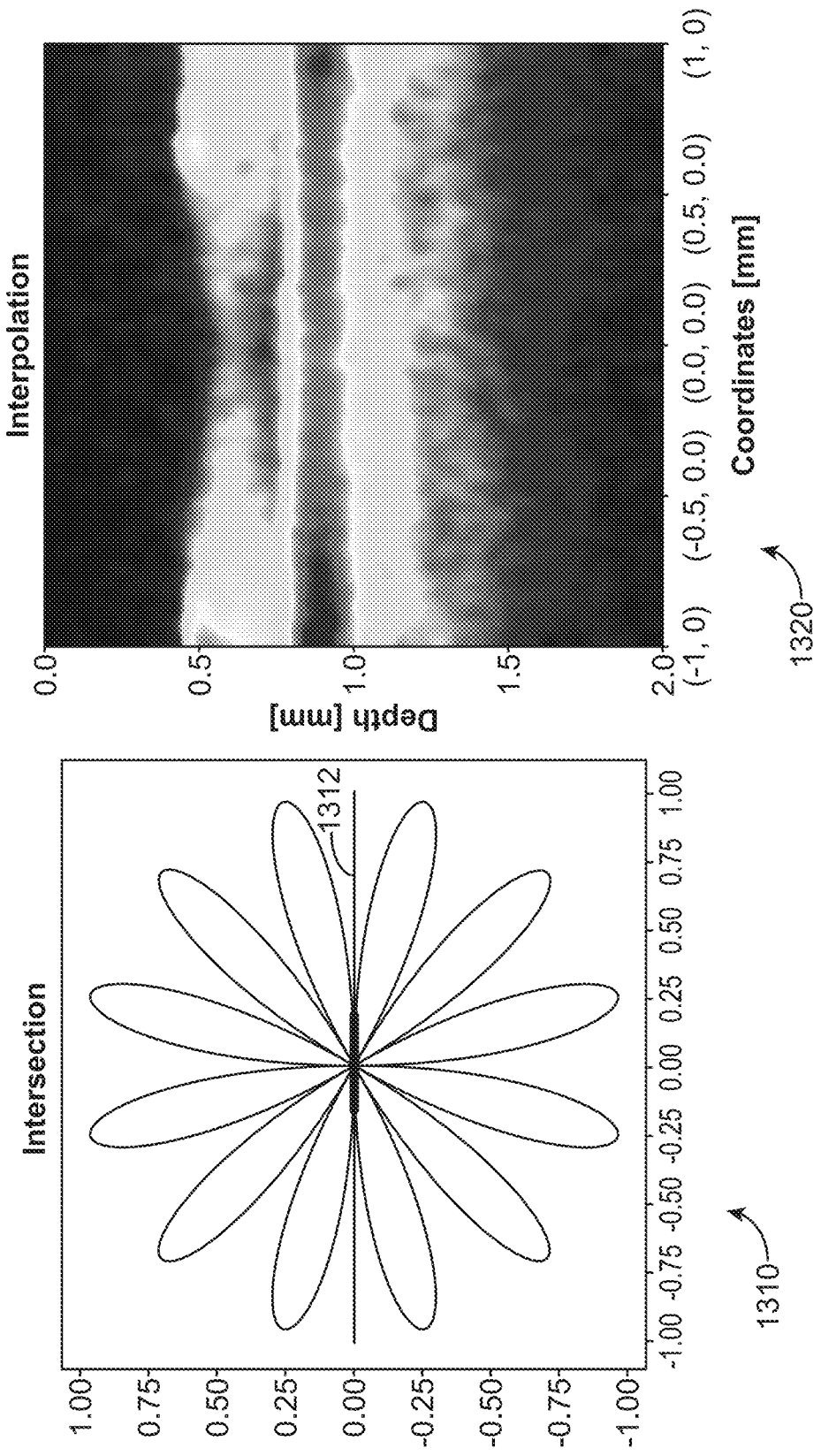
FIG. 13 is a diagram illustrating how a set of scan data obtained using the flower scan pattern of FIG. 3 may be subjected to further data processing operations (such as interpolation and gaussian blurring) to generate an image representing a B-scan of a selected cross section of a retina, in accordance with some embodiments.

FIG. 13 is a diagram illustrating how a set of scan data obtained using the flower scan pattern of FIG. 3 may be subjected to further data processing operations (such as resampling involving interpolation or gaussian blurring) to generate an image representing a B-scan of a selected cross section of a retina, in accordance with some embodiments. As shown in the figure, data collected using the flower scan pattern of FIG. 3 (1310) may be used to generate an image representing a B-scan 1320, with the image generated being determined by user selection of a specific cross section of interest on the flower scan data pattern of data points (as represented by line 1312).

As will be described further with reference to FIGS. 14 and 15, in some embodiments, a user may select a desired cross-sectional "slice" of data obtained using a flower scan pattern (as an example) and in response, the systems and methods described herein may generate a corresponding B-scan image. Depending upon the selected cross-section, the flower pattern scan data may be resampled by interpolation or another process to generate data that would typically result from a linear radial scan or raster scan, with the generated data being used as part of forming the B-scan. As a result, the output image represents a B-scan that would result from a linear scan of a specific type, although the original data was obtained using a flower scan pattern.

Figure 14:
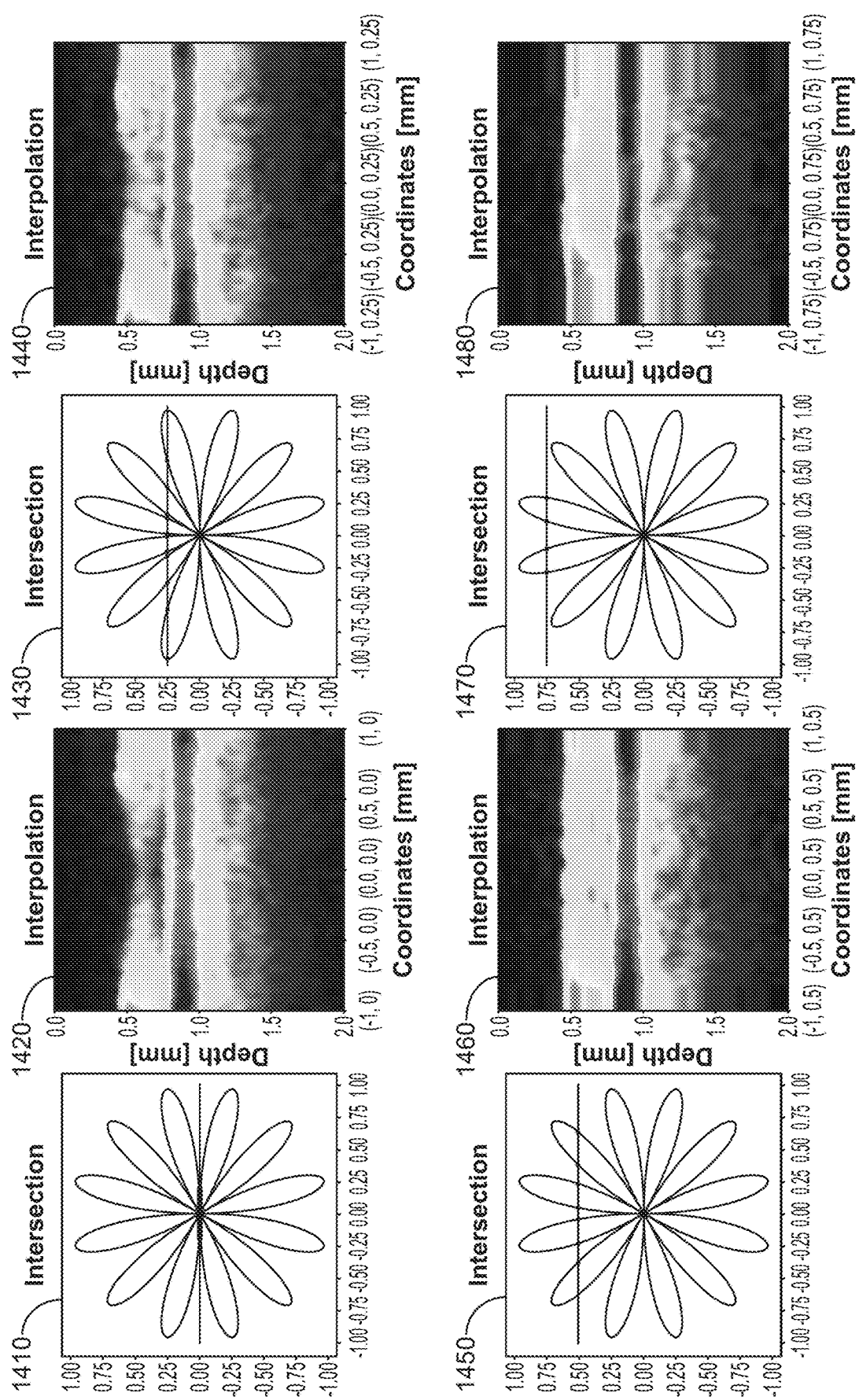
FIG. 14 is a diagram illustrating further examples of B-scans generated by processing of data obtained using the flower scan pattern of FIG. 3 for different slices through the pattern to create B-scans of different cross sections of a retina that would be obtained from a raster scan, in accordance with some embodiments.

FIG. 14 is a diagram illustrating further examples of B-scans generated by processing of data obtained using the flower scan pattern of FIG. 3 for different slices through the pattern to create B-scans of different cross sections of a retina that would be obtained from a raster scan, in accordance with some embodiments. As shown in the figure, by selecting a horizontal line through the data generated using the flower scan pattern, a B-scan image corresponding to a raster scan at a specific region of a retina may be generated.

For example, a slice 1410 through the flower scan pattern would generate a scan of the type shown in 1420. Similarly, a slice 1430 through the flower scan pattern would generate a scan of the type shown in 1440. A slice 1450 through the flower scan pattern would generate a scan of the type shown in 1460. A slice 1470 through the flower scan pattern would generate a scan of the type shown in 1480.

Figure 15:
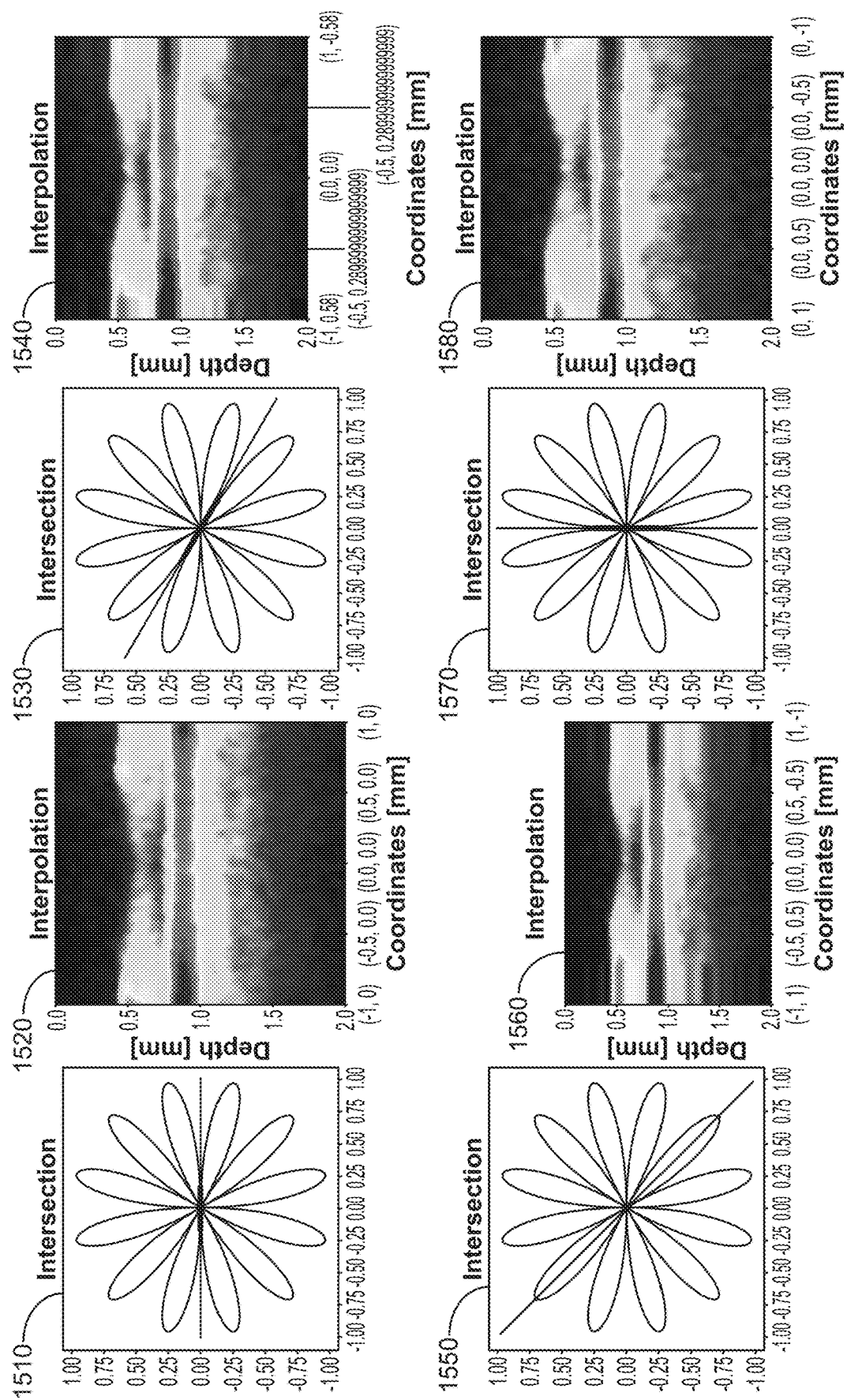
FIG. 15 is a diagram illustrating further examples of B-scans generated by processing of data obtained using the flower scan pattern of FIG. 3 for different slices through the pattern to create B-scans of different cross sections of a retina that would be obtained from a radial scan, in accordance with some embodiments.

FIG. 15 is a diagram illustrating further examples of B-scans generated by processing of data obtained using the flower scan pattern of FIG. 3 for different slices through the pattern to create B-scans of different cross sections of a retina that would be obtained from a radial scan, in accordance with some embodiments. As shown in the figure, by selecting a diagonal line including the origin through the data generated using the flower scan pattern, a B-scan image corresponding to a radial scan at a specific region of a retina may be generated.

For example, a slice 1510 through the flower scan pattern would generate a scan of the type shown in 1520. Similarly, a slice 1530 through the flower scan pattern would generate a scan of the type shown in 1540. A slice 1550 through the flower scan pattern would generate a scan of the type shown in 1560. A slice 1570 through the flower scan pattern would generate a scan of the type shown in 1580.

Figure 16:
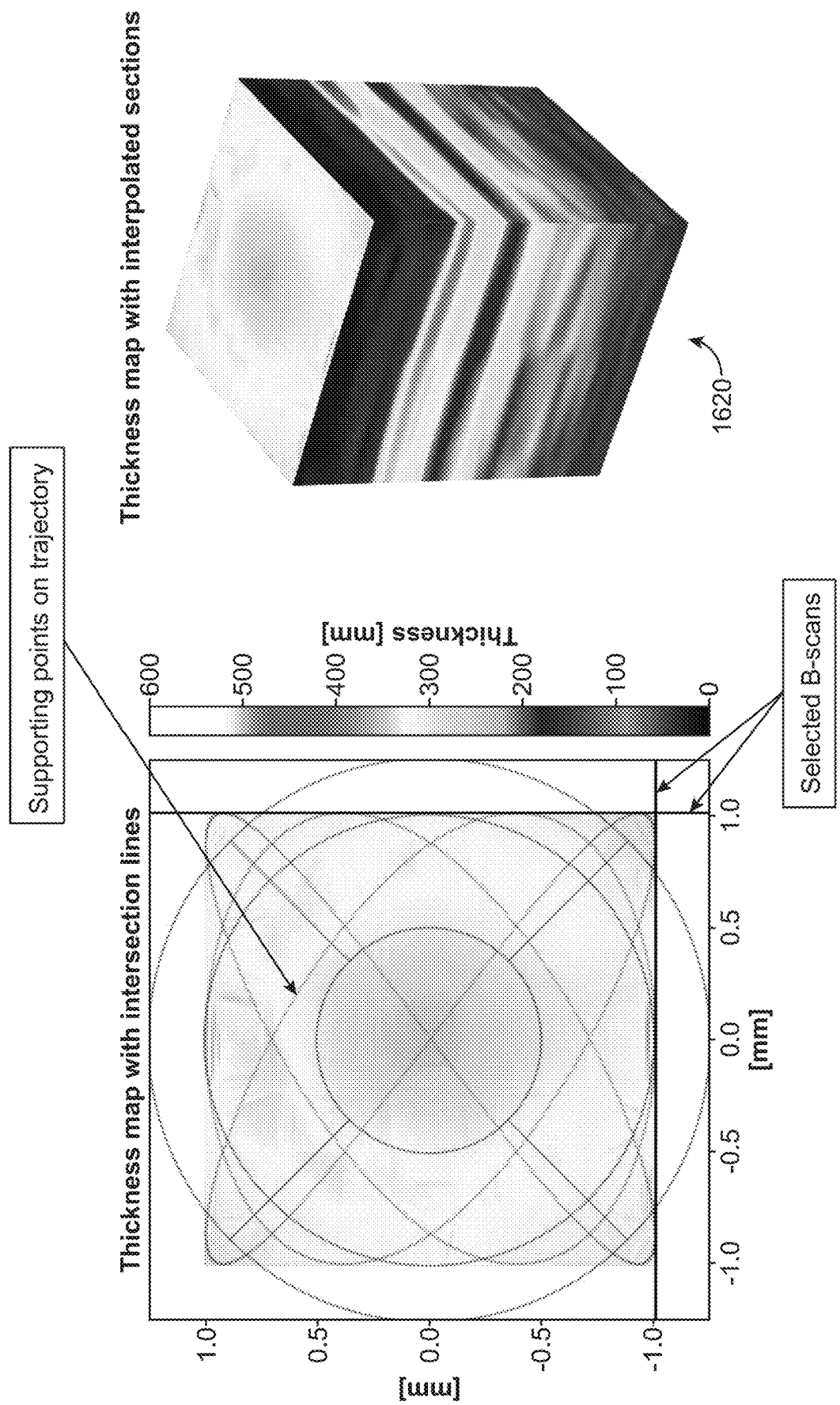
FIG. 16 is a diagram illustrating how a set of the created B-scans of different cross sections of a retina may be combined to produce a 3D visualization or thickness map of a retina, in accordance with some embodiments.

FIG. 16 is a diagram illustrating how a set of the created B-scans of different cross sections of a retina may be combined to produce a 3D visualization or thickness map of a retina 1620, in accordance with some embodiments. The figure illustrates how images generated from different sections of data obtained using a scan pattern may be combined to produce volumetric data that can be visualized over the scan pattern. Note that the thickness map is not limited to the 9 regions or zones described with respect to FIG. 6. This 3D volumetric data may also include internal structures such as fluid pooling.

Figure 17A:
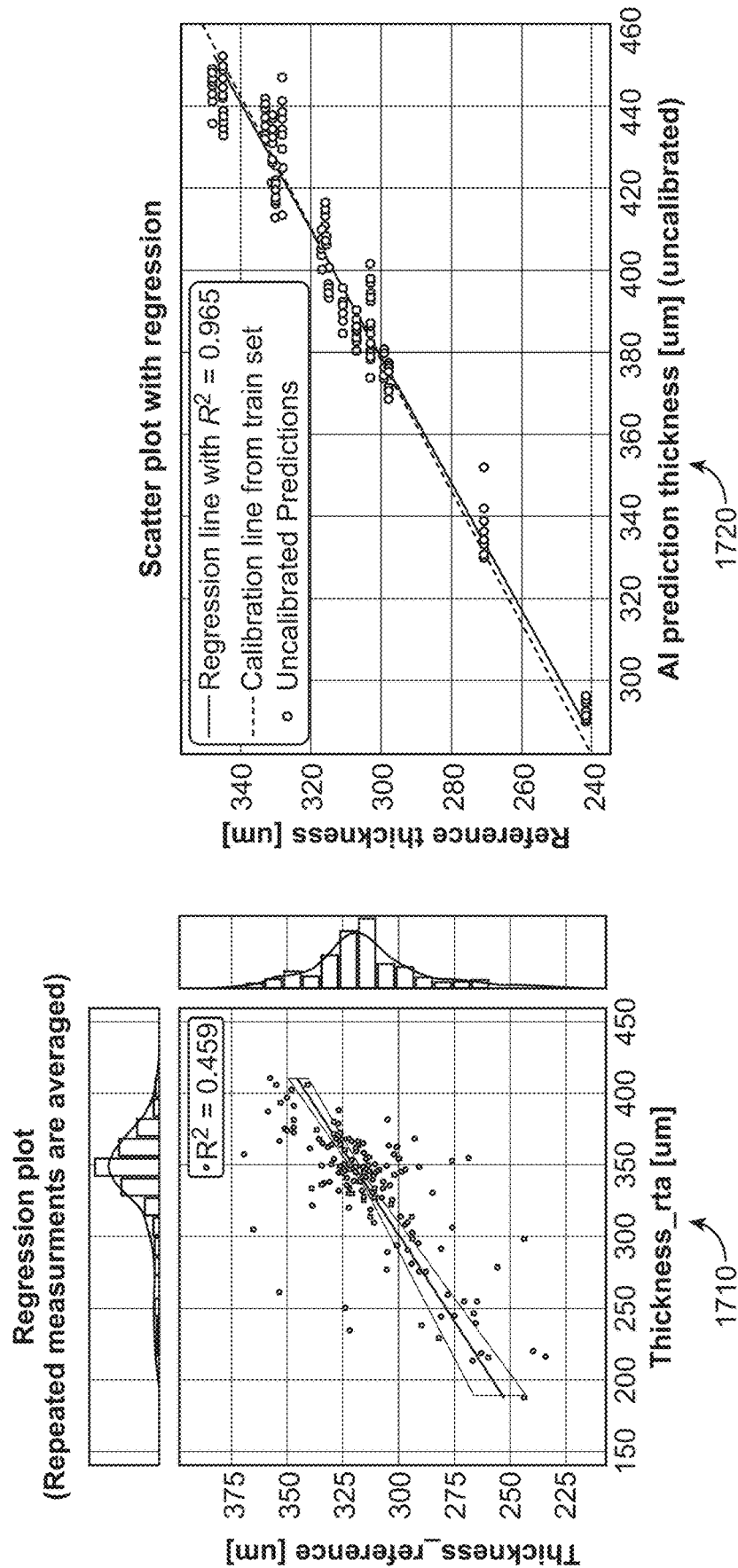
FIG. 17A is a diagram illustrating a comparison of the performance of a conventional scan pattern and data processing method to the results obtained using the flower scan pattern and image processing using the trained CNN described herein, in accordance with some embodiments.

FIG. 17A is a diagram illustrating a comparison of the performance of a conventional scan pattern and data processing method to the results obtained using the flower scan pattern and image processing using the trained CNN described herein, in accordance with some embodiments. Graph 1710 shows the variation or scatter in data obtained using a Lissajous scan pattern (in this example) and a Gaussian Mixture Model (GMM) data fitting approach. As indicated on graph 1710, the $R^2$ value for the "fit" to the regression model is a value of 0.459, suggesting a relatively large amount of variation in the data.

Graph 1720 shows the variation or scatter in data obtained using a flower scan pattern (with 12 petals or lobes, in this example) and a trained neural network of the type described herein for processing the image. As indicated on graph 1720, the Revalue for the "fit" to the regression line is a value of 0.965, suggesting a relatively smaller amount of variation in the data and a better fit to the regression model. This suggests that the trained neural network is capable of generating more consistent results.

Figure 17B:
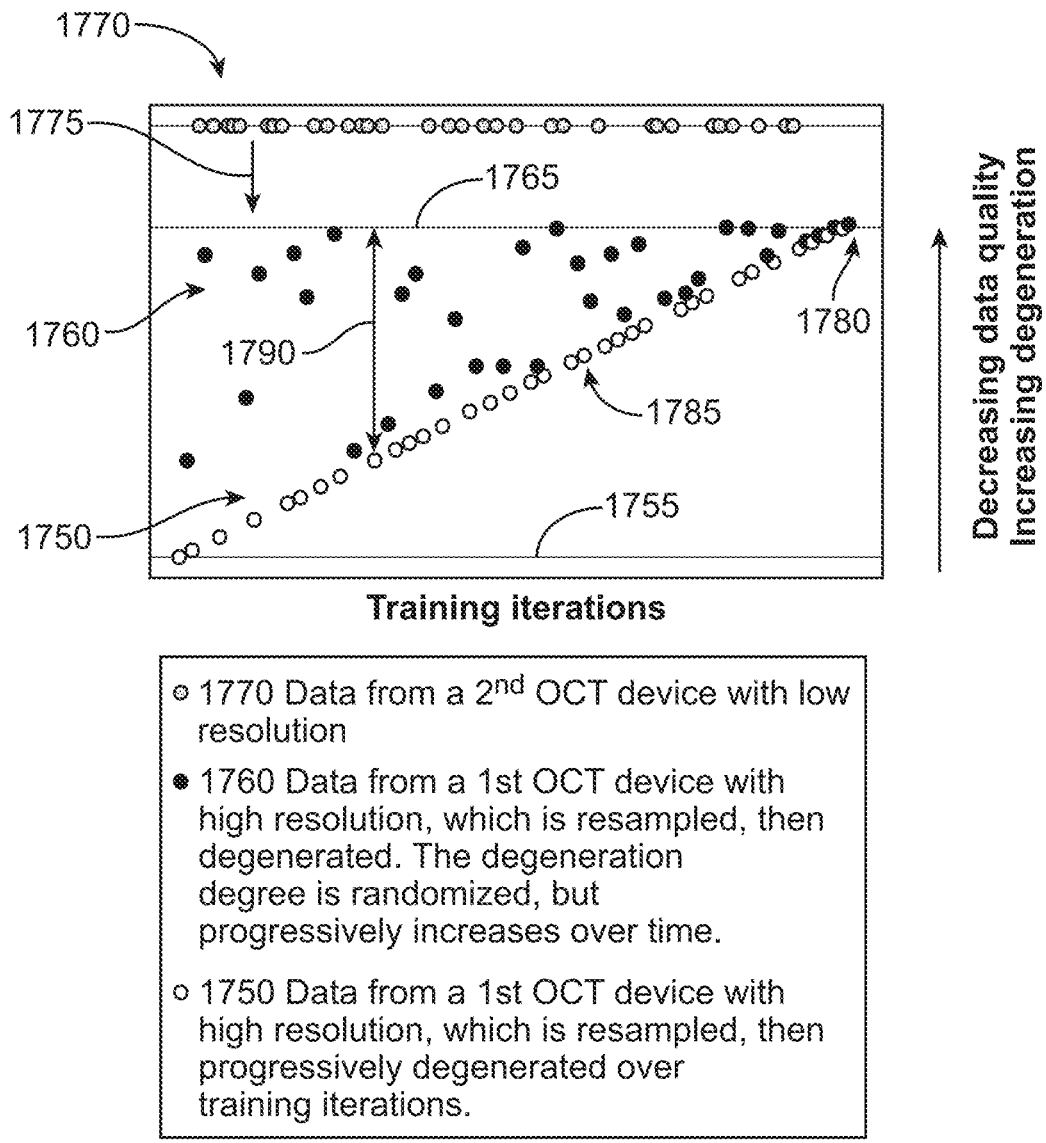
FIG. 17B is a diagram illustrating a curriculum training process in which image data and/or annotations obtained from a first and a second OCT device are used for training over a set of training iterations, with some of that data subjected to degeneration.

FIG. 17B is a diagram illustrating a curriculum training process in which image data and/or annotations obtained from a first OCT device configuration with higher resolution and a second OCT device configuration with lower resolution are used for training over a set of training iterations, with some of that data subjected to degeneration. The image quality and image degeneration of the training images are shown in relation to the training iterations. In some embodiments, increasing degeneration of the training images corresponds to decreasing image quality. Image data 1770 comprises a plurality of images from a $2^{nd}$ OCT device configuration, which includes a substantially fixed decreased image quality, e.g. lower resolution, increased distortion, noise, etc., such as a personalized biometry system (PBOS) as described herein. Three types of data are shown as follows: 1) data 1770 from the second OCT device configuration; 2) data 1760 from a first OCT device configuration with high resolution, which has been resampled, then degenerated, in which the degeneration is randomized and progressively increases over time; and 3) data 1750 from the first OCT device configuration with high resolution, which is resampled and then progressively degenerated with a linear increase in degeneration. In some embodiments, the pixel resolution of the training images remains substantially fixed while the degeneration increases and corresponding image quality decreases. For example, the substantially fixed pixel resolution of the resampled images may correspond to the resolution of the $2^{nd}$ OCT device configuration, such that the resampled and degenerated images from the first OCT device configuration can be combined with the images from the $2^{nd}$ OCT device configuration, for example interspersed among each other for the iterations of the training process.

The relative quality of the image data is also shown, which includes a target image quality 1765 (shown with a line) and a resampled image quality 1755 (shown with a line). The resampled image quality 1755 corresponds to the image quality of the resampled images from the first OCT device configuration with high resolution that have been down sampled to a lower lateral resolution and have not yet been degenerated. In some embodiments, resampling comprises lateral down sampling to provide a reduction of lateral resolution, and degeneration comprises axial down sampling to provide a reduction of axial resolution. The target image quality 1765 is chosen to correspond to the image quality of the image data 1770 from the second OCT device configuration with lower resolution, such that the degenerated image data mimics the image data 1770. For example, the quality of image data 1760 and image data 1750 converge toward the target image quality 1765 near the end 1780 of the training session 1780. This approach allows the trained network to receive input images from the second low resolution device and to output annotated images such as segmented images as described herein.

The quality of the image data 1770 from the lower resolution system is used to establish a target image quality 1765 for the training of the neural network. With progressive training iterations of the neural network, the quality of the degenerated input training images for the neural network converges toward target image quality 1765. This can be achieved by degenerating the resampled images. The resampled images may comprise image quality 1755. These resampled images can be degenerated by an appropriate amount and used as input to the training model. The amount of degeneration can be related to the number of training iterations. For example, resampled and linearly degenerated data 1750 is shown along a line 1785 which corresponds to linearly increasing image degeneration and linearly decreasing image quality. In some embodiments, the image quality is within a variable range 1790 that extends from the target amount 1765 to a lower threshold amount of degeneration shown at line 1785. The amount of degeneration can be increased with progressive iterations to provide input training images with an image quality that approximates image quality 1765 that is consistent with the image data 1770. As shown with arrow 1775, the image quality of the images 1770 corresponds to image quality 1765, such that the image quality of the degenerated images near the end of the training process substantially corresponds to the image quality of the lower resolution OCT system.

As shown in FIG. 17B, as the training iterations increase (moving to the right on the x-axis), the quality of the image data being used for training decreases (as indicated by the upward arrow along the y-axis). In some embodiments, the resolution of the data may be decreasing as the number of iterations of the training process increases. Alternatively, the resolution may be substantially fixed during the training process so as to correspond to the resolution of the second OCT device configuration with lower resolution. The decrease in data quality (e.g. resolution) may be the result of one or more of resampling data (e.g. data obtained from a OCT device with lower resolution), degenerating data obtained from a OCT device with higher resolution (e.g. where the degree of degeneration may be randomized and may increase as the number of iterations increases), or progressively degenerating data obtained from a OCT device with higher resolution as the number of iterations increases. The decrease in data quality with an increase in training iterations corresponds to an increase in task difficulty.

As discussed with reference to FIG. 11C, in some embodiments using curriculum learning, higher resolution image data may be degenerated to a greater degree as the number of iterations increases and/or lower resolution image data obtained from a different OCT system may be added to the training data set with a higher probability as the number of iterations increases.

In some embodiments, a combination of transfer learning and curriculum learning may be used in a training process. In such embodiments, a set of training images may be formed from two sources: images generated by a higher resolution OCT system configuration and images generated by a lower resolution OCT system configuration. The combination of images in the set of training images provides a source of transfer learning as inputs to a training process as described herein. The images generated by the higher resolution OCT system may be degenerated in one or more of many ways as described herein, e.g. resampled to a lower resolution and distorted, to better resemble the resolution and other properties of the images generated by the lower resolution OCT system. In order to generate the degenerated images, the images from the higher resolution OCT system may be subjected to a linear or randomly increasing amount of degeneration with each successive training iteration. In some embodiments, images from the OCT system with higher resolution are resampled, e.g. down sampled, to provide a lower resolution corresponding to the lower resolution OCT system configuration, and then further degenerated by an amount to correspond to the image quality of the lower resolution OCT system. The amount of degeneration may comprise a linearly increasing degeneration corresponding to a progressively increasing difficulty, or a randomly increasing degeneration with a randomly increasing difficulty of at least a threshold amount. In some embodiments, the overall set of training images is formed from a combination of the images generated by the lower resolution OCT system and the images formed by linear or randomly increasing the amount of degeneration of the resampled images generated by the higher resolution OCT system.

While the curriculum transfer learning can be configured in many ways, in some embodiments a level of difficulty for the next image in the training data set is determined, and an appropriate amount of degeneration is applied to the resampled OCT image from the higher resolution OCT image in order to provide the next image to the training dataset. The amount of degeneration may comprise a linearly increasing amount, or a random amount with a progressively increasing minimum threshold amount of degeneration, so that the degree of degeneration and corresponding difficulty generally increase toward image quality 1765. Referring again to FIG. 17B, image quality can be determined with reference to the image quality 1755 of the resampled high-resolution images and the image quality 1765 of corresponding to the low resolution OCT device. The resampled images with image quality 1755 can be degenerated by an appropriate amount to correspond to an appropriate amount of difficulty for a particular iteration. In some embodiments, the level of difficulty can be determined with a linearly increasing degree of difficulty, for example with reference to image data 1750, which has a linearly increasing amount of degeneration and linearly increasing difficulty, in which the high-resolution image data from the first OCT device configuration is resampled to correspond to image quality 1750 and then degenerated by an appropriate amount to correspond to the decreased image data quality shown. Alternatively or in combination, the degree of difficulty for a particular iteration may comprise a random amount of difficulty within a range 1790 extending from target image quality 1765 to a linearly increasing threshold amount shown with line 1785. For both the linearly increasing difficulty and the randomly increasing difficulty, as the number of iterations increase, the image quality approaches image quality 1765. Once the image quality, e.g. learning difficulty, for a training image has been determined, the resampled image can be degenerated by an appropriate amount to correspond to the determined image data quality and/or learning difficulty for the next training image in the dataset.

The approaches describe herein can be configured and combined in many ways, in accordance with the present disclosure. In some embodiments, an initial training data set comprises a plurality of images from a low-resolution OCT system and a plurality of resampled images from the higher resolution OCT system. The artificial intelligence model such as a neural network is trained with this initial data set. Once the training has been completed with the initial training data set, the model can then be trained with a resampled and degenerated images. The resampled and degenerated images may comprise a combination of images with a randomly selected difficulty (for example with reference to image data 1760) and a linearly increasing difficulty (for example with reference to image data 1750), both derived from a higher resolution OCT system configuration. In some embodiments, the resampled and degenerated images of increasing difficulty are combined with the lower resolution images (for example with reference to image data 1770) from the lower resolution system configuration.

In some embodiments, the training data set comprises a combination of images from a second low resolution OCT device configuration and degenerated images from a first higher resolution OCT device configuration. In some embodiments, the training data set comprises a combination of image data from a second low resolution OCT device configuration, e.g. image data 1770, resampled and linearly degenerated image data from a first higher resolution OCT device configuration, e.g. image data 1750, and resampled and randomly degenerated image data from a first higher resolution OCT device, e.g. image data 1760. In some embodiments, the pixel resolution of the training image data remains substantially fixed at the pixel resolution of the second lower resolution OCT device configuration. The image data input into the model may comprise segmented and grey level images subjected to degeneration and augmentation as described herein, for example.

Embodiments of the disclosed techniques and methods for generating training data and training a model (such as a neural network) to segment image data obtained from an OCT system comprise use of multiple combinations of image data and associated annotations, where one or more operations or processes may be applied to the image data, annotations, or both. In some embodiments, annotations associated with image data from a first OCT device may be resampled and registered to provide annotations for image data from a second OCT device, where the second device has a different scan pattern than the first device. The image data and annotations for the second device may then be used to train a model. If desired, the image data from the first device may also be used as training data after resampling.

In another embodiment, image data and associated annotations from a first device may be subjected to degeneration to generate training data and associated annotations corresponding to a second device having a lower resolution than the first device. The degenerated data and annotations may be subjected to one or more of resampling or augmentation to generate additional training data and annotations. The annotations may be registered to image data from the second device. The additional training data and/or image data and annotations for the second device may then be used to train a model.

In another embodiment, image data and associated annotations from a first device may be used as part of a transfer learning technique to generate training data and annotations for training a model to process data from a second device. In this embodiment, data from the second device is not used.

In another embodiment and example of a transfer learning process, image data from a first device is resampled, degenerated, and augmented with the associated annotations being resampled and augmented to generate training data and annotations for a model to process data from a second device. In this embodiment, image data and annotations from the second device are not used.

In another embodiment, image data and associated annotations for a first OCT device may be used as part of a transfer learning process with image data and associated annotations from a second OCT device to train a model to process data from the second device.

In another embodiment, image data from a first device is resampled, degenerated, and augmented with the associated annotations being resampled and augmented to generate training data and annotations for a model to process data from a second device. In this embodiment, image data and associated annotations from the second OCT device may be used as part of the training data for a model. In this or other embodiments, the annotations for the image data from the second device may be obtained directly from the image data for the second device or through a resampling and registering of annotations for image data from the first device.

The OCT systems, data processing methods and devices described herein may be operated or implemented in accordance with a variety of parameters, settings, programmed configurations, etc. The example operating parameters or characteristics, or range of parameters provided herein are intended to provide guidance to practicing the system and device (or to implementing the process or methods described) and are not meant to provide limits on operational characteristics. As will be apparent to one of skill, other combinations or values of operating parameters or characteristics are possible and are included within the description provided in this disclosure.

As an example, in some embodiments, the scan pattern is a flower pattern or rose curve and has a plurality of lobes. In some embodiments, the number of lobes may vary between four (4) and twenty-four (24). In some embodiments, a scan may be repeated by the device between two (2) and twenty (20) times to collect data.

In some embodiments, a measurement beam path of the scan pattern for a single scan extends a distance within a range from 10 mm to 100 mm, and optionally from 12 mm to 60 mm. In some embodiments, a total measurement beam path of the scan pattern repeated for the plurality of times extends a total distance within a range from 100 mm to 1000 mm, and optionally from 120 mm to 600 mm. In some embodiments, a total time of the scan pattern repeated the plurality of times is within a range from 1 to 3 seconds, and optionally within a range from 1.5 seconds to 2.5 seconds. In some embodiments, the scanner comprises one or more actuators for altering a position of the mirror to move the measurement beam on the retina. In some embodiments, a velocity of the measurement beam moving along the trajectory during a scan is within a range from 10 mm/s to 400 mm/s, and optionally from 15 mm/s to 300 mm/s. In some embodiments, a processor is configured with instructions to generate a plurality of A-scans of the retina with each A-scan comprising the scanner moving the measurement beam along each of the plurality of lobes of a scan pattern, and wherein a sampling rate of the A-scans is within a range from 10 kHz to 50 kHz, and optionally within a range from 15 kHz to 25 kHz.

As used herein, the terms "OCT device" and "OCT system" are used interchangeably.

As described herein, the computing devices and systems described and/or illustrated herein broadly represent any type or form of computing device or system capable of executing computer-readable instructions, such as those contained within the modules described herein. In their most basic configuration, these computing device(s) may each comprise at least one memory device and at least one physical processor.

The term "memory" or "memory device," as used herein, generally represents any type or form of volatile or non-volatile storage device or medium capable of storing data and/or computer-readable instructions. In one example, a memory device may store, load, and/or maintain one or more of the modules described herein. Examples of memory devices comprise, without limitation, Random Access Memory (RAM), Read Only Memory (ROM), flash memory, Hard Disk Drives (HDDs), Solid-State Drives (SSDs), optical disk drives, caches, variations or combinations of one or more of the same, or any other suitable storage memory.

In addition, the term "processor" or "physical processor," as used herein, generally refers to any type or form of hardware-implemented processing unit capable of interpreting and/or executing computer-readable instructions. In one example, a physical processor may access and/or modify one or more modules stored in the above-described memory device. Examples of physical processors comprise, without limitation, microprocessors, microcontrollers, Central Processing Units (CPUs), Field-Programmable Gate Arrays (FPGAs) that implement softcore processors, Application-Specific Integrated Circuits (ASICs), portions of one or more of the same, variations or combinations of one or more of the same, or any other suitable physical processor. The processor may comprise a distributed processor system, e.g. running parallel processors, or a remote processor such as a server, and combinations thereof.

Although illustrated as separate elements, the method steps described and/or illustrated herein may represent portions of a single application. In addition, in some embodiments one or more of these steps may represent or correspond to one or more software applications or programs that, when executed by a computing device, may cause the computing device to perform one or more tasks, such as the method step.

In addition, one or more of the devices described herein may transform data, physical devices, and/or representations of physical devices from one form to another. Additionally or alternatively, one or more of the modules recited herein may transform a processor, volatile memory, non-volatile memory, and/or any other portion of a physical computing device from one form of computing device to another form of computing device by executing on the computing device, storing data on the computing device, and/or otherwise interacting with the computing device.

The term "computer-readable medium," as used herein, generally refers to any form of device, carrier, or medium capable of storing or carrying computer-readable instructions. Examples of computer-readable media comprise, without limitation, transmission-type media, such as carrier waves, and non-transitory-type media, such as magnetic-storage media (e.g., hard disk drives, tape drives, and floppy disks), optical-storage media (e.g., Compact Disks (CDs), Digital Video Disks (DVDs), and BLU-RAY disks), electronic-storage media (e.g., solid-state drives and flash media), and other distribution systems.

A person of ordinary skill in the art will recognize that any process or method disclosed herein can be modified in many ways. The process parameters and sequence of the steps described and/or illustrated herein are given by way of example only and can be varied as desired. For example, while the steps illustrated and/or described herein may be shown or discussed in a particular order, these steps do not necessarily need to be performed in the order illustrated or discussed.

The various exemplary methods described and/or illustrated herein may also omit one or more of the steps described or illustrated herein or comprise additional steps in addition to those disclosed. Further, a step of any method as disclosed herein can be combined with any one or more steps of any other method as disclosed herein.

The processor as described herein can be configured to perform one or more steps of any method disclosed herein. Alternatively, or in combination, the processor can be configured to combine one or more steps of one or more methods as disclosed herein.

Unless otherwise noted, the terms "connected to" and "coupled to" (and their derivatives), as used in the specification and claims, are to be construed as permitting both direct and indirect (i.e., via other elements or components) connection. In addition, the terms "a" or "an," as used in the specification and claims, are to be construed as meaning "at least one of." Finally, for ease of use, the terms "including" and "having" (and their derivatives), as used in the specification and claims, are interchangeable with and shall have the same meaning as the word "comprising."

The processor as disclosed herein can be configured with instructions to perform any one or more steps of any method as disclosed herein.

It will be understood that although the terms "first," "second," "third", etc. may be used herein to describe various layers, elements, components, regions or sections without referring to any particular order or sequence of events. These terms are merely used to distinguish one layer, element, component, region or section from another layer, element, component, region or section. A first layer, element, component, region or section as described herein could be referred to as a second layer, element, component, region or section without departing from the teachings of the present disclosure.

As used herein, the term "or" is used inclusively to refer items in the alternative and in combination.

As used herein, characters such as numerals refer to like elements.

The present disclosure includes the following numbered clauses.

Clause 1. A method of processing data obtained from an OCT system, the method comprising: obtaining a first plurality of images, wherein each of the first plurality of images corresponds to data acquired by an OCT system performing a scan of a retina; annotating a plurality of pixels from each of the first plurality of images to generate segmented image data of the retina, wherein the annotation identifies one or more structures of the retina; generating a plurality of degenerated images from the first plurality of images by degenerating the first plurality of images; and training a neural network using the plurality of degenerated images and the segmented image data.

Clause 2. The method of clause 1, wherein annotating comprises assigning a classification for each pixel of the plurality of pixels from said each of the first plurality of images and optionally wherein said classification comprises an integer.

Clause 3. The method of clause 1, wherein the segmented image data comprises a plurality of segmented images, each of the plurality of segmented images comprising an annotation defining a class for each pixel of said each of the plurality of images.

Clause 4. The method of clause 1, wherein each of the plurality of segmented images corresponds to one of the plurality of degenerated images and wherein the plurality of segmented images and corresponding degenerated images are input to the neural network to train the model.

Clause 5. The method of clause 3, wherein the plurality of segmented images comprises a first plurality of segmented images corresponding to the first plurality of images and a second plurality of segmented images corresponding to the plurality of degenerated images.

Clause 6. The method of clause 1, wherein generating the plurality of degenerated images comprises applying a transform function to the first plurality of images to cause a geometric transformation of the first plurality of images.

Clause 7. The method of clause 5, wherein generating the plurality of degenerated images comprises applying a transform function to the first plurality of images to cause a geometric transformation of the first plurality of images, and wherein the transform function is applied to the first plurality of segmented images to obtain the second plurality of segmented images.

Clause 8. The method of clause 5, wherein each of the first plurality of segmented images comprises annotations at first locations for each of a first plurality of pixels of the first plurality of segmented images and wherein each of the second plurality of segmented images comprises the annotations at second locations for each of a second plurality of pixels of the second plurality of segmented images.

Clause 9. The method of clause 1, wherein, the one or more structures of the retina comprise background, retinal nerve fiber layer, ganglion cell layer and inner plexiform layer, outer plexiform layer and inner nuclear layer, outer nuclear layer and external limiting membrane, retinal pigment epithelium and photoreceptors, chorio-capillaries and chorio-septae, and optionally wherein the annotation comprises one or more of background, retina, intraretinal fluid, subretinal fluid, or retinal pigment epithelium detachment.

Clause 10. The method of clause 1, wherein, the first plurality of images is degenerated with one or more of resampling, down sampling, speckle noise, Y-Gaussian blur or A-Scan Y-jitter to generate the degenerated images.

Clause 11. The method of clause 1, wherein the plurality of degenerated images comprises augmented images.

Clause 12. The method of clause 11, wherein, the augmented images are generated by applying one or more of curving, horizontal flip, X-roll, Y-scale, Y-translate, elastic transformation or Gamma contrast to the first plurality of images.

Clause 13. The method of clause 11, wherein the augmented images are generated by applying a geometric transform to the first plurality of images.

Clause 14. The method of clause 13, wherein the geometric transform comprises one or more of curving, horizontal flip, X-roll, Y-scale, Y-translate, or elastic transformation.

Clause 15. The method of clause 5, further comprising: generating a first plurality of geometrically transformed segmented images by applying a geometric transform function to the first plurality of segmented images; and generating a second plurality of geometrically transformed segmented images by applying the geometric transform function to the second plurality of segmented images.

Clause 16. The method of clause 1, wherein the OCT system comprises a first configuration and wherein the plurality of degenerated images and segmented image data comprise a transfer learning data set configured to train the neural network to classify data from a second OCT system, the second OCT system comprising a second configuration different from the first configuration of the OCT system and optionally wherein the first configuration differs from the second configuration by one or more of an axial resolution, a scan pattern, or a lateral resolution.

Clause 17. The method of clause 16, wherein the transfer learning dataset comprises degenerated images and augmented images, the augmented images generated by applying one or more of curving, horizontal flip, X-roll, Y-scale, Y-translate, elastic transformation or Gamma contrast to the first plurality of images, and wherein the neural network is iteratively trained with a plurality of progressively increasingly degenerated images generated from the first plurality of images and wherein an amount of degeneration progressively approaches one or more of an axial resolution, a scan pattern, or a lateral resolution of images from the second configuration of the second OCT system.

Clause 18. The method of clause 1, wherein the first plurality of images corresponds to a first resolution of the OCT system and wherein the plurality of degenerated images corresponds to images of a second OCT system having a second resolution, wherein the first resolution is associated with a smaller resolvable feature size than the second resolution.

Clause 19. The method of clause 1, wherein the first plurality of images is annotated to define a ground truth data set for training the neural network and wherein the first plurality of images is resampled and registered with a second plurality of images from a second OCT system.

Clause 20. The method of clause 1, wherein the OCT system comprises a first OCT system, the first OCT system comprising a first configuration, and wherein the neural network, after training, is used to classify data from a second OCT system, the second OCT system comprising a second configuration different from the first configuration, and optionally wherein the first configuration differs from the second configuration with regards to one or more of an axial resolution, a scan pattern, or a lateral resolution.

Clause 21. The method of clause 20, wherein the neural network is not trained with data from the second OCT system.

Clause 22. The method of clause 20, wherein the first configuration of the OCT system comprises a first resolution and the second configuration of the second OCT system comprises a second resolution, and wherein the first resolution is associated with a smaller resolvable feature size than the second resolution.

Clause 23. The method of clause 20, wherein the neural network is trained with a transfer learning dataset, the transfer learning data set comprising first degenerated and augmented OCT images from the first OCT system and corresponding annotated OCT images from the first OCT system.

Clause 24. The method of clause 23, wherein the transfer learning dataset comprises second OCT images from the second OCT system and corresponding annotated OCT images from the second OCT system.

Clause 25. The method of clause 23, wherein the transfer learning dataset is derived from 1) resampled and annotated OCT image data from the first OCT system, 2) resampled, degenerated, and augmented OCT image data from the first OCT system; and 3) OCT image data and annotation data from the second OCT system.

Clause 26. The method of clause 23, wherein the transfer learning dataset comprises OCT data from a plurality of eyes and wherein each of the plurality of eyes is measured with the first OCT system and with the second OCT system.

Clause 27. The method of clause 1, wherein a difficulty of a next degenerated image is determined from resampled image data, and the next degenerated image is generated in response to the difficulty, the resampled image data generated by resampling the first plurality of images.

Clause 28. The method of clause 1, wherein the plurality of degenerated images comprises a plurality of images of an increasing difficulty.

Clause 29. The method of clause 28, wherein the increasing difficulty comprises a linearly increasing difficulty.

Clause 30. The method of clause 28, the increasing difficulty comprises a random difficulty above an increasing threshold of difficulty.

Clause 31. The method of clause 28, wherein the increasing difficulty increases toward a difficulty of images from a second OCT system, the second OCT system comprising a lower resolution than the OCT system.

Clause 32. The method of clause 28, wherein the increasing difficulty comprises a combination of a linearly increasing difficulty and a randomly increasing difficulty.

Clause 33. A method of generating a segmented OCT image, comprising: receiving an OCT image, the OCT image comprising an axial resolution and a first plurality of pixels, wherein each of the first plurality of pixels is associated with a corresponding grey level; processing the received OCT image with a trained model to generate the segmented OCT image comprising a second plurality of pixels, wherein each of the second plurality of pixels is assigned to a class by the trained model, wherein the class comprises one of background, retina, intraretinal fluid, subretinal fluid, or retinal pigment epithelium detachment; and outputting the segmented OCT image.

Clause 34. The method of clause 33, wherein the retina class comprises one or more pools of intraretinal fluid not visible in the received OCT image and wherein the one or more pools of intraretinal fluids is visible in the segmented OCT image.

Clause 35. The method of clause 33, wherein the trained model comprises a neural network and each of the plurality of pixels is assigned to the class in response to a probability function of the neural network.

Clause 36. The method of clause 33, wherein the trained model comprises a trained machine learning model that generates a neural network.

Clause 37. The method of clause 33, wherein the trained model comprises a neural network and the neural network has been trained with a plurality of OCT images having a resolution associated with a smaller resolvable feature size than the axial resolution of the OCT image.

Clause 38. A method of processing data obtained from an OCT system, the method comprising: obtaining a first plurality of images, wherein each of the first plurality of images corresponds to data acquired by a first OCT system performing a first plurality of scans of a plurality of retinas with a first scan pattern; annotating a first plurality of pixels from each of the first plurality of images, wherein the annotations comprise an indication of a region of a retina; resampling data for the first plurality of pixels from said each of the first plurality of images to generate a second plurality of images corresponding to images that would be acquired with a second OCT system performing a scan of the plurality of retinas with a second scan pattern different from the first scan pattern; and training a neural network using the second plurality of images and the annotations.

Clause 39. The method of clause 38, further comprising aligning the resampled data using the annotations.

Clause 40. The method of clause 39, further comprising generating additional training data for the neural network by augmenting or degenerating the first plurality of images prior to resampling the data for the first plurality of pixels and using the annotations to align the resampled data.

Clause 41. The method of clause 40, wherein augmenting the first plurality of images further comprises one or more of applying curving, horizontal flip, X-roll, Y-scale, Y-translate, elastic transformation or Gamma contrast to the first plurality of images.

Clause 42. The method of clause 40, wherein degenerating the first plurality of images further comprises applying one or more of resampling, down sampling, speckle noise, Y-Gaussian blur or A-Scan Y-jitter to the first plurality of images.

Clause 43. The method of clause 38, wherein the first scan pattern is a linear scan pattern and the second scan pattern comprises a plurality of lobes.

Clause 44. A method of processing data obtained from an OCT system, comprising: obtaining a first plurality of interferograms, wherein each of the interferograms corresponds to data acquired by a first OCT system performing a scan of a retina using a first scan pattern; annotating each of the first plurality of interferograms formed from the data acquired using the first scan pattern to indicate a tissue structure of the retina; training a neural network using the first plurality of interferograms and the annotations; inputting a second plurality of interferograms into the trained neural network, the second plurality of interferograms corresponding to data acquired by a second OCT system performing a scan of a retina using a second scan pattern; and obtaining an output from the trained neural network, the output indicating the tissue structure of the retina that was scanned using the second scan pattern.

Clause 45. The method of clause 44, wherein the first scan pattern comprises a linear scan pattern and the second scan pattern comprises a curved scan pattern.

Clause 46. The method of clause 45, wherein the linear scan pattern comprises one or more of a radial scan pattern or a raster scan pattern and wherein the curved scan pattern comprises a plurality of lobes.

Clause 47. The method of clause 45, wherein the first plurality of interferograms corresponds to a B-scan of the retina along the first scan pattern and the second plurality of interferograms comprises a plurality of A-scans of the retina arranged along the curved scan pattern.

Clause 48. The method of clause 44, wherein the tissue structure comprises one or more of an inner limiting membrane (ILM) or a retinal pigment epithelium (RPE).

Clause 49. The method of clause 44, wherein the neural network comprises a convolutional neural network.

Clause 50. The method of clause 44, wherein the second scan pattern comprises a rose curve.

Clause 51. The method of clause 44, further comprising: generating additional training data for the neural network based on the first plurality of interferograms by performing one or more processing operations on one or more of the first plurality of interferograms, the one or more processing operations comprising one or more of random horizontal flipping, random shifting in the x direction, random scaling along an axis, random translation along a direction, a blurring operation, or a variable elastic transformation; annotating the additional training data based on the annotations of the one or more of the first plurality of interferograms to which were applied the processing operations; and training the neural network using the additional training data and the annotations for the additional training data.

Clause 52. The method of clause 44, further comprising training the neural network using data comprising the first plurality of interferograms and the annotations based on the first scan pattern and data comprising the second plurality of interferograms and annotations for the second plurality of interferograms based on the second scan pattern.

Clause 53. The method of clause 52, further comprising prior to training the neural network, processing the second plurality of interferograms to produce interferograms that correspond to the first plurality of interferograms.

Clause 54. The method of clause 53, wherein the first scan pattern comprises a linear scan pattern and the second scan pattern comprises a plurality of lobes, and wherein processing the second plurality of interferograms comprises interpolating the data acquired from the second scan pattern to produce data corresponding to the linear scan pattern.

Clause 55. The method of clause 51, wherein the blurring operation is performed using a Gaussian blur operation.

Clause 56. The method of clause 52, wherein each of the first plurality of interferograms based on the first scan pattern and a corresponding one of the second plurality of interferograms based on the second scan pattern are obtained from scans on the same retina.

Clause 57. The method of clause 44, wherein the first plurality of interferograms based on the first scan pattern comprise a higher resolution scan having a resolution associated with a smaller resolvable feature size than the second plurality of interferograms based on the second scan pattern.

Clause 58. The method of clause 57, wherein the first scan pattern comprises a plurality of linear scans and the second scan pattern comprises a plurality of lobes.

Clause 59. The method of clause 58, wherein prior to using the first plurality of interferograms to train the neural network, each of the first plurality of interferograms is subjected to a blurring operation.

Clause 60. The method of clause 44, wherein the first scan pattern comprises a linear scan pattern and the second scan pattern comprises a plurality of lobes, and prior to inputting the second plurality of interferograms, the method further comprises interpolating the data acquired from the second scan pattern to produce data that would result from a linear scan pattern.

Clause 61. The method of clause 60, further comprising: generating a set of input data from the second scan pattern, with each of the set comprising interpolated data representing a radial scan of a retina for a specific plane; and combining the outputs of the trained neural network to form a 3D image of the retina.

Clause 62. The method of clause 49, wherein the convolutional neural network comprises a U-Net architecture that comprises a plurality of convolutional neural network layers.

Clause 63. The method of clause 49, wherein the convolutional neural network comprises a contractor path and an expansion path, the convolutional neural network configured to exchange spatial features with semantic values along the contractor path and to exchange the semantic features with the spatial features along the expansion path.

Clause 64. The method of clause 44, wherein the neural network comprises a plurality of semantic feature channels corresponding to an ILM layer and an RPE layer of a retina.

Clause 65. The method of clause 44, wherein the first plurality of interferograms comprises a B-scan image and the output of the trained neural network comprises a B-scan image that would be obtained with data from the second scanning pattern, the second scanning pattern different from the first scanning pattern.

Clause 66. The method of clause 49, wherein the convolution neural network comprises a number of convolutional layers within a range from about 10 to about 40, a number of biases and weights within a range from about 1 million to about 4 million and a number of semantic feature channels within a range from about 10 to about 500.

Clause 67. The method of clause 44, wherein the first plurality of interferograms comprises an axial resolution within a range from about 1 micron to about 5 microns and wherein the second plurality of interferograms comprises an axial resolution within a range from about 6 microns to about 30 microns.

Clause 68. The method of clause 44, wherein the first scan pattern comprises a linear scan pattern and the second scan pattern comprises the linear scan pattern.

Clause 69. The method of clause 44, wherein the first scan pattern comprises a curved scan pattern and the second scan pattern comprises the curved scan pattern.

Clause 70. A method of processing an image of a retina, comprising: receiving a plurality of A-scans corresponding to a plurality of locations along an OCT scan pattern; inputting the plurality of A-scans into a trained neural network; and outputting a segmented image from the trained neural network corresponding to the plurality of locations along the OCT scan pattern, the segmented image comprising an identification of one or more of a boundary of an ILM layer, a boundary of an RPE layer, or a boundary of a pool of fluid within the retina.

Clause 71. The method of clause 70, wherein the plurality of A-scans is interpolated to generate a plurality of B-scan images and wherein the plurality of B-scan images is input into a convolutional neural network to generate a plurality of segmented B-scan images, and wherein the plurality of segmented B-scan images is interpolated to generate the segmented image corresponding to the plurality of locations along the OCT scan pattern.

Clause 72. The method of clause 70, wherein the OCT scan pattern comprises a curved scan pattern and wherein the plurality of A-scans along the curved scan pattern is input into a trained convolutional neural network configured to output the segmented image, the segmented image comprising a plurality of segmented A-scans corresponding to the plurality of locations along the curved scan pattern.

Clause 73. The method of clause 72, wherein the convolutional neural network comprises a contractor path and an expansion path, the convolutional neural network configured to exchange spatial features with semantic values along the contractor path and to exchange the semantic features with the spatial features along the expansion path.

Clause 74. The method of clause 72, wherein the convolutional neural network comprises a number of convolutional layers within a range from about 10 to about 40, a number of biases and weights within a range from about 1 million to about 4 million and a number of semantic feature channels within a range from about 10 to about 500.

Clause 75. The method of clause 70, further comprising: processing the plurality of A-scans to generate a B-scan image, with the B-scan image corresponding to a radial scan of a retina for a specific plane; inputting the B-scan image into a convolutional neural network, wherein the convolutional neural network outputs the segmented image; repeating the processing and inputting steps for multiple pluralities of A-scans with each of the multiple pluralities corresponding to a different plane; and combining the outputs of the convolutional neural network to form a 3D image of the retina.

Clause 76. The method of clause 75, wherein processing the plurality of A-scans to generate a B-scan image further comprises interpolating data from the A-scans.

Clause 77. A method of processing an OCT image, comprising: receiving the OCT image; inputting the received OCT image into a trained neural network; and receiving a segmented image as output from the trained neural network, the segmented image corresponding to the input OCT image and comprising an identification of one or more of a boundary of an ILM layer, a boundary of an RPE layer, or a boundary of a pool of fluid within the retina.

Clause 78. The method of clause 77, wherein the neural network is trained using a set of training data and a corresponding set of annotations for the set of training data.

Clause 79. The method of clause 78, wherein the set of training data comprises a plurality of OCT images obtained using a first scan pattern.

Clause 80. The method of clause 79, wherein the training data further comprises a set of augmented images generated from the plurality of OCT images.

Clause 81. The method of clause 80, wherein the set of augmented images is generated by applying one or more of curving, horizontal flip, X-roll, Y-scale, Y-translate, elastic transformation or Gamma contrast to the plurality of OCT images.

Clause 82. The method of clause 79, wherein the training data further comprises a set of degenerated images generated from the plurality of OCT images.

Clause 83. The method of clause 82, wherein the set of degenerated images is generated by applying one or more of resampling, down sampling, speckle noise, Y-Gaussian blur or A-Scan Y-jitter to the plurality of OCT images.

Clause 84. The method of clause 79, wherein the training data further comprises a second plurality of OCT images obtained by resampling the plurality of images obtained using the first scan pattern to produce a plurality of images based on a second scan pattern.

Clause 85. The method of clause 84, wherein the first scan pattern is a linear scan pattern and the second scan pattern comprises a plurality of lobes.

Clause 86. An apparatus, comprising: a set of computer-executable instructions; a processor configured with the set of computer-executable instructions, wherein when executed by the processor, the set of instructions cause the processor to perform the method any one of the preceding clauses.

Embodiments of the present disclosure have been shown and described as set forth herein and are provided by way of example only. One of ordinary skill in the art will recognize numerous adaptations, changes, variations and substitutions without departing from the scope of the present disclosure. Several alternatives and combinations of the embodiments disclosed herein may be utilized without departing from the scope of the present disclosure and the inventions disclosed herein. Therefore, the scope of the presently disclosed inventions shall be defined solely by the scope of the appended claims and the equivalents thereof.

What is claimed is:

1. A method of processing data obtained from an OCT system, the method comprising:
    obtaining a first plurality of images, wherein each of the first plurality of images corresponds to data acquired by a first OCT system performing a scan of a retina;
    annotating a plurality of pixels from each of the first plurality of images to generate segmented image data of the retina, wherein the annotation identifies one or more structures of the retina;
    generating a plurality of degenerated images from the first plurality of images by degenerating the first plurality of images; and
    training a neural network using the plurality of degenerated images and the segmented image data;
    wherein the plurality of degenerated images comprises a plurality of images of an increasing difficulty and wherein the increasing difficulty increases toward a difficulty of images from a second OCT system, the second OCT system comprising a lower resolution than the first OCT system.

2. The method of claim 1, wherein the segmented image data comprises a plurality of segmented images, each of the plurality of segmented images comprising an annotation defining a class for each pixel of said each of the plurality of images.

3. The method of claim 2, wherein the plurality of segmented images comprises a first plurality of segmented images corresponding to the first plurality of images and a second plurality of segmented images corresponding to the plurality of degenerated images.

4. The method of claim 3, wherein generating the plurality of degenerated images comprises applying a transform function to the first plurality of images to cause a geometric transformation of the first plurality of images, and wherein the transform function is applied to the first plurality of segmented images to obtain the second plurality of segmented images.

5. The method of claim 3, wherein each of the first plurality of segmented images comprises annotations at first locations for each of a first plurality of pixels of the first plurality of segmented images and wherein each of the second plurality of segmented images comprises annotations at second locations for each of a second plurality of pixels of the second plurality of segmented images.

6. The method of claim 1, wherein, the one or more structures of the retina comprise one or more of background, retinal nerve fiber layer, ganglion cell layer and inner plexiform layer, outer plexiform layer and inner nuclear layer, outer nuclear layer and external limiting membrane, retinal pigment epithelium and photoreceptors, chorio-capillaries or chorio-septae.

7. The method of claim 1, wherein the plurality of degenerated images comprises augmented images and wherein the augmented images are generated by applying a geometric transform to the first plurality of images and wherein the geometric transform comprises one or more of curving, horizontal flip, X-roll, Y-scale, Y-translate, or elastic transformation.

8. The method of claim 3, further comprising:
    generating a first plurality of geometrically transformed segmented images by applying a geometric transform function to the first plurality of segmented images; and
    generating a second plurality of geometrically transformed segmented images by applying the geometric transform function to the second plurality of segmented images.

9. The method of claim 1, wherein the first OCT system comprises a first configuration and wherein the plurality of degenerated images and segmented image data comprise a transfer learning data set configured to train the neural network to classify data from the second OCT system, the second OCT system comprising a second configuration different from the first configuration of the first OCT system.

10. The method of claim 1, wherein the first plurality of images corresponds to a first resolution of the first OCT system and wherein the plurality of degenerated images corresponds to images of the second OCT system having a second resolution, wherein the first resolution is associated with a smaller resolvable feature size than the second resolution.

11. The method of claim 1, wherein the first OCT system comprises a first configuration, and wherein the neural network, after training, is used to classify data from the second OCT system, the second OCT system comprising a second configuration different from the first configuration, and wherein the first configuration differs from the second configuration with regards to one or more of an axial resolution, a scan pattern, or a lateral resolution.

12. The method of claim 11, wherein the neural network is not trained with data from the second OCT system.

13. The method of claim 11, wherein the first configuration of the first OCT system comprises a first resolution and the second configuration of the second OCT system comprises a second resolution, and wherein the first resolution is associated with a smaller resolvable feature size than the second resolution.

14. The method of claim 11, wherein the neural network is trained with a transfer learning dataset, the transfer learning data set comprising first degenerated and augmented OCT images from the first OCT system and corresponding annotated OCT images from the first OCT system.

15. The method of claim 14, wherein the transfer learning dataset comprises second OCT images from the second OCT system and corresponding annotated OCT images from the second OCT system.

16. The method of claim 14, wherein the transfer learning dataset is derived from 1) resampled and annotated OCT image data from the first OCT system, 2) resampled, degenerated, and augmented OCT image data from the first OCT system; and 3) OCT image data and annotation data from the second OCT system.

17. The method of claim 14, wherein the transfer learning dataset comprises OCT data from a plurality of eyes and wherein each of the plurality of eyes is measured with the first OCT system and with the second OCT system.

18. The method of claim 1, wherein a difficulty of a next degenerated image is determined from resampled image data, and the next degenerated image is generated in response to the difficulty, the resampled image data generated by resampling the first plurality of images.

19. The method of claim 1, wherein the first plurality of images acquired with the first OCT system comprises one or more pools of intraretinal fluid not visible in the plurality of degenerated images and wherein the one or more pools of intraretinal fluid is visible in a segmented OCT image generated with the trained neural network from the plurality of degenerated images.

20. The method of claim 1, wherein the first plurality of images has been generated with a first scan pattern comprising a linear scan pattern of the first OCT system and the plurality of degenerated images corresponds to a second scan pattern of the second OCT system comprising a plurality of lobes.

21. The method of claim 20, wherein the second scan pattern of the second OCT system comprises a lower lateral resolution and a lower axial resolution than the first OCT system.

* * * * *